US011987555B2

(12) United States Patent
Einziger et al.

(10) Patent No.: US 11,987,555 B2
(45) Date of Patent: *May 21, 2024

(54) *MALASSEZIN* AND ANALOGS THEREOF AS SKIN BRIGHTENING AGENTS

(71) Applicant: Versicolor Technologies, LLC, Santa Monica, CA (US)

(72) Inventors: Michael Einziger, Malibu, CA (US); Ann Marie Simpson, Malibu, CA (US)

(73) Assignee: VERSICOLOR TECHNOLOGIES, LLC, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/409,702

(22) Filed: Aug. 23, 2021

(65) Prior Publication Data

US 2021/0380532 A1    Dec. 9, 2021

Related U.S. Application Data

(62) Division of application No. 16/121,353, filed on Sep. 4, 2018, now Pat. No. 11,104,644, which is a division of application No. 15/455,932, filed on Mar. 10, 2017, now Pat. No. 10,131,631.

(60) Provisional application No. 62/306,468, filed on Mar. 10, 2016.

(51) Int. Cl.
*C07D 209/12* (2006.01)
*A61K 8/49* (2006.01)
*A61Q 19/02* (2006.01)
*C07D 487/04* (2006.01)

(52) U.S. Cl.
CPC ............ *C07D 209/12* (2013.01); *A61K 8/492* (2013.01); *A61Q 19/02* (2013.01); *C07D 487/04* (2013.01)

(58) Field of Classification Search
CPC .................................................. C07D 209/12
See application file for complete search history.

(56) References Cited

U.S. PATENT DOCUMENTS

| | | | |
|---|---|---|---|
| 7,855,310 B2 | 12/2010 | Herrmann et al. |
| 9,969,686 B2 | 5/2018 | Tang et al. |
| 10,131,631 B2 | 11/2018 | Einziger et al. |
| 10,730,833 B2 | 8/2020 | Tang et al. |
| 11,104,644 B2 | 8/2021 | Einziger et al. |
| 2007/0258921 A1 | 11/2007 | Dalko |
| 2010/0324109 A1 | 12/2010 | Saurat |
| 2016/0039754 A1 | 2/2016 | Tang et al. |
| 2018/0222861 A1 | 8/2018 | Tang et al. |
| 2018/0370913 A1 | 12/2018 | Einziger et al. |

FOREIGN PATENT DOCUMENTS

| | | |
|---|---|---|
| JP | 2007297387 A | 11/2007 |
| JP | 2009536933 A | 10/2009 |
| JP | 2010037251 A | 2/2010 |
| WO | WO 2002/068389 A2 | 9/2002 |
| WO | WO 2009/093207 A1 | 7/2009 |
| WO | 2017156424 A1 | 9/2017 |

OTHER PUBLICATIONS

C. W. Lynde, STL vol. 6, No. 13, Dec. 1, 2001.*
Marie Loden, Am. J. Clin Dermatol. 2003, 4(11) 771-788.*
Berridge et al. (1996). The Biochemical and Cellular Basis of Cell Proliferation Assays that Use Tetrazolium Salts. Biochemica; 4:14-19.
Black et al. (1985). Athymic Nude Mice and Human Skin Grafting. In: Maibach et al. (eds). Models in Dermatology; vol. 1, Karger, Basel; 228-39.
Costin, G.-#, Raabe. R. (2013). Optimized in Vitro Pigmentation Screening Assay Using a Reconstructed Three Dimensional Human Skin Model. Rom. J. Biochem.; 50(1): 15-27.
Donato et al. (1993). A Microassay for Measuring Cylochrome P450IA1 and P450IIB1 Activities in Intact Human and Rat Hepatocytes Cultured on 96-Well Plates. Anal Biochem; 213(1): 29-33.
Elmore (2007). Apoptosis: A Review of Programmed Cell Death. Toxicologic Pathology; 35:495-516.
European Patent Office (EPO) Communication, European Patent Application No. 17711992.2, dated Oct. 28, 2020.
Fitzpatrick et al. (1988). The Validity and Practicality of Sun-Reactive Skin Types I Through VI. Arch Dermatol.; 124(6):869-871.
Gaitanis et al. (2013). Skin Diseases Associated with Malassezia Yeasts: Facts and Controversies. Clinics in Dermatology; 31:455-463.
Gueho et al. (1996). The Genus *Malassezia* with Description of Four New Species. Antonie Van Leeuwenhoek; 59:337-55.
Jux, B. et al. (2011). The Aryl Hydrocarbon Receptor Mediates UVB Radiation-Induced Skin Tanning. Journal of Investigative Dermatology; (131):203-210.
Karchner et al. (1999). Identification and Functional Characterization of Two Highly Divergent Aryl Hydrocarbon Receptors (AHR1 and AHR2) in the Teleost Fundulus Heteroclitus. The Journal of Biological Chemistry; 274 (47):33814-24.
Kramer et al. (2005). Malassezin, A Novel Analyst of the Aryl Hydrocarbon Receptor from the Yeast *Malassezia furfur*, Induces Apoptosis in Primary Human Melanocytes. ChemBioChem; 6:860-5.
Lee et al. (2013). Comparison of Gene Expression Profiles Between Keratinocytes, Melanocytes and Fibroblasts. Ann Dermatol.; 25(1):36-45.
Magiatis, P. et al. (2013). Malassezia Yeasts Produce a Collection of Exceptionally Potent Activators of Ah (Dioxin) Receptor Detected in Diseased Human Skin. Journal of Investigative Dermatology (133):2023-2030.

(Continued)

*Primary Examiner* — Shawquia Jackson

(57) ABSTRACT

The present invention relates to compounds, compositions, and methods for brightening skin. The compounds, compositions, and methods of the present invention generally involve compounds produced by a *Malassezia* yeast, and chemical analogs thereof. In addition to skin brightening applications, the compounds, compositions, and methods of the present invention may be used to modulate melanocyte activity, induce melanocyte apoptosis, agonize an arylhydrocarbon receptor (AhR), improve hyperpigmentation caused by a hyperpigmentation disorder, and modulate melanin production, melanosome biogenesis, and melanosome transfer.

15 Claims, 56 Drawing Sheets

(56) References Cited

OTHER PUBLICATIONS

Manning et al. (1973). Maintenance of Skin Xenografts of Widely Divergent Phylogenetic Origin on Congenitally Athymic (Nude) Mice. J Exp Med; 138:488-94.
Mexican Institute of Industrial Property (IMPI) Communication, MX/A/2018/010962, dated Mar. 12, 2021. (Original and English-language translation).
Nazzaro-Porro et al. (1978). Identification of Tyrosinase Inhibitors in Cultures of Pityrosporum. The Journal of Investigative Dermatology; 71:205-208.
Noakes (2015). The Aryl Hydrocarbon Receptor: A Review of Its Role in the Physiology and Pathology of the Integument and Its Relationship to the Tryptophan Metabolism. Journal of Tryptophan Research; 8:7-18.
Otulakowski et al. (1994). Use of a Human Skin-Grafted Nude Mouse Model for the Evaluation of Topical Retinoic Acid Treatment. J Invest Dermatol; 102:515-8.
Park, J.I. et al. (2016). Inhibitory Effect of 2-methyl-naphtho [1,2,3-de] quinolin-8-one on melanosome transport and skin pigmentation. Sci. Rep. Jul. 6:6:29189. Doi: 10.1038/srep29189.
Plenat et al. (1992). Host-Donor Interactions in Healing of Human Split-Thickness Skin Grafts Onto Nude Mice: In Situ Hybridization, Immunohistochemical and Histochemical Studies. Transplantation; 53:1002-10.
Reed et al. (1973). Long-Term Maintenance of Normal Human Skin on Congenitally Athymic (Nude) Mice. Proc Soc Exp Bio Med; 143:350-3.
Scott et al. (1968). The Permeability of Grafted Human Transplant Skin in Athymic Mice. J Pharm Pharmacol; 40:128-9.
Song et al. (2002). A Ligand for the Aryl Hydrocarbon Receptor Isolated From Lung. PNAS; 99(23):14694-9.
Taylor et al. (2005). The Taylor Hyperpigmentation Scale: a new visual assessment tool for the evaluation of skin color and pigmentation. Cutis; 76(4):270-4.
Tholander et al. (1998). Synthesis of 6-Formylindolo [3,2-b] carbazole, an Extremely Potent Ligand for the Aryl Hydrogen (Ah) Receptor. Tetrahedron Letters; 39:1619-1622.
Tholander et al. (1999). Syntheses of 6,12-Disubstituted 5,11-Dihydroindolo [3,2-b] carbazoles, Including 5,11-Dihydroindolo [3,2-b] carbazole-6, 12-dicarbaldehyde, an Extremely Efficient Ligand for the TCDD (Ah) Receptor. Tetrahedron; 55:12577-12594.
Tholander et al. (1999). Syntheses of 6-Sustituted Indolo [3,2-b] carbazoles, Including 6-Formylindolo [3,2-b] carbazole, an Extremely Efficient Ligand for the TCDD (Ah) Receptor. Tetrahedron; 55:6243-6260.
Waller et al. (1995). Three-Dimensional Quantitative Structure-Activity Relationships of Dioxins and Dioxin-like Compounds: Model Validation and Ah Receptor Characterization. Chem. Res. Toxicol. 8:847-858.
Wang et al. (2014). Stress-Induced RNASET2 Overexpression Mediates Melanocyte Apoptosis Via The TRAF2 Pathway In Vitro. Cell Death and Disease; 5:e1022.
Wasmeier et al. (2008). Melanosomes at a Glance. Journal of Cell Science 2008; 121:3995-3999.
Wille et al. (2001). Malassezian—A Novel Agonist of the Arylhydrocarbon Receptor from the Yeast *Malassezia furfur*. Bioorganic & Medicinal Chemistry; 9:955-60.
Winston-McPherson et al. (2014). Synthesis and Biological Evaluation of 2,3'-diindolylmethanes as Agonists of Aryl Hydrocarbon Receptor. Bioorganic & Medicinal Chemistry Letters; 24:4023-4025.
Whyte et al. (2000). Ethoxyresorufin-O-deethylase (EROD) Activity in Fish as a Biomarker of Chemical Exposure. Critical Reviews in Toxicology; 30(4):347-570.
Yamaguchi et al. (2014). Melanocytes and Their Diseases. Cold Spring Harb Perspect Med; 4:a017046.
Zonios et al. (2001). Skin Melanin, Hemoglobin, and Light Scattering Properties can be Quantitatively Assessed In Vivo Using Diffuse Reflectance Spectroscopy. J Invest Dermatol; 117:1452-1457.
International Search Report and Written Opinion of the International Searching Authority, PCT/US2017/021843, dated Apr. 21, 2017.
S. Luecke et al., "The aryl hydrocarbon receptor (AHR), a novel regulator of human melanogenesis," Pigment Cell Melanoma Res. 23: 828-833 (2010).
CA Office Action for CA Application No. 3,017,352, dated Oct. 26, 2020, 3 pgs.
BR Office Action for Application No. BR112018068293-4, dated Oct. 1, 2021, 4 pgs.
English Translation (unofficial) of BR Office Action for Application No. BR112018068293-4, dated Oct. 1, 2021, 2 pgs.
AU First Examination Report for AU Application No. 2021232745, dated Dec. 5, 2022, 11 pgs.
CA Office Action for CA Application No. 3,017,352, dated Apr. 28, 2020, 4 pages.
CA Office Action for CA Application No. 3,017,352, dated May 5, 2022, 3 pages.
EP Office Action for EP Application No. 17711992.2, dated Nov. 25, 2019, 6 pages.
EP Office Action for EP Application No. 17711992.2, dated Jan. 3, 2022, 5 pages.
IL Office Action for IL Application No. 287141, dated Nov. 2, 2022, 4 pgs.
Kramer et al. (2005) "Malassezin, A Novel Agonist of the aryl hydrocarbon receptor from the yeast *Malassezia furfur*, induces apoptosis in primary human melanocytes," ChemBioChem; 6(5) 860-865.
Examination Report for EP Application No. 17711992.2 dated Jun. 23, 2023 (4 pages).
Examination Report for IN Application No. 201817037406 dated Nov. 26, 2019 (7 pages).
Examination Report for IN Application No. 202118021156 dated Feb. 8, 2022 (8 pages).
Examination Report for PH Application No. 1/2018/501926 dated Oct. 1, 2020 (4 pages).
Examination Report for PH Application No. 1/2018/501926 dated Aug. 13, 2021 (4 pages).
Examination Report No. 1 for AU Application No. 2017229970 dated Sep. 16, 2020 (8 pages).
Examination Report No. 2 for AU Application No. 2017229970 dated Sep. 14, 2021 (5 pages).
Examination Report No. 2 for AU Application No. 2021232745 dated Dec. 4, 2023 (3 pages).
Notice of Acceptance for AU Application No. 2017229970 dated Sep. 22, 2021 (3 pages).
Notice of Allowance for KR Application No. 10-2018-7029239 dated Apr. 22, 2021 (3 pages).
Notice of Reasons for Refusal for JP Application No. 2020-131521 dated May 2, 2022 (8 pages).
Written Opinion for SG Application No. 11201807730Q dated Apr. 12, 2021 (6 pages).
"Dimethyl Sulfoxide", Handbook of Pharmaceutical Excipients, Sixth Edition, Ed. Rowe R et al., Pharmaceutical Press and the American Pharmacists Association, 2009, pp. 238-240 (3 pages).

\* cited by examiner

1 – Inhibition of melanin synthesis – tyrosinase inhibition

2 – Inhibition of melanin transport to keratinocytes

3 – Apoptosis of melanocytes

Fig. 3A

| Compound ID | EC50 [nM] on MeWo | EC50 [nM] on WM115 |
|---|---|---|
| Staurosporine | 580.28 | 801.66 |
| CV-8684 | >10000 | >10000 |
| CV-8685 | >10000 | >10000 |
| CV-8686 | >10000 | >10000 |
| CV-8687 | >10000 | >10000 |
| CV-8688 | 908.57 | >10000 |

Fig. 4A

| Assay Time | MeWo Annexin V Dose | CV-8684 Relative Annexin V Level (%) | | | | WM115 Annexin V Dose | CV-8684 Relative Annexin V Level (%) | | | |
|---|---|---|---|---|---|---|---|---|---|---|
| | | n=1 | n=2 | Mean | STD | | n=1 | n=2 | Mean | STD |
| 6 hr | 100 | 255.88 | 282.35 | 269.12 | 18.72 | 100 | 124.91 | 153.90 | 139.41 | 20.50 |
| | 10 | 88.24 | 145.59 | 116.91 | 40.55 | 10 | 138.29 | 49.07 | 93.68 | 63.09 |
| | 1 | 136.76 | 158.82 | 147.79 | 15.60 | 1 | 104.83 | 111.52 | 108.18 | 4.73 |
| 24 hr | 100 | 95.89 | 72.14 | 84.02 | 16.80 | 100 | 106.24 | 116.06 | 111.15 | 6.94 |
| | 10 | 90.62 | 80.06 | 85.34 | 7.47 | 10 | 126.74 | 99.60 | 113.17 | 19.19 |
| | 1 | 87.98 | 42.23 | 65.10 | 32.35 | 1 | 121.83 | 106.24 | 114.04 | 11.02 |
| 48 hr | 100 | 125.45 | 105.45 | 115.45 | 14.14 | 100 | 23.31 | 29.97 | 26.64 | 4.71 |
| | 10 | 130.91 | 103.64 | 117.27 | 19.28 | 10 | 49.95 | 47.45 | 48.70 | 1.77 |
| | 1 | 74.55 | 54.55 | 64.55 | 14.14 | 1 | 74.09 | 67.43 | 70.76 | 4.71 |
| 72 hr | 100 | 30.94 | 8.84 | 19.89 | 15.63 | 100 | 55.13 | 59.27 | 57.20 | 2.93 |
| | 10 | 75.14 | 26.52 | 50.83 | 34.38 | 10 | 147.98 | 130.57 | 139.27 | 12.31 |
| | 1 | 39.78 | 66.30 | 53.04 | 18.75 | 1 | 113.99 | 118.13 | 116.06 | 2.93 |

Fig. 4B

| Assay Time | MeWo Annexin V Dose | CV-8685 Relative Annexin V Level (%) | | | | WM115 Annexin V Dose | CV-8685 Relative Annexin V Level (%) | | | |
|---|---|---|---|---|---|---|---|---|---|---|
| | | n=1 | n=2 | Mean | STD | | n=1 | n=2 | Mean | STD |
| 6 hr | 100 | 110.29 | 127.94 | 119.12 | 12.48 | 100 | 89.22 | 66.91 | 78.07 | 15.77 |
| | 10 | 202.94 | 101.47 | 152.21 | 71.75 | 10 | 149.44 | 75.84 | 112.64 | 52.05 |
| | 1 | 75.00 | 79.41 | 77.21 | 3.12 | 1 | 120.45 | 113.75 | 117.10 | 4.73 |
| 24 hr | 100 | 106.45 | 60.70 | 83.58 | 32.35 | 100 | 146.08 | 143.49 | 144.79 | 1.84 |
| | 10 | 146.04 | 112.61 | 129.33 | 23.64 | 10 | 133.38 | 106.53 | 119.96 | 18.99 |
| | 1 | 85.34 | 122.29 | 103.81 | 26.13 | 1 | 118.95 | 105.95 | 112.45 | 9.19 |
| 48 hr | 100 | 187.27 | 330.91 | 259.09 | 101.57 | 100 | 127.37 | 198.96 | 163.16 | 50.62 |
| | 10 | 107.27 | 214.55 | 160.91 | 75.85 | 10 | 125.70 | 54.94 | 90.32 | 50.03 |
| | 1 | 92.73 | 81.82 | 87.27 | 7.71 | 1 | 74.92 | 69.93 | 72.42 | 3.53 |
| 72 hr | 100 | 79.56 | 114.92 | 97.24 | 25.00 | 100 | 67.56 | 77.51 | 72.54 | 7.03 |
| | 10 | 88.40 | 83.98 | 86.19 | 3.13 | 10 | 106.11 | 112.75 | 109.43 | 4.69 |
| | 1 | 30.94 | 92.82 | 61.88 | 43.75 | 1 | 98.65 | 97.41 | 98.03 | 0.88 |

Fig. 4C

| Assay Time | MeWo Annexin V Dose | CV-8688 Relative Annexin V Level (%) | | | | WM115 Annexin V Dose | CV-8688 Relative Annexin V Level (%) | | | |
|---|---|---|---|---|---|---|---|---|---|---|
| | | n=1 | n=2 | Mean | STD | | n=1 | n=2 | Mean | STD |
| 6 hr | 100 | 123.53 | 145.59 | 134.56 | 15.60 | 100 | 180.67 | 194.05 | 187.36 | 9.46 |
| | 10 | 136.76 | 88.24 | 112.50 | 34.32 | 10 | 122.68 | 198.51 | 160.59 | 53.62 |
| | 1 | 92.65 | 70.59 | 81.62 | 15.60 | 1 | 89.22 | 140.52 | 114.87 | 36.28 |
| 24 hr | 100 | 36.95 | 13.20 | 25.07 | 16.80 | 100 | 17.32 | 15.59 | 16.46 | 1.22 |
| | 10 | 131.09 | 134.60 | 132.84 | 2.49 | 10 | 99.31 | 105.09 | 102.20 | 4.08 |
| | 1 | 144.28 | 95.03 | 119.65 | 34.84 | 1 | 114.90 | 66.40 | 90.65 | 34.30 |
| 48 hr | 100 | 85.45 | 69.09 | 77.27 | 11.57 | 100 | 14.15 | 7.49 | 10.82 | 4.71 |
| | 10 | 94.55 | 130.91 | 112.73 | 25.71 | 10 | 89.07 | 120.71 | 104.89 | 22.37 |
| | 1 | 120.00 | 90.91 | 105.45 | 20.57 | 1 | 130.70 | 125.70 | 128.20 | 3.53 |
| 72 hr | 100 | 66.30 | 44.20 | 55.25 | 15.63 | 100 | 2.49 | 1.66 | 2.07 | 0.59 |
| | 10 | 66.30 | 110.50 | 88.40 | 31.25 | 10 | 108.19 | 114.40 | 111.30 | 4.40 |
| | 1 | 70.72 | 66.30 | 68.51 | 3.13 | 1 | 96.99 | 113.99 | 105.49 | 12.02 |

Fig. 4D

| Assay Time | MeWo Annexin V Dose | Staurosporine Relative Annexin V Level (%) | | | | WM115 Annexin V Dose | Staurosporine Relative Annexin V Level (%) | | | |
|---|---|---|---|---|---|---|---|---|---|---|
| | | n=1 | n=2 | Mean | STD | | n=1 | n=2 | Mean | STD |
| 6 hr | 10 | 377.03 | 218.92 | 297.97 | 111.80 | 10 | 124.91 | 129.37 | 127.14 | 3.15 |
| 24 hr | 10 | 29.03 | 37.83 | 33.43 | 6.22 | 10 | 5.77 | 17.90 | 11.84 | 8.57 |
| 48 hr | 10 | 9.09 | 7.27 | 8.18 | 1.29 | 10 | 7.49 | 6.66 | 7.08 | 0.59 |
| 72 hr | 10 | 44.20 | 26.52 | 35.36 | 12.50 | 10 | 3.32 | 1.24 | 2.28 | 1.47 |

Fig. 13A

| | MeWo | CV-8684 | | | | WM115 | CV-8684 | | | |
| | CTG | Remaining cell viability (%) | | | | CTG | Remaining cell viability (%) | | | |
| Assay Time | Dose | n=1 | n=2 | Mean | STD | Dose | n=1 | n=2 | Mean | STD |
|---|---|---|---|---|---|---|---|---|---|---|
| 6 hr | 100 | 34.50 | 32.55 | 33.52 | 1.38 | 100 | 62.71 | 45.31 | 54.01 | 12.30 |
| | 10 | 102.35 | 106.61 | 104.48 | 3.02 | 10 | 96.60 | 94.06 | 95.33 | 1.79 |
| | 1 | 101.49 | 95.16 | 98.33 | 4.47 | 1 | 102.04 | 103.31 | 102.67 | 0.90 |
| 24 hr | 100 | 52.20 | 49.76 | 50.98 | 1.73 | 100 | 65.85 | 62.96 | 64.40 | 2.04 |
| | 10 | 90.73 | 83.62 | 87.18 | 5.03 | 10 | 92.21 | 88.80 | 90.51 | 2.41 |
| | 1 | 93.70 | 88.36 | 91.03 | 3.77 | 1 | 99.16 | 95.49 | 97.33 | 2.60 |
| 48 hr | 100 | 49.17 | 47.86 | 48.52 | 0.93 | 100 | 42.46 | 32.16 | 37.31 | 7.28 |
| | 10 | 59.57 | 62.18 | 60.87 | 1.84 | 10 | 84.08 | 73.57 | 78.82 | 7.43 |
| | 1 | 76.02 | 71.82 | 73.92 | 2.97 | 1 | 98.16 | 90.59 | 94.38 | 5.35 |
| 72 hr | 100 | 27.45 | 23.17 | 25.31 | 3.02 | 100 | 42.63 | 39.39 | 41.01 | 2.29 |
| | 10 | 38.51 | 35.78 | 37.14 | 1.93 | 10 | 112.60 | 110.28 | 111.44 | 1.64 |
| | 1 | 57.32 | 60.65 | 58.99 | 2.36 | 1 | 127.43 | 116.77 | 122.10 | 7.54 |

Fig. 13B

| Assay Time | MeWo CTG Dose | CV-8685 Remaining cell viability (%) | | | | WM115 CTG Dose | CV-8685 Remaining cell viability (%) | | | |
|---|---|---|---|---|---|---|---|---|---|---|
| | | n=1 | n=2 | Mean | STD | | n=1 | n=2 | Mean | STD |
| 6 hr | 100 | 75.16 | 79.98 | 77.57 | 3.40 | 100 | 89.53 | 90.26 | 89.90 | 0.51 |
| | 10 | 98.08 | 98.08 | 98.08 | 0.00 | 10 | 100.41 | 96.60 | 98.50 | 2.69 |
| | 1 | 98.65 | 95.79 | 97.22 | 2.02 | 1 | 99.14 | 98.96 | 99.05 | 0.13 |
| 24 hr | 100 | 87.18 | 91.92 | 89.55 | 3.35 | 100 | 65.58 | 62.31 | 63.94 | 2.32 |
| | 10 | 94.89 | 93.11 | 94.00 | 1.26 | 10 | 87.49 | 87.10 | 87.29 | 0.28 |
| | 1 | 90.14 | 88.36 | 89.25 | 1.26 | 1 | 94.70 | 92.74 | 93.72 | 1.39 |
| 48 hr | 100 | 100.26 | 94.13 | 97.19 | 4.33 | 100 | 57.17 | 57.80 | 57.49 | 0.45 |
| | 10 | 80.59 | 80.21 | 80.40 | 0.27 | 10 | 85.34 | 82.61 | 83.97 | 1.93 |
| | 1 | 97.07 | 92.52 | 94.80 | 3.22 | 1 | 97.32 | 96.06 | 96.69 | 0.89 |
| 72 hr | 100 | 73.74 | 65.54 | 69.64 | 5.80 | 100 | 75.99 | 67.19 | 71.59 | 6.23 |
| | 10 | 69.51 | 69.56 | 69.53 | 0.04 | 10 | 108.89 | 101.01 | 104.95 | 5.57 |
| | 1 | 61.97 | 66.74 | 64.35 | 3.37 | 1 | 122.79 | 118.16 | 120.47 | 3.28 |

Fig. 13C

| Assay Time | MeWo CTG Dose | CV-8688 Remaining cell viability (%) | | | | WM115 CTG Dose | CV-8688 Remaining cell viability (%) | | | |
|---|---|---|---|---|---|---|---|---|---|---|
| | | n=1 | n=2 | Mean | STD | | n=1 | n=2 | Mean | STD |
| 6 hr | 100 | 3.33 | 2.70 | 3.02 | 0.45 | 100 | 63.25 | 42.41 | 52.83 | 14.74 |
| | 10 | 108.32 | 93.82 | 101.07 | 10.25 | 10 | 96.78 | 95.51 | 96.15 | 0.90 |
| | 1 | 101.76 | 94.50 | 98.13 | 5.13 | 1 | 97.87 | 99.50 | 98.69 | 1.15 |
| 24 hr | 100 | 9.91 | 8.85 | 9.38 | 0.74 | 100 | 4.32 | 2.25 | 3.29 | 1.47 |
| | 10 | 96.07 | 91.92 | 94.00 | 2.94 | 10 | 92.08 | 91.16 | 91.62 | 0.65 |
| | 1 | 88.36 | 99.63 | 94.00 | 7.97 | 1 | 91.56 | 93.00 | 92.28 | 1.02 |
| 48 hr | 100 | 1.01 | 0.75 | 0.88 | 0.18 | 100 | 1.05 | 0.78 | 0.91 | 0.19 |
| | 10 | 70.14 | 66.56 | 68.35 | 2.53 | 10 | 91.85 | 88.91 | 90.38 | 2.08 |
| | 1 | 83.54 | 76.01 | 79.78 | 5.33 | 1 | 97.95 | 97.95 | 97.95 | 0.00 |
| 72 hr | 100 | 0.90 | 0.72 | 0.81 | 0.13 | 100 | 2.53 | 2.33 | 2.43 | 0.14 |
| | 10 | 54.30 | 52.34 | 53.32 | 1.38 | 10 | 113.52 | 106.57 | 110.05 | 4.91 |
| | 1 | 79.95 | 67.49 | 73.72 | 8.81 | 1 | 122.79 | 118.62 | 120.71 | 2.95 |

Fig. 13D

| Assay Time | MeWo CTG Dose | Staurosporine Remaining cell viability (%) | | | | WM115 CTG Dose | Staurosporine Remaining cell viability (%) | | | |
|---|---|---|---|---|---|---|---|---|---|---|
| | | n=1 | n=2 | Mean | STD | | n=1 | n=2 | Mean | STD |
| 6 hr | 10 | 33.39 | 53.30 | 43.34 | 14.08 | 10 | 55.46 | 51.29 | 53.38 | 2.95 |
| 24 hr | 10 | 6.94 | 2.53 | 4.73 | 3.11 | 10 | 1.29 | 1.16 | 1.23 | 0.09 |
| 48 hr | 10 | 0.84 | 0.61 | 0.73 | 0.16 | 10 | 0.54 | 0.55 | 0.55 | 0.00 |
| 72 hr | 10 | 0.62 | 0.63 | 0.63 | 0.01 | 10 | 2.65 | 2.78 | 2.71 | 0.09 |

Fig. 13K

| Compound | Cell viability (% viable cells) | | | | | |
|---|---|---|---|---|---|---|
| | MeWo cell line | | | WM115 cell line | | |
| | 24h | 48h | 72h | 24h | 48h | 72h |
| Malassezin (100 uM) | 51% | 49% | 25% | 64% | 37% | 41% |
| Indolocarbazole (100 uM) | 90% | 97% | 70% | 64% | 57% | 72% |
| Compound II (100 uM) | 9% | 1% | 1% | 3% | 1% | 2% |
| Staurosporin (10 uM) PC | 5% | 1% | 1% | 1% | 1% | 3% |

Fig. 14A

| Assay Time | MeWo LDH Dose | CV-8684 LDH Level (%) | | | | WM115 LDH Dose | CV-8684 LDH Level (%) | | | |
|---|---|---|---|---|---|---|---|---|---|---|
| | | n=1 | n=2 | Mean | STD | | n=1 | n=2 | Mean | STD |
| 6 hr | 100 | 107.53 | 88.80 | 98.17 | 13.25 | 100 | 105.30 | 107.71 | 106.50 | 1.71 |
| | 10 | 99.34 | 93.34 | 96.34 | 4.24 | 10 | 88.26 | 93.07 | 90.67 | 3.40 |
| | 1 | 100.67 | 93.76 | 97.22 | 4.89 | 1 | 95.04 | 88.86 | 91.95 | 4.37 |
| 24 hr | 100 | 128.00 | 113.06 | 120.53 | 10.56 | 100 | 137.11 | 110.90 | 124.00 | 18.53 |
| | 10 | 104.34 | 91.17 | 97.75 | 9.31 | 10 | 111.28 | 108.83 | 110.06 | 1.73 |
| | 1 | 116.42 | 104.79 | 110.61 | 8.22 | 1 | 109.44 | 113.59 | 111.52 | 2.94 |
| 48 hr | 100 | 108.45 | 129.84 | 119.14 | 15.12 | 100 | 141.09 | 120.98 | 131.04 | 14.21 |
| | 10 | 112.21 | 119.13 | 115.67 | 4.89 | 10 | 71.47 | 105.67 | 88.57 | 24.18 |
| | 1 | 114.69 | 112.52 | 113.60 | 1.53 | 1 | 87.84 | 108.38 | 98.11 | 14.52 |
| 72 hr | 100 | 88.08 | 86.69 | 87.39 | 0.98 | 100 | 172.24 | 145.78 | 159.01 | 18.71 |
| | 10 | 89.41 | 85.17 | 87.29 | 3.00 | 10 | 134.39 | 125.37 | 129.88 | 6.38 |
| | 1 | 83.42 | 75.05 | 79.24 | 5.91 | 1 | 155.11 | 144.29 | 149.70 | 7.65 |

Fig. 14B

| Assay Time | MeWo LDH Dose | CV-8685 LDH Level (%) | | | | WM115 LDH Dose | CV-8685 LDH Level (%) | | | |
|---|---|---|---|---|---|---|---|---|---|---|
| | | n=1 | n=2 | Mean | STD | | n=1 | n=2 | Mean | STD |
| 6 hr | 100 | 94.68 | 89.90 | 92.29 | 3.38 | 100 | 91.36 | 80.17 | 85.76 | 7.91 |
| | 10 | 85.58 | 92.47 | 89.03 | 4.87 | 10 | 94.90 | 95.37 | 95.14 | 0.33 |
| | 1 | 92.44 | 92.44 | 92.44 | 0.01 | 1 | 87.67 | 95.81 | 91.74 | 5.76 |
| 24 hr | 100 | 142.99 | 104.54 | 123.76 | 27.19 | 100 | 213.02 | 234.98 | 224.00 | 15.53 |
| | 10 | 92.63 | 89.87 | 91.25 | 1.95 | 10 | 150.57 | 137.26 | 143.91 | 9.41 |
| | 1 | 101.78 | 105.21 | 103.49 | 2.43 | 1 | 94.63 | 109.59 | 102.11 | 10.58 |
| 48 hr | 100 | 125.18 | 122.77 | 123.97 | 1.70 | 100 | 222.63 | 224.48 | 223.55 | 1.30 |
| | 10 | 108.43 | 111.15 | 109.79 | 1.92 | 10 | 143.57 | 113.47 | 128.52 | 21.28 |
| | 1 | 114.41 | 112.82 | 113.62 | 1.12 | 1 | 86.50 | 105.02 | 95.76 | 13.10 |
| 72 hr | 100 | 88.24 | 56.05 | 72.14 | 22.76 | 100 | 262.72 | 259.96 | 261.34 | 1.95 |
| | 10 | 72.96 | 72.35 | 72.66 | 0.43 | 10 | 175.23 | 171.15 | 173.19 | 2.89 |
| | 1 | 77.93 | 74.86 | 76.40 | 2.17 | 1 | 147.09 | 146.42 | 146.75 | 0.47 |

Fig. 14C

| Assay Time | MeWo LDH Dose | CV-8688 LDH Level (%) | | | | WM115 LDH Dose | CV-8688 LDH Level (%) | | | |
| --- | --- | --- | --- | --- | --- | --- | --- | --- | --- | --- |
| | | n=1 | n=2 | Mean | STD | | n=1 | n=2 | Mean | STD |
| 6 hr | 100 | 127.34 | 101.13 | 114.23 | 18.53 | 100 | 113.29 | 126.97 | 120.13 | 9.68 |
| | 10 | 89.41 | 84.00 | 86.70 | 3.82 | 10 | 95.94 | 90.02 | 92.98 | 4.18 |
| | 1 | 92.90 | 92.24 | 92.57 | 0.47 | 1 | 93.07 | 89.66 | 91.36 | 2.41 |
| 24 hr | 100 | 180.63 | 150.41 | 165.52 | 21.37 | 100 | 406.53 | 379.09 | 392.81 | 19.41 |
| | 10 | 103.64 | 99.45 | 101.55 | 2.96 | 10 | 115.00 | 102.91 | 108.96 | 8.55 |
| | 1 | 104.70 | 103.26 | 103.98 | 1.02 | 1 | 99.80 | 113.95 | 106.87 | 10.00 |
| 48 hr | 100 | 142.36 | 143.69 | 143.03 | 0.94 | 100 | 240.09 | 276.78 | 258.43 | 25.95 |
| | 10 | 97.14 | 103.68 | 100.41 | 4.63 | 10 | 71.88 | 98.21 | 85.04 | 18.62 |
| | 1 | 107.03 | 111.80 | 109.42 | 3.37 | 1 | 91.02 | 93.94 | 92.48 | 2.07 |
| 72 hr | 100 | 104.85 | 111.78 | 108.32 | 4.90 | 100 | 262.85 | 264.08 | 263.47 | 0.87 |
| | 10 | 72.51 | 79.43 | 75.97 | 4.89 | 10 | 108.06 | 111.37 | 109.71 | 2.34 |
| | 1 | 78.39 | 75.68 | 77.03 | 1.91 | 1 | 148.60 | 143.38 | 145.99 | 3.69 |

Fig. 14D

| Assay Time | MeWo LDH Dose | Staurosporine LDH Level (%) | | | | WM115 LDH Dose | Staurosporine LDH Level (%) | | | |
|---|---|---|---|---|---|---|---|---|---|---|
| | | n=1 | n=2 | Mean | STD | | n=1 | n=2 | Mean | STD |
| 6 hr | 10 | 80.82 | 93.35 | 87.09 | 8.86 | 100 | 96.35 | 101.90 | 99.13 | 3.92 |
| 24 hr | 10 | 243.09 | 212.50 | 227.80 | 21.63 | 100 | 394.99 | 371.77 | 383.38 | 16.42 |
| 48 hr | 10 | 170.60 | 171.35 | 170.98 | 0.53 | 100 | 207.76 | 185.08 | 196.42 | 16.04 |
| 72 hr | 10 | 114.91 | 122.19 | 118.55 | 5.15 | 100 | 158.74 | 233.56 | 196.15 | 52.91 |

Fig. 15F

| Cpds Code | Compound ID | EC50(uM) |
|---|---|---|
| PC | Omeprazole | 51.01 |
| Cpd01 | CV-8684 | 4.39 |
| Cpd02 | CV-8685 | 2.80 |
| Cpd03 | CV-8686 | 3.13 |
| Cpd04 | CV-8688 | 16.41 |

Controls

Day 0      Day 7

Untreated tissues    Negative Control (sterile deionized water)-treated tissues

A  B

Positive Control (1% Kojic Acid) treated tissues

C

Vehicle Control (DMSO)-treated tissues
D   0.2%     E   0.05%

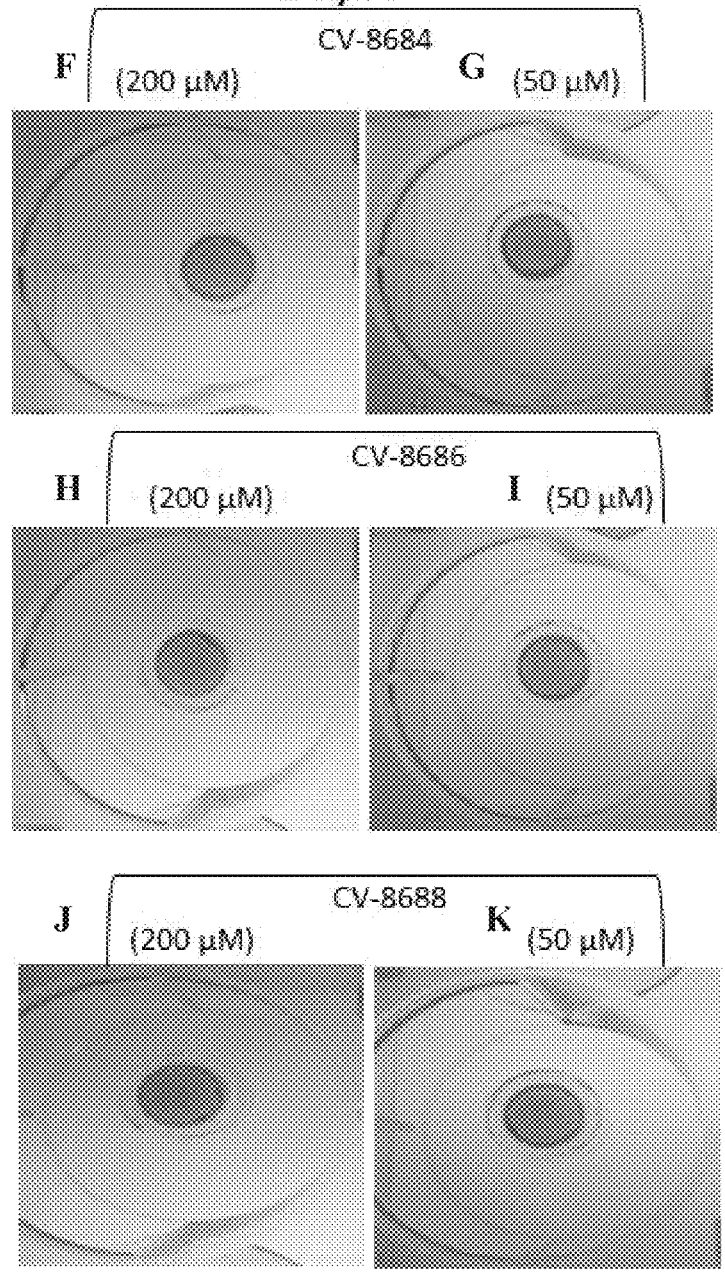

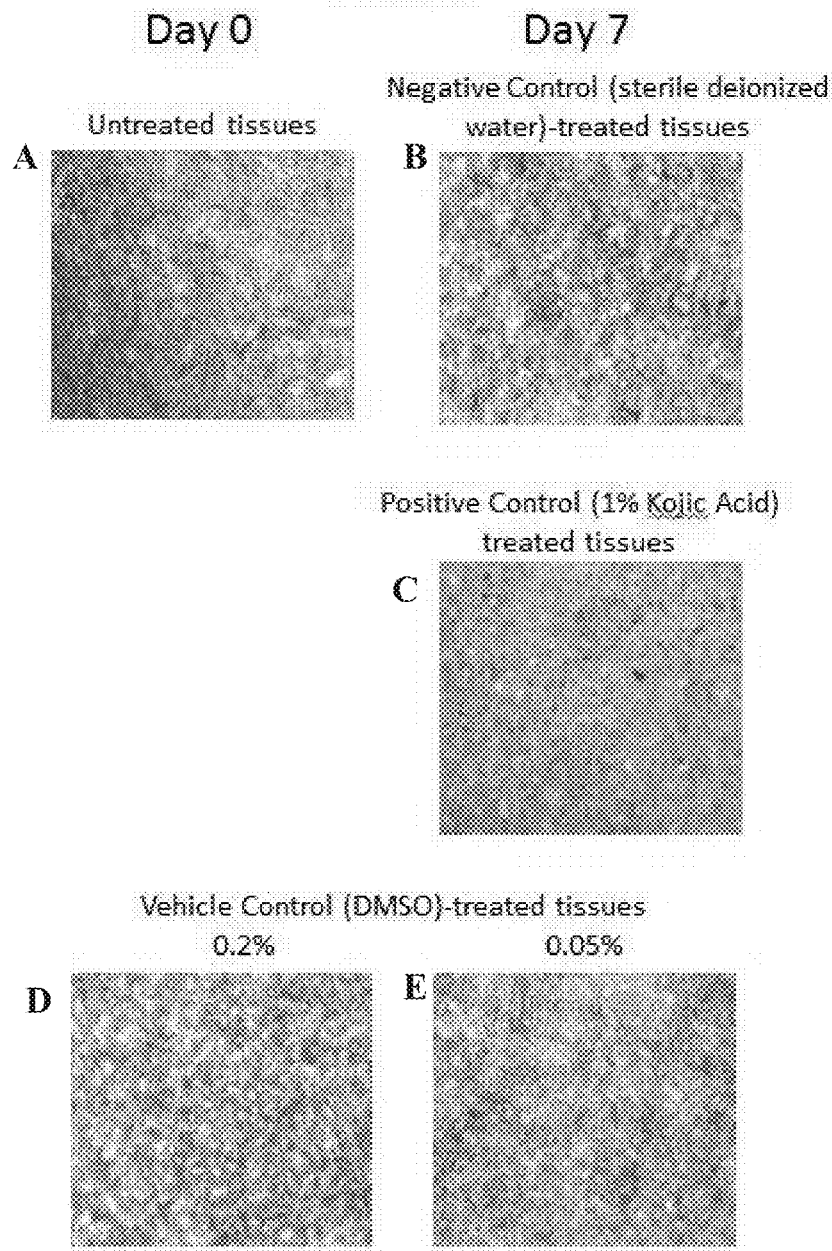

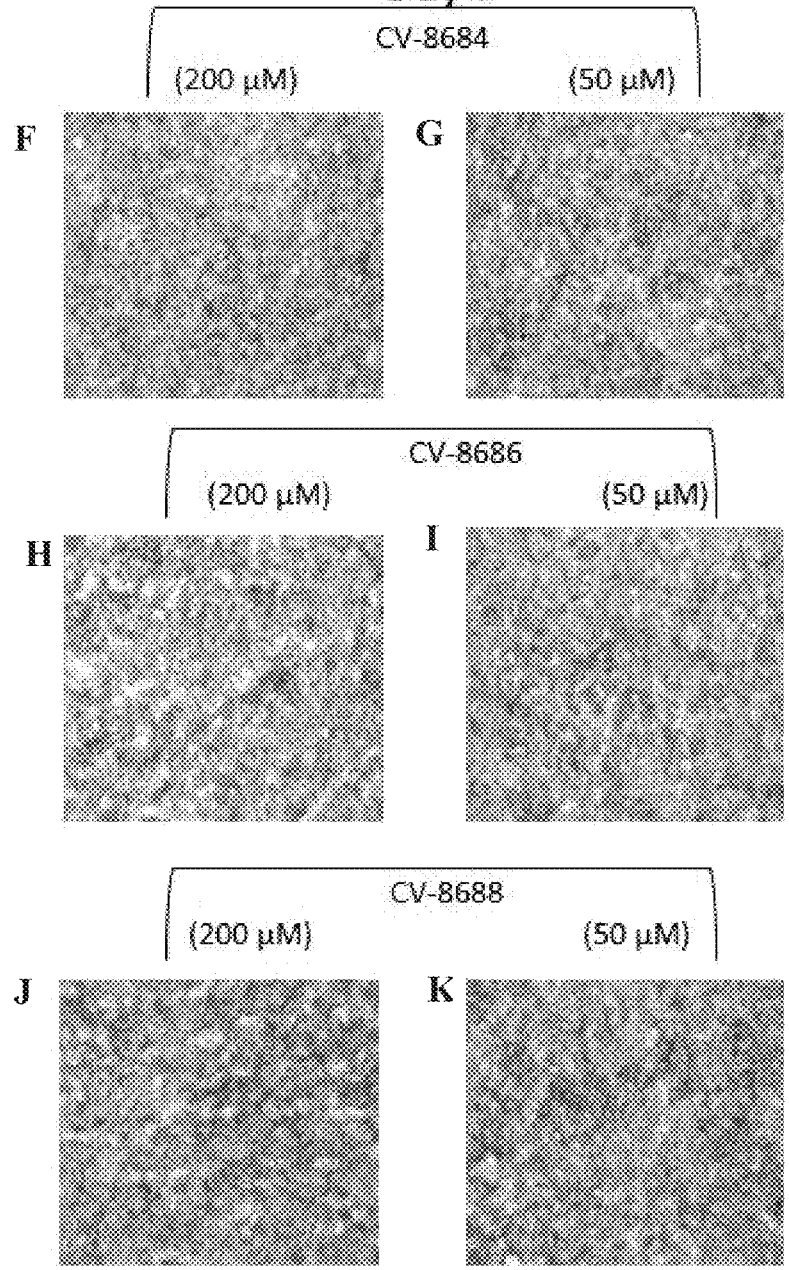

Fig. 20

| Condition | Number of zebrafish with decreased skin pigmentation | | | | % Zebrafish with decreased skin pigmentation |
|---|---|---|---|---|---|
| | Well 1 | Well 2 | Well 3 | Total | |
| Untreated | 1 | 0 | 0 | 1 | 3.3 |
| DMSO | 1 | 0 | 0 | 1 | 3.3 |
| 0.003% PTU | 10 | 10 | 10 | 30 | 100.0 |
| 0.3 uM | 0 | 3 | 0 | 3 | 10.0 |
| 1 uM | 2 | 6 | 7 | 15 | 50.0 |
| 2.5 uM | 9 | 10 | 10 | 29 | 96.7 |
| 3 uM | 9 | 7 | 7 | 23 | 76.7 |
| 5 uM | 7 | 5 | 8 | 20 | 66.7 |
| 10 uM | 1 | 0 | 0 | 1 | 3.3 |

Fig. 23J

| Compound | Medium | Conc (uM) | Incubation time (hr) | ID | Chromatogram | | |
|---|---|---|---|---|---|---|---|
| | | | | | Ret. Time | Area | Remaining % |
| CV-8684 | DMSO | 100 | 2 | 1 | 2.65 | 576025.00 | 100.00 |
| | RPMI | 100 | 2 | 2 | 1.25 | 538008.00 | 93.40 |
| | DMEM | 100 | 2 | 3 | 1.24 | 618641.00 | 107.40 |
| CV-8686 | DMSO | 100 | 2 | 4 | 1.49 | 928029.00 | 100.00 |
| | RPMI | 100 | 2 | 5 | 1.49 | 924480.00 | 99.62 |
| | DMEM | 100 | 2 | 6 | 1.49 | 898129.00 | 96.78 |
| CV-8688 | DMSO | 100 | 2 | 7 | 1.29 | 313314.00 | 100.00 |
| | RPMI | 100 | 2 | 8 | 1.31 | 333242.00 | 106.36 |
| | DMEM | 100 | 2 | 9 | 1.30 | 340709.00 | 108.74 |

MALASSEZIN AND ANALOGS THEREOF AS SKIN BRIGHTENING AGENTS

CROSS-REFERENCE TO RELATED APPLICATIONS

This application is a divisional application of U.S. non-provisional application Ser. No. 16/121,353, filed on Sep. 4, 2018, which is a divisional application of U.S. non-provisional application Ser. No. 15/455,932, filed on Mar. 10, 2017, which claims the benefit of U.S. provisional application Ser. No. 62/306,468, filed Mar. 10, 2016. The entire contents of the above-referenced applications are hereby incorporated by reference herein.

FIELD OF INVENTION

The present invention relates to chemical analogs of compounds produced by a *Malassezia* yeast. The invention includes compositions comprising compounds produced by a *Malassezia* yeast as well as chemical analogs of compounds produced by a *Malassezia* yeast. Methods of using the compounds (including analogs thereof) and compositions of the present invention are also contemplated.

BACKGROUND OF THE INVENTION

Individuals around the world use skin brightening agents to achieve a number of cosmetic goals, including producing an anti-aging effect, correcting sun damage, and meeting certain cultural standards of beauty. Many commercially available skin brightening products, while effective to varying degrees, contain harmful ingredients, some of which have been linked to cancer. Thus, there exists a need for novel skin brightening agents and formulations that exhibit higher levels of safety and/or efficacy than agents currently on the market.

*Malassezia* is a genus of lipophilic yeast commonly found in the normal flora of human skin. *Malassezia* is responsible for a number of skin diseases, including tinea versicolor (pityriasis versicolor), seborrheic dermatitis, and atopic dermatitis.

Tinea versicolor is a non-contagious skin disease caused by *Malassezia* overgrowth that locally alters pigmentation levels. *Malassezia* yeasts have two metabolic pathways for synthesizing melanin and tryptophan-derived indole pigments. The indole pigments include malassezin, a tryptophan metabolite of *Malassezia* that may elicit melanocyte apoptosis and contribute to the depigmentation characteristic of *Malassezia* overgrowth.

The invention disclosed herein utilizes compounds produced by *Malassezia* yeast, including malassezin, and chemical analogs thereof, as the basis for safe and efficacious skin brightening compositions.

SUMMARY OF THE INVENTION

One embodiment of the present invention is a compound for brightening skin. The compound is a chemical analog of a compound produced by a *Malassezia* yeast, or a crystalline form, hydrate, or cosmetically or pharmaceutically acceptable salt thereof.

Another embodiment of the present invention is a compound for inducing melanocyte apoptosis. The compound is a chemical analog of a compound produced by a *Malassezia* yeast, or a crystalline form, hydrate, or cosmetically or pharmaceutically acceptable salt thereof.

A further embodiment of the present invention is a compound for modulating melanocyte activity. The compound is a chemical analog of a compound produced by a *Malassezia* yeast, or a crystalline form, hydrate, or cosmetically or pharmaceutically acceptable salt thereof.

An additional embodiment of the present invention is a compound for agonizing the arylhydrocarbon receptor (AhR). The compound is a chemical analog of a compound produced by a *Malassezia* yeast, or a crystalline form, hydrate, or cosmetically or pharmaceutically acceptable salt thereof.

Another embodiment of the present invention is a compound for improving hyperpigmentation caused by a hyperpigmentation disorder. The compound is a chemical analog of a compound produced by a *Malassezia* yeast, or a crystalline form, hydrate, or cosmetically or pharmaceutically acceptable salt thereof.

A further embodiment of the present invention is a compound for modulating melanin production. The compound is a chemical analog of a compound produced by a *Malassezia* yeast, or a crystalline form, hydrate, or cosmetically or pharmaceutically acceptable salt thereof.

An additional embodiment of the present invention is a compound for modulating melanosome biogenesis. The compound is a chemical analog of a compound produced by a *Malassezia* yeast, or a crystalline form, hydrate, or cosmetically or pharmaceutically acceptable salt thereof.

Another embodiment of the present invention is a compound for modulating melanosome transfer. The compound is a chemical analog of a compound produced by a *Malassezia* yeast, or a crystalline form, hydrate, or cosmetically or pharmaceutically acceptable salt thereof.

A further embodiment of the present invention is a composition. The composition comprises a *Malassezia* yeast and a cosmetically or pharmaceutically acceptable vehicle, diluent or carrier.

An additional embodiment of the present invention is a composition. The composition comprises a compound isolated or isolatable from a *Malassezia* yeast and a cosmetically or pharmaceutically acceptable vehicle, diluent or carrier.

Another embodiment of the present invention is a composition. The composition comprises any of the compounds, including analogs, disclosed herein and a cosmetically or pharmaceutically acceptable vehicle, diluent or carrier.

A further embodiment of the present invention is a method of brightening skin in a subject. The method comprises contacting the subject with any of the compounds or compositions disclosed herein.

An additional embodiment of the present invention is a method for inducing melanocyte apoptosis in a subject. The method comprises contacting the subject with any of the compounds or compositions disclosed herein.

Another embodiment of the present invention is a method for modulating melanocyte activity in a subject. The method comprises contacting the subject with any of the compounds or compositions disclosed herein.

A further embodiment of the present invention is a method for agonizing an arylhydrocarbon receptor (AhR) in a subject. The method comprises contacting the subject with any of the compounds or compositions disclosed herein.

An additional embodiment of the present invention is a method for improving hyperpigmentation caused by a hyperpigmentation disorder in a subject in need thereof. The method comprises contacting the subject with any of the compounds or compositions disclosed herein.

Another embodiment of the present invention is a method for modulating melanin production in a subject. The method comprises contacting the subject with any of the compounds or compositions disclosed herein.

A further embodiment of the present invention is a method for modulating melanosome biogenesis in a subject. The method comprises contacting the subject with any of the compounds or compositions disclosed herein.

An additional embodiment of the present invention is a method for modulating melanosome transfer in a subject. The method comprises contacting the subject with any of the compounds or compositions disclosed herein.

Another embodiment of the present invention is a compound. The compound has the structure of formula (II):

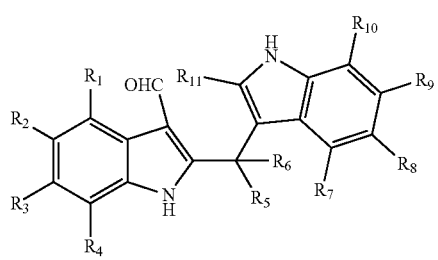

wherein:

R1, R2, R3, R4, R5, R6, R7, R8, R9, R10, and R11 are independently selected from the group consisting of hydrogen and methyl, and at least one of R1, R2, R3, R4, R5, R6, R7, R8, R9, R10 and R11 is methyl; or a crystalline form, hydrate, or cosmetically or pharmaceutically acceptable salt thereof.

A further embodiment of the present invention is a compound. The compound has the structure of formula (III):

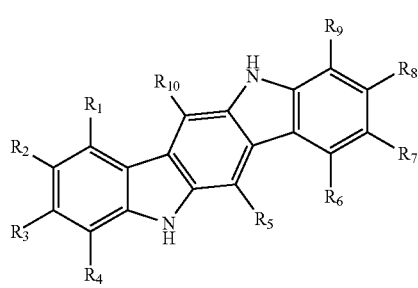

wherein: R1, R2, R3, R4, R5, R6, R7, R8, R9, and R10 are independently selected from the group consisting of hydrogen and methyl, and at least one of R1, R2, R3, R4, R5, R6, R7, R8, R9, and R10 is methyl; or a crystalline form, hydrate, or cosmetically or pharmaceutically acceptable salt thereof.

An additional embodiment of the present invention is a compound for brightening skin. The compound has the structure of formula (II):

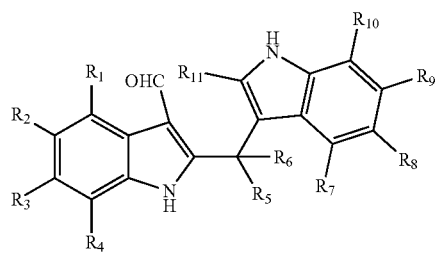

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

Another embodiment of the present invention is a compound for brightening skin. The compound has the structure of formula (III):

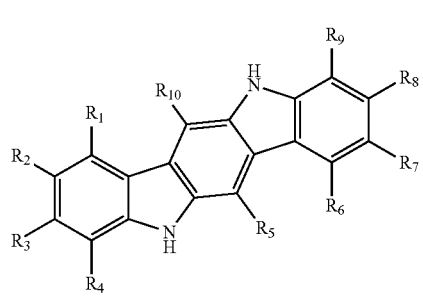

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

A further embodiment of the present invention is a compound for inducing melanocyte apoptosis. The compound has the structure of formula (II):

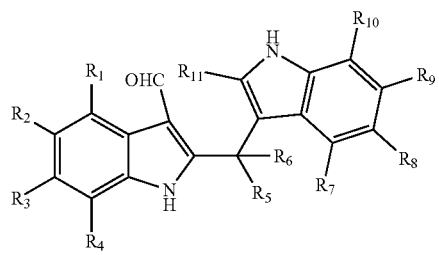

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

An additional embodiment of the present invention is a compound for inducing melanocyte apoptosis. The compound has the structure of formula (III):

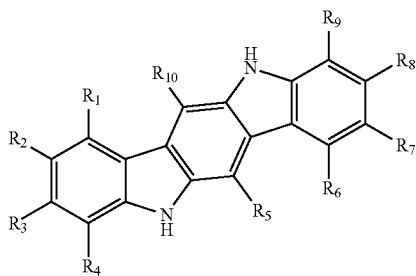
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

Another embodiment of the present invention is a compound for agonizing the arylhydrocarbon receptor (AhR). The compound has the structure of formula (II):

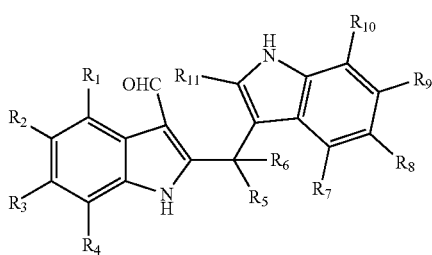
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

A further embodiment of the present invention is a compound for agonizing the arylhydrocarbon receptor (AhR). The compound has the structure of formula (III):

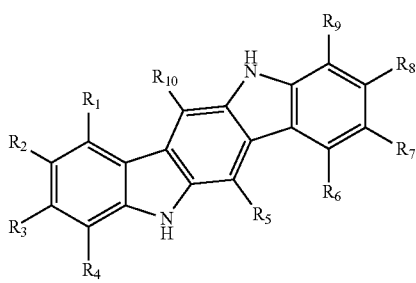
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

An additional embodiment of the present invention is a composition. The composition comprises a compound having the structure of formula (II):

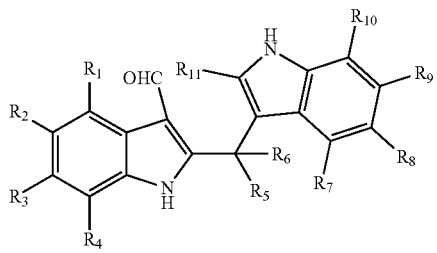
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

Another embodiment of the present invention is a composition. The composition comprises a compound having the structure of formula (III):

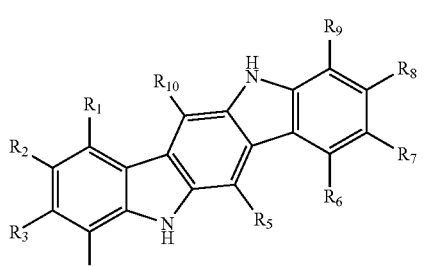
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

A further embodiment of the present invention is a method for brightening skin in a subject. The method comprises: contacting the subject with a compound having the structure of formula (II):

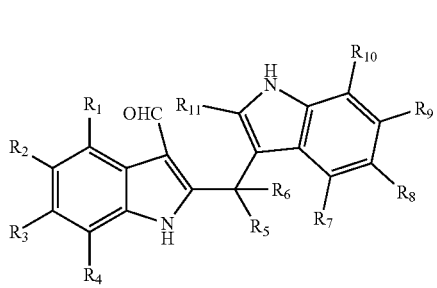
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

An additional embodiment of the present invention is a method for brightening skin in a subject. The method comprises: contacting the subject with a compound having the structure of formula (III):

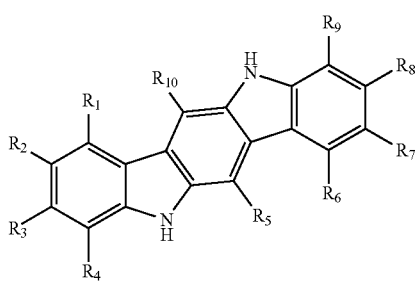

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

Another embodiment of the present invention is a method for inducing melanocyte apoptosis in a subject. The method comprises: contacting the subject with a compound having the structure of formula (II):

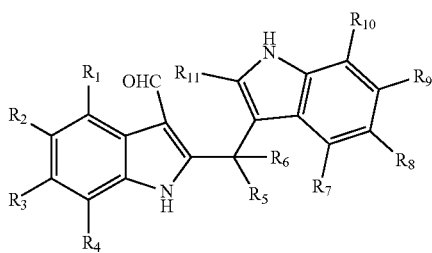

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

A further embodiment of the present invention is a method for inducing melanocyte apoptosis in a subject. The method comprises: contacting the subject with a compound having the structure of formula (III):

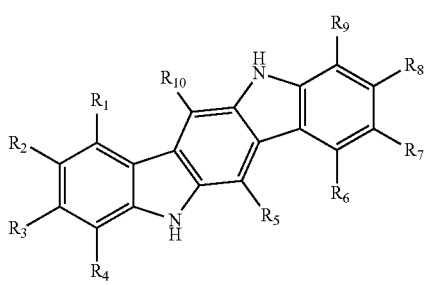

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

Another embodiment of the present invention is a method for agonizing an arylhydrocarbon receptor (AhR) in a subject. The method comprises: contacting a subject with a compound having the structure of formula (II):

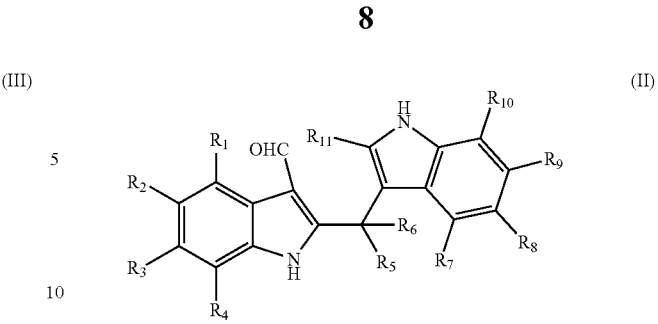

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

A further embodiment of the present invention is a method for agonizing an arylhydrocarbon receptor (AhR) in a subject. The method comprises: contacting the subject with a compound having the structure of formula (III):

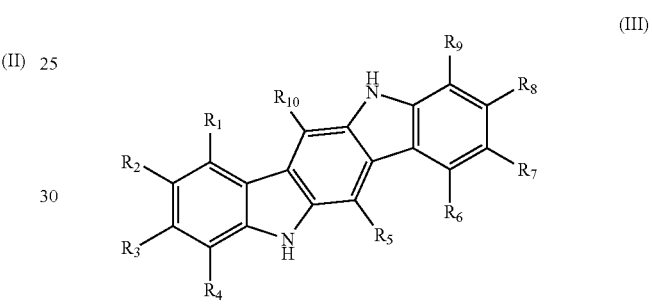

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A: malassezin and indolo[3,2-b] carbazole; FIG. 2B: compounds I and IV; FIG. 2C: compound II.

FIG. 3A is a summary chart showing $EC_{50}$ values of annexin V induction for certain compounds of the present invention in MeWo and WM115 cells.

FIGS. 4A-4D are charts showing relative annexin V levels (%) in MeWo and WM115 cells after exposure to various concentrations of the listed compounds for 6, 24, 48, and 72 hours.

FIGS. 13A-13D are charts showing the percentage of viable MeWo and WM115 cells remaining after treatment with various concentrations of CV-8684 (FIG. 13A), CV-8685 (FIG. 13B), CV-8688 (FIG. 13C), or staurosporine (FIG. 13D) for 6, 24, 48, and 72 hours. Cell viability was assayed using CellTiter-Glo®.

FIG. 13K is a summary chart comparing percentages of viable MeWo and WM115 cells after exposure to the listed concentrations of malassezin, indolocarbazole, compound II, and staurosporine for 24, 48, and 72 hours.

FIGS. 14A-14D are charts showing levels of lactate dehydrogenase ("LDH") release from MeWo and WM115 cells after treatment with various concentrations of CV-8684 (FIG. 14A), CV-8685 (FIG. 14B), CV-8688 (FIG. 14C), or staurosporine (FIG. 14D) for 6, 24, 48, and 72 hours.

FIG. 15F shows $EC_{50}$ values for each compound tested.

FIGS. 16A-16K are photographs of MelanoDerm™ matrices at either day 0 or day 7 after exposure to no treatment (FIG. 16A), sterile deionized water (FIG. 16B), 1% kojic acid (FIG. 16C), 0.2% DMSO (FIG. 16D), 0.05% DMSO (FIG. 16E), 200 µM CV-8684 (FIG. 16F), 50 µM CV-8684 (FIG. 16G), 200 µM CV-8686 (FIG. 16H), 50 µM CV-8686 (FIG. 16I), 200 µM CV-8688 (FIG. 16J), and 50 µM CV-8688 (FIG. 16K).

FIGS. 17A-17K are 15× magnification photomicrographs of MelanoDerm™ matrices at either day 0 or day 7 after exposure to no treatment (FIG. 17A), sterile deionized water (FIG. 17B), 1% kojic acid (FIG. 17C), 0.2% DMSO (FIG. 17D), 0.05% DMSO (FIG. 17E), 200 µM CV-8684 (FIG. 17F), 50 µM CV-8684 (FIG. 17G), 200 µM CV-8686 (FIG. 17H), 50 µM CV-8686 (FIG. 17I), 200 µM CV-8688 (FIG. 17J), and 50 µM CV-8688 (FIG. 17K).

FIG. 20 is a summary chart showing the number and percent of zebrafish with decreased skin pigmentation after exposure to the listed conditions. The final six rows show the effects of various concentrations of compound II.

FIG. 23J is a summary chart showing percent of test compound remaining in the listed solvent after 2-hour incubation.

DETAILED DESCRIPTION OF THE INVENTION

Figure 1A:
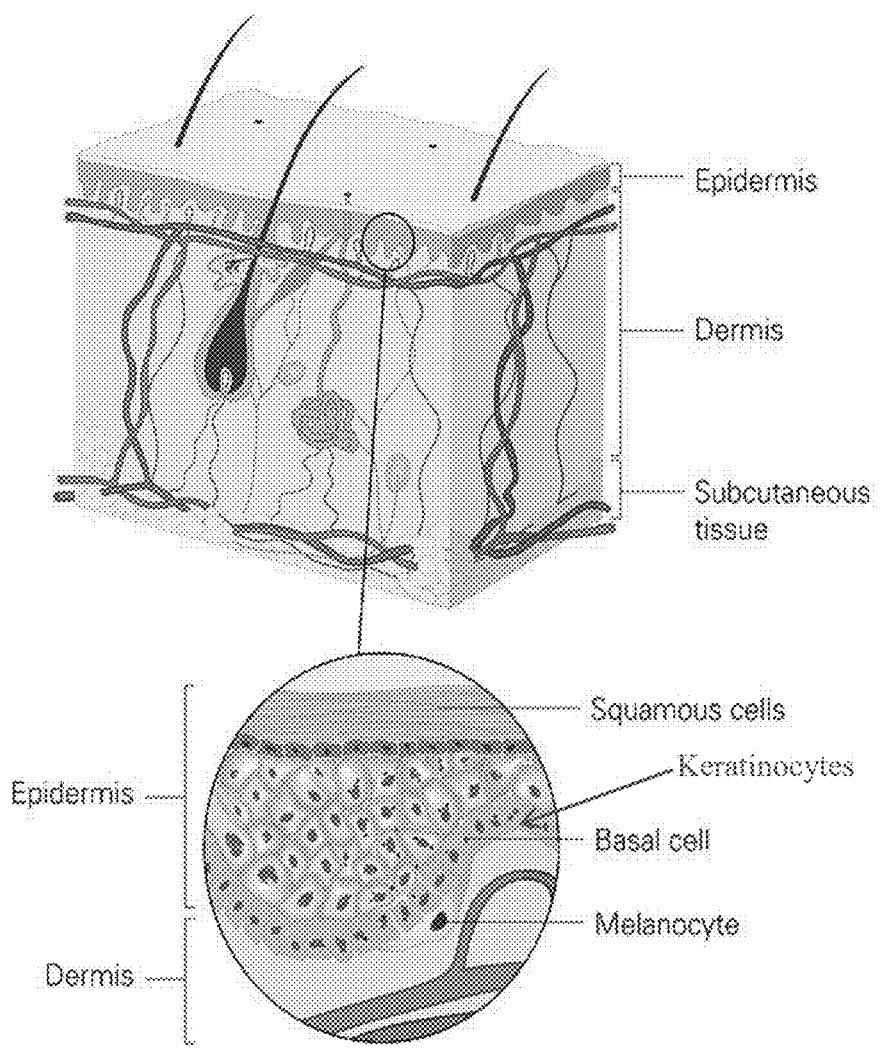
FIG. 1A is a schematic diagram of the skin's component layers. The inset diagram shows the cellular makeup of the epidermis and dermis.

One embodiment of the present invention is a compound for brightening skin. The compound is a chemical analog of a compound produced by a *Malassezia* yeast, or a crystalline form, hydrate, or cosmetically or pharmaceutically acceptable salt thereof.

As used herein, the term "compound" refers to two or more atoms that are connected by one or more chemical bonds. In the present invention, chemical bonds include, but are not limited to, covalent bonds, ionic bonds, hydrogen bonds, and van der Waals interactions. Covalent bonds of the present invention include single, double, and triple bonds. Compounds of the present invention include, but are not limited to, organic molecules.

Organic compounds/molecules of the present invention include linear, branched, and cyclic hydrocarbons with or without functional groups. The term "$C_{x-y}$" when used in conjunction with a chemical moiety, such as, alkyl, alkenyl, alkynyl or alkoxy is meant to include groups that contain from x to y carbons in the chain. For example, the term "$C_{x-y}$ alkyl" means substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{x-y}$ alkenyl" and "$C_{x-y}$ alkynyl" refer to substituted or unsubstituted unsaturated aliphatic groups analogous in length and possible substitution to the alkyls described above, but containing at least one double or triple bond respectively.

The term "aliphatic", as used herein, means a group composed of carbon and hydrogen atoms that does not contain aromatic rings. Accordingly, aliphatic groups include alkyl, alkenyl, alkynyl, and carbocyclyl groups.

The term "alkyl" means the radical of saturated aliphatic groups that does not have a ring structure, including straight chain alkyl groups, and branched chain alkyl groups.

The term "alkenyl", as used herein, means an aliphatic group containing at least one double bond.

The term "alkynyl", as used herein, means an aliphatic group containing at least one triple bond.

As used herein, an "aromatic compound", "aromatic", or compound containing an "aromatic ring" is an aryl or a heteroaryl compound. The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, indole, imidazole, oxazole, thiazole, pyrazole, pyridine, pyrazine, pyridazine, and pyrimidine, and the like. Preferably, certain compounds of the present invention include at least one, preferably two, indole groups as well as at least one aldehyde group.

The term "substituted" means moieties having at least one substituent that replaces a hydrogen atom on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. The permissible substituents can be one or more and the same or different for appropriate organic compounds.

As used herein, "skin brightening" and grammatical variations thereof refers generally to any actual or perceived reduction in skin pigmentation. Skin brightening methods have been used to reduce pigmentation of hyperpigmented areas of skin resulting from age, sun exposure, or a hyperpigmentation disorder. Application of the compounds and compositions of the present invention to, for example, a subject's skin, can reduce pigmentation so that the skin appears lighter or whiter than before said application. Skin pigmentation can be assessed in a number of ways, including, but not limited to, visual assessments using, for example, the von Luschan chromatic scale, the Fitzpatrick skin typing test (Fitzpatrick et al., 1988) and the Taylor Hyperpigmentation Scale (Taylor et al., 2005) and reflectance spectrophotometry methods (Zonios, et al., 2001). For example, the Fitzpatrick skin typing test includes six types of skin (I-VI), and Type VI skin that becomes Type V or less has been "brightened" as the term is used herein. As discussed further below, skin brightening can result due to a number of phenomena, including, but not limited to, modulation of melanocyte activity, induction of melanocyte apoptosis, agonism of an arylhydrocarbon receptor (AhR), or modulation of melanin production, melanosome biogenesis, or melanosome transfer.

Certain compounds of the present invention are produced by, isolated from, or isolatable from a *Malassezia* yeast. *Malassezia* yeasts are yeasts of the genus *Malassezia* and include, but are not limited to, *Malassezia globosa, Malassezia restricta, Malassezia furfur, Malassezia sympodialis, Malassezia slooffiae, Malassezia obtusa, Malassezia pachydermatis, Malassezia dermatis, Malassezia japonica, Malassezia nana, Malassezia yamatoensis, Malassezia equine, Malassezia caprae,* and *Malassezia cuniculi*. (Guého, et al., 1996; Gaitanis, et al., 2013). *Malassezia* yeast are part of the normal human cutaneous flora and typically produce no pathogenic effects. However, *Malassezia* yeast can cause a number of diseases, including, but not limited to pityriasis versicolor (both the hyperpigmented and hypopigmented varieties), seborrheic dermatitis, dandruff, atopic dermatitis, *Malassezia* folliculitis, psoriasis, and confluent and reticulated papillomatosis. (Gaitanis, et al., 2013).

As used herein, the term "chemical analog" refers to a compound that is structurally related to a parent compound and contains different functional groups or substituents. For example, a parent compound of the present invention is malassezin, and chemical analogs of malassezin contain certain functional groups and substituents that are distinct from malassezin. Chemical analogs of the present invention may have significant advantages over a given parent compound, including a pharmacokinetic profile suitable for cosmetic use. In some embodiments, a chemical analog is generated from a parent molecule by one or more chemical reactions. In other embodiments, alternative synthesis schemes that do not originate with a parent compound can be used to generate chemical analogs of the present invention.

A compound of the present invention is "produced by a *Malassezia* yeast" if, over the course of its lifecycle, a *Malassezia* yeast would synthesize, secrete, accumulate, or otherwise generate the compound under appropriate growth conditions. *Malassezia* yeast secrete different compounds depending on what their growth media is supplemented with. (Nazzaro-Porro, et al., 1978). The present invention includes any compound produced by a *Malassezia* yeast under any growth condition, but preferred compounds include, for example, malassezin and chemical analogs thereof.

In one aspect of this embodiment, the compound produced by a *Malassezia* yeast has the structure of formula (I):

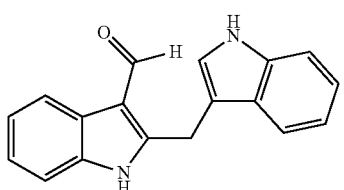

(I)

In another aspect of this embodiment, the compound is a chemical analog of malassezin.

Malassezin is one example of a compound produced by a *Malassezia* yeast of the present invention. Malassezin, also known as 2-(1H-indol-3-ylmethyl)-1H-indole-3-carbaldehyde, is a tryptophan metabolite originally isolated from *Malassezia furfur*. Malassezin is a known agonist of the arylhydrocarbon receptor (AhR), a receptor implicated in cell growth, differentiation, and gene expression. (Wille et al., 2001). Malassezin also induces apoptosis in primary human melanocytes. (Krämer, et al., 2005). Recently, certain chemical analogs of malassezin were synthesized by Winston-McPherson and colleagues, who examined the analogs' AhR agonist activity. (Winston-McPherson, et al., 2014).

Another embodiment of the present invention is a compound for inducing melanocyte apoptosis. The compound is a chemical analog of a compound produced by a *Malassezia* yeast, or a crystalline form, hydrate, or cosmetically or pharmaceutically acceptable salt thereof.

As used herein, the term "melanocyte" refers to a dendritic cell of the epidermis that normally synthesizes tyrosinase and, within melanosomes, the pigment melanin. Melanocytes of the present invention exhibit upregulation of certain genes, including, but not limited to, one or more of the following: tyrosinase (oculocutaneous albinism IA), microphthalmia-associated transcription factor, alpha-2-macroglobulin, tyrosinase-related protein 1, solute carrier family 16, GS3955 protein, v-kit Hardy-Zuckerman 4 feline sarcoma, ocular albinism 1, Rag D protein, glycogenin 2, G-protein-coupled receptor, family C, oculocutaneous albinism II, deleted in esophageal cancer 1, melan-A, SRY-box 10, ATPase, Class V, type 10C, matrix metalloproteinase 1, latent transforming growth factor beta b, ATP-binding cassette, sub-family C, hydroxyprostaglandin dehydrogenase 15, transmembrane 7 superfamily member 1, glutaminyl-peptide cyclotransferase, and other genes identified by Lee and colleagues. (Lee, et al., 2013).

Melanocytes, like many other cell types, undergo programmed cell death or, apoptosis. Melanocyte apoptosis pathways are known to those of skill in the art (Wang, et al., 2014), and apoptosis pathways generally have been reviewed by Elmore (Elmore, 2007). A compound or composition of the present invention "induces" melanocyte apoptosis by, for example, causing the activation of certain pro-apoptotic signal transduction pathways or causing the repression of certain anti-apoptotic pathways in a melanocyte. It is envisioned that the compound or composition of the present invention can directly activate/repress an apoptosis-related pathway by directly interacting with a signaling molecule of the pathway or by indirectly interacting with a molecule of the pathway via direct interaction with one or more intermediary molecules that do not typically function within the pathway.

In one aspect of this embodiment, the compound produced by a *Malassezia* yeast has the structure of formula (I):

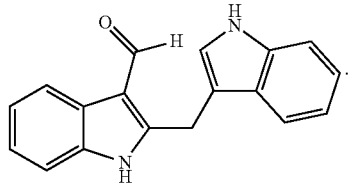

(I)

In another aspect of this embodiment, the compound is a chemical analog of malassezin.

A further embodiment of the present invention is a compound for modulating melanocyte activity. The compound is a chemical analog of a compound produced by a *Malassezia* yeast, or a crystalline form, hydrate, or cosmetically or pharmaceutically acceptable salt thereof.

Melanocyte activity can be modulated in a number of ways contemplated in the present invention, including, but not limited to, inducing melanocyte apoptosis or altering melanocyte gene expression, cell motility, cell growth, melanin production, melanosome biogenesis, or melanosome transfer.

In one aspect of this embodiment, the compound produced by a *Malassezia* yeast has the structure of formula (I):

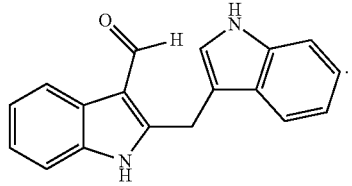

(I)

In another aspect of this embodiment, the compound is a chemical analog of malassezin.

An additional embodiment of the present invention is a compound for agonizing the arylhydrocarbon receptor (AhR). The compound is a chemical analog of a compound produced by a *Malassezia* yeast, or a crystalline form, hydrate, or cosmetically or pharmaceutically acceptable salt thereof.

As used herein, the terms "agonist", "agonizing", and grammatical variations thereof refer to a molecule that triggers (e.g., initiates or promotes), partially or fully enhances, stimulates or activates one or more biological activities. Agonists of the present invention include naturally occurring substances as well as synthetic substances.

An arylhydrocarbon receptor (AhR) of the present invention is any arylhydrocarbon receptor that naturally exists in a subject as described herein. Arylhydrocarbon receptors are known to those of skill in the art. (Noakes, 2015). Agonists of arylhydrocarbon receptors include, but are not limited to, tryptophan-related compounds such as kynurenine, kynurenic acid, cinnabarinic acid, and 6-formylindolo [3,2-b] carbazole (FICZ). Malassezin is also known as an aryl hydrocarbon receptor agonist. (Wille, et al., 2001).

In one aspect of this embodiment, the compound produced by a *Malassezia* yeast has the structure of formula (I):

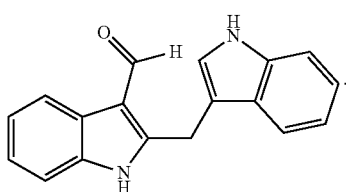
(I)

In another aspect of this embodiment, the compound is a chemical analog of malassezin.

Another embodiment of the present invention is a compound for improving hyperpigmentation caused by a hyperpigmentation disorder. The compound is a chemical analog of a compound produced by a *Malassezia* yeast, or a crystalline form, hydrate, or cosmetically or pharmaceutically acceptable salt thereof.

As used herein, the compounds, compositions, and methods of the present invention can be used to improve hyperpigmentation caused by a hyperpigmentation disorder by, for example, reducing the level of hyperpigmentation in areas affected by a hyperpigmentation disorder, slowing further hyperpigmentation, or preventing further hyperpigmentation from occurring. However, because every subject may not respond to a particular dosing protocol, regimen, or process, improving hyperpigmentation caused by a hyperpigmentation disorder does not require that the desired physiologic response or outcome be achieved in each and every subject or subject population. Accordingly, a given subject or subject population may fail to respond or respond inadequately to dosing, but other subjects or subject populations may respond and, therefore, experience improvement in their hyperpigmentation disorder.

As used herein, the term "hyperpigmentation" is an actual or a perceived skin disorder of excessive dark color. The skin impairment can be actual, for example, attributed to age, excessive sun exposure, or a disease or condition leading to dark skin areas. The dark skin areas can be in the form of spots, blotches, or relatively large areas of dark color. The skin impairment also can be perceived, for example, a perception by an individual that his/her skin shade is too dark. The individual may have a cosmetic desire to lighten the skin shade.

Hyperpigmentation disorders are disorders in which hyperpigmentation is the primary symptom as well as disorders in which hyperpigmentation occurs as a secondary symptom. Hyperpigmentation disorders of the present invention include, but are not limited to, congenital hyperpigmentation disorders and acquired hyperpigmentation disorders. Congenital hyperpigmentation disorders of the present invention include, but are not limited to, those involving epidermal hyperpigmentation (nevus cell nevus, Spitz nevus, and nevus spilus), dermal hyperpigmentation (blue nevus, nevus Ohta, dermal melanosis, nevus Ito, and Mongolian spot), ephelides, acropigmentation reticularis, Spitzenpigment/acropigmentation, and lentiginosis (generalized lentiginosis, LEOPARD syndrome, inherited patterned lentiginosis, Carney complex, Peutz-Jeghers syndrome, Laugier-Hunziker-Baran syndrome, and Cronkhite-Canada syndrome). (Yamaguchi, et al., 2014). Acquired hyperpigmentation disorders of the present invention include, but are not limited to, senile lentigines/lentigo, melasma/chloasma, Riehl's melanosis, labial melanotic macule, penile/vulvovaginal melanosis, erythromelanosis follicularis faciei Kitamura, UV-induced pigmentation (tanning and pigmentation petaloides actinica), postinflammatory pigmentation (friction melanosis and ashy dermatosis), chemical/drug-induced pigmentation (polychlorinated biphenyl, arsenic, 5-FU, bleomycin, cyclophosphamide, methotrexate, chlorpromazine, phenytoin, tetracycline, and chloroquine), pigmentary demarcation lines, and foreign material deposition (such as carotene, silver, gold, mercury, bismuth, and tattoos). Hyperpigmentation related with systemic disorders includes metabolism/enzyme disorders (hemochromatosis, Wilson's disease, Gaucher's disease, Niemann-Pick's disease, amyloidosis, ochronosis, acanthosis nigricans, and porphyria cutanea tarda), endocrine disorders (Addison's disease, Cushing syndrome, and hyperthyroidism), nutritional disorders (pellagra, vitamin B12 deficiency, folic acid deficiency, vagabond's disease, and prurigo pigmentosa), mastocytosis, collagen diseases, liver dysfunction, and kidney dysfunction. Hyperpigmentation can also be related with infectious diseases (measles, syphilis, and *Malassezia furfur*) and syndromes (von Recklinghausen's disease, Sotos syndrome, POEMS syndrome, Naegeli syndrome, Cantu syndrome, McCune-Albright syndrome, Watson syndrome, and Bloom syndrome). (Yamaguchi, et al., 2014).

In one aspect of this embodiment, the compound produced by a *Malassezia* yeast has the structure of formula (I):

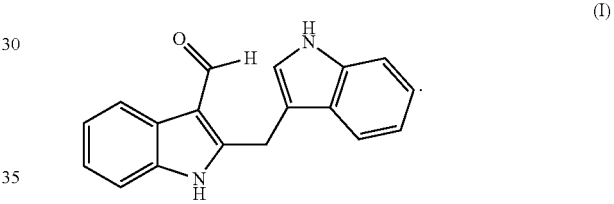
(I)

In another aspect of this embodiment, the compound is a chemical analog of malassezin.

A further embodiment of the present invention is a compound for modulating melanin production. The compound is a chemical analog of a compound produced by a *Malassezia* yeast, or a crystalline form, hydrate, or cosmetically or pharmaceutically acceptable salt thereof.

Melanin is a naturally produced pigment that gives color to skin and hair. A schematic diagram of the skin is shown in FIG. 1A. Melanin is produced by melanocytes in organelles known as melanosomes. A compound or composition of the present invention modulates melanin production in a subject by, for example, modulating melanosome biogenesis and directly or indirectly inhibiting melanin synthesis at the enzymatic level.

Melanosome biogenesis occurs via four stages: Stage I is characterized by pre-melanosomes, which are essentially non-pigmented vacuoles. In stage II, pre-melanosomes develop striations on which melanin is deposited in stage III. Stage IV results in mature melanosomes that are rich in melanin content. Compounds and compositions of the present invention modulate melanosome biogenesis by inhibiting or attenuating the biological processes that normally promote any or all of these stages. (Wasmeier, et al., 2008).

Melanin synthesis primarily involves three enzymes: tyrosinase, tyrosinase related protein-1, and dopachrome tautomerase. Additional factors that affect intracellular trafficking of these enzymes include, but are not limited to, BLOC-1, OA1, and SLC45A2. The compounds and compositions of the present invention can modulate melanin production by, for example, inhibiting or attenuating the activity of any of these enzymes or factors. (Yamaguchi, et al., 2014).

Figure 1B:
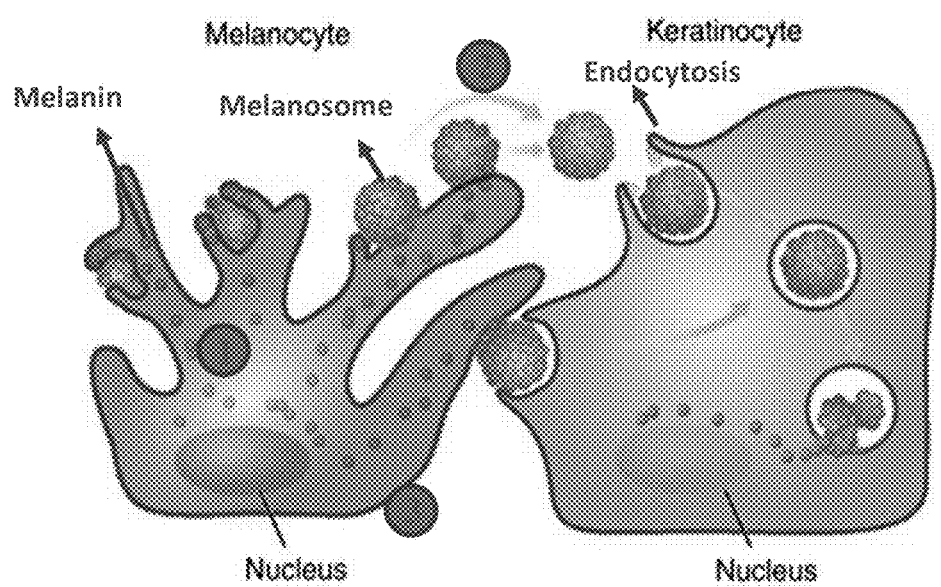
FIG. 1B is a schematic diagram showing potential mechanisms of action of hypopigmentation-causing agents.

Once melanosomes have formed and melanin has been synthesized, melanosomes need to be transferred from epidermal melanocytes to skin and hair keratinocytes. Melanosomes originate near the nucleus of melanocytes and are transported to the periphery of melanocytes along microtubules and actin filaments. Compounds and compositions of the present invention modulate melanosome transfer by interfering with any of the biological processes that result in the transport of melanosomes from the perinuclear region, to the melanocyte periphery, and into adjacent keratinocytes. A schematic diagram of melanin synthesis, melanin transport, and melanocyte apoptosis is shown in FIG. 1B.

In one aspect of this embodiment, the compound produced by a *Malassezia* yeast has the structure of formula (I):

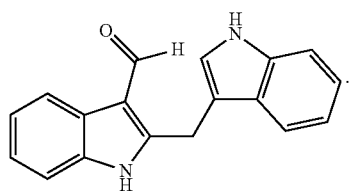

(I)

In another aspect of this embodiment, the compound is a chemical analog of malassezin.

An additional embodiment of the present invention is a compound for modulating melanosome biogenesis. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

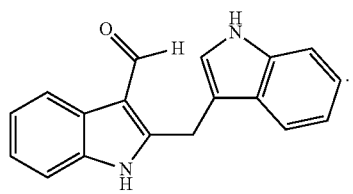

(I)

In another aspect of this embodiment, the compound is a chemical analog of malassezin.

Another embodiment of the present invention is a compound for modulating melanosome transfer. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

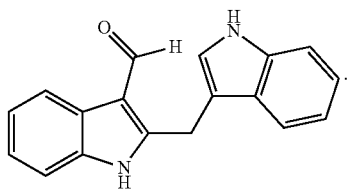

(I)

In another aspect of this embodiment, the compound is a chemical analog of malassezin.

A further embodiment of the present invention is a composition. The composition comprises a *Malassezia* yeast and a cosmetically or pharmaceutically acceptable vehicle, diluent or carrier.

An additional embodiment of the present invention is a composition. The composition comprises a compound isolated or isolatable from a *Malassezia* yeast and a cosmetically or pharmaceutically acceptable vehicle, diluent or carrier.

A compound isolated from a *Malassezia* yeast of the present invention necessarily exists, before isolation, in a *Malassezia* yeast or is produced by a *Malassezia* yeast. Therefore, a compound isolated from a *Malassezia* yeast is derived from actual yeast cells. Standard protocols for extracting compounds from cellular material are known to those of skill in the art.

A compound isolatable from a *Malassezia* yeast need not be derived from actual yeast cells. Instead, synthetic reactions can be used to generate compounds produced in yeast without the involvement of actual yeast cells. Organic synthesis reactions are well known to those of skill in the art and can be used in this regard.

Another embodiment of the present invention is a composition. The composition comprises any of the compounds disclosed herein, including analogs, and a cosmetically or pharmaceutically acceptable vehicle, diluent or carrier.

A further embodiment of the present invention is a method of brightening skin in a subject. The method comprises contacting the subject with any of the compounds or compositions disclosed herein.

As used herein, the term "contacting" and grammatical variations thereof refer to bringing two or more materials into close enough proximity that they can interact. Thus, for illustrative purposes only, a compound of the present invention can contact a melanocyte by, for example, interacting with a receptor on the surface of the melanocyte. Similarly, a composition of the present invention can contact a human subject by, for example, being applied directly to the subject's skin.

As used herein, a "subject" means a mammalian cell, tissue, organism, or populations thereof. Subjects of the present invention are preferably human, including human cells, tissues, and beings, but otherwise include, primates, farm animals, domestic animals, laboratory animals, etc. Some examples of agricultural animals include cows, pigs, horses, goats, etc. Some examples of domestic animals include dogs, cats, etc. Some examples of laboratory animals include primates, rats, mice, rabbits, guinea pigs, etc.

An additional embodiment of the present invention is a method for inducing melanocyte apoptosis in a subject. The method comprises contacting the subject with any of the compounds or compositions disclosed herein.

Another embodiment of the present invention is a method for modulating melanocyte activity in a subject. The method comprises contacting the subject with any of the compounds or compositions disclosed herein.

A further embodiment of the present invention is a method for agonizing an arylhydrocarbon receptor (AhR). The method comprises contacting the subject with any of the compounds or compositions disclosed herein.

An additional embodiment of the present invention is a method for improving hyperpigmentation caused by a hyperpigmentation disorder in a subject in need thereof. The method comprises contacting the subject with any of the compounds or compositions disclosed herein.

As used herein, a subject "in need" of improvement in hyperpigmentation caused by a hyperpigmentation disorder includes subjects with a real or perceived need of improvement.

Another embodiment of the present invention is a method for modulating melanin production in a subject. The method comprises contacting the subject with any of the compounds or compositions disclosed herein.

A further embodiment of the present invention is a method for modulating melanosome biogenesis in a subject. The method comprises contacting the subject with any of the compounds or compositions disclosed herein.

An additional embodiment of the present invention is a method for modulating melanosome transfer in a subject. The method comprises contacting the subject with any of the compounds or compositions disclosed herein.

Another embodiment of the present invention is a compound. The compound has the structure of formula (II):

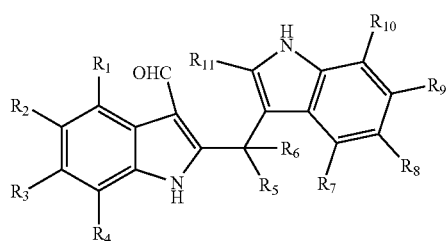

(II)

wherein: R1, R2, R3, R4, R5, R6, R7, R8, R9, R10, and R11 are independently selected from the group consisting of hydrogen and methyl, and at least one of R1, R2, R3, R4, R5, R6, R7, R8, R9, R10 and R11 is methyl; or a crystalline form, hydrate, or cosmetically or pharmaceutically acceptable salt thereof.

In one aspect of this embodiment, the compound is selected from the group consisting of:

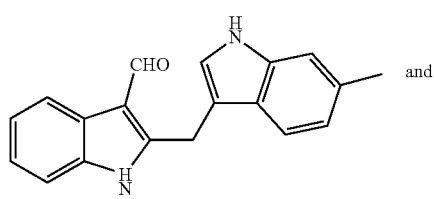

A further embodiment of the present invention is a compound. The compound has a structure of formula (III):

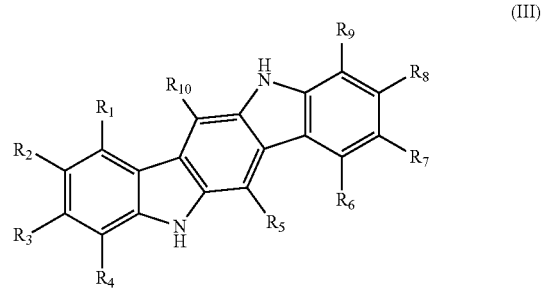

(III)

wherein: R1, R2, R3, R4, R5, R6, R7, R8, R9, and R10 are independently selected from the group consisting of hydrogen and methyl, and at least one of R1, R2, R3, R4, R5, R6, R7, R8, R9, and R10 is methyl; or a crystalline form, hydrate, or cosmetically or pharmaceutically acceptable salt thereof.

In one aspect of this embodiment, the compound is:

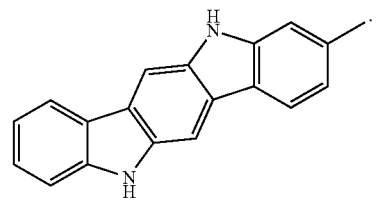

An additional embodiment of the present invention is a compound for brightening skin. The compound has the structure of formula (II):

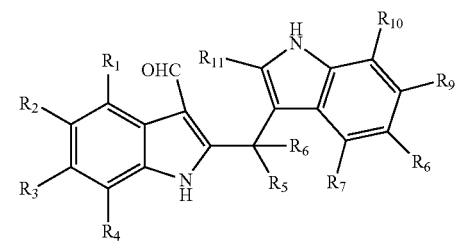

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

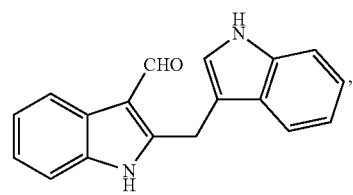

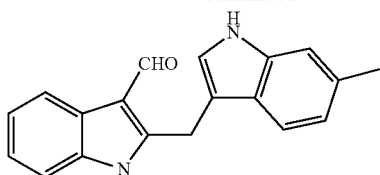 and

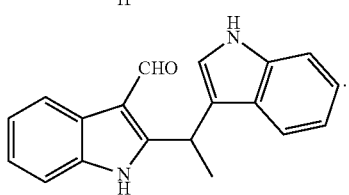

Another embodiment of the present invention is a compound for brightening skin. The compound has the structure of formula (III):

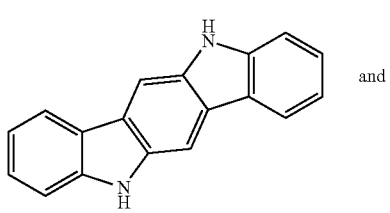

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

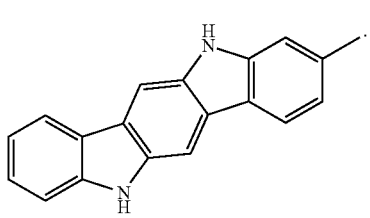

A further embodiment of the present invention is a compound for inducing melanocyte apoptosis. The compound has the structure of formula (II):

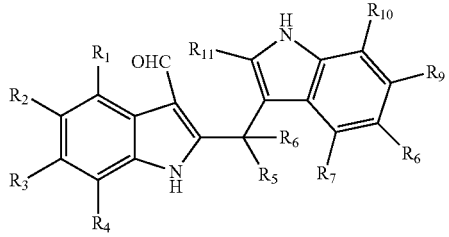

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

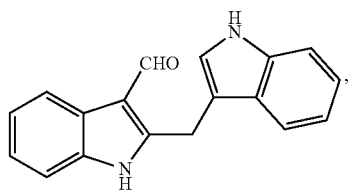

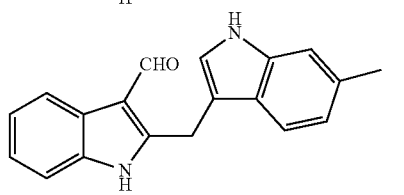 and

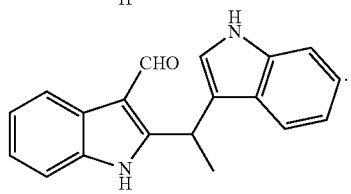

An additional embodiment of the present invention is a compound for inducing melanocyte apoptosis. The compound has the structure of formula (III):

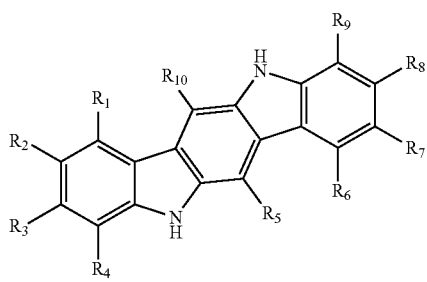

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

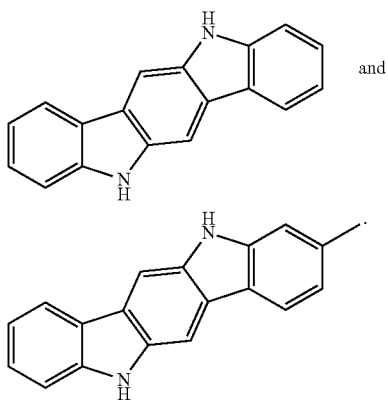

Another embodiment of the present invention is a compound for agonizing the arylhydrocarbon receptor (AhR). The compound has the structure of formula (II):

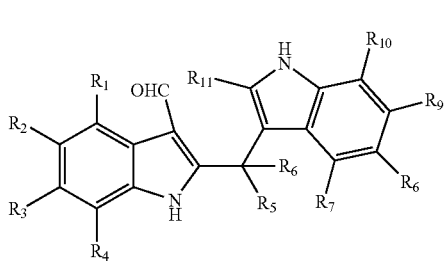

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

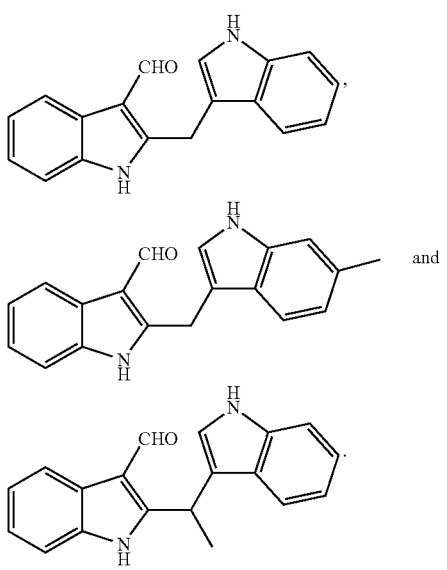

A further embodiment of the present invention is a compound for agonizing the arylhydrocarbon receptor (AhR). The compound has the structure of formula (III):

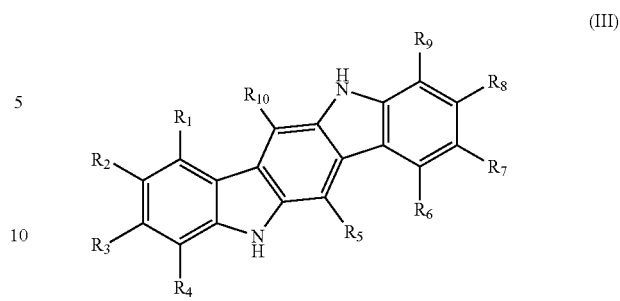

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

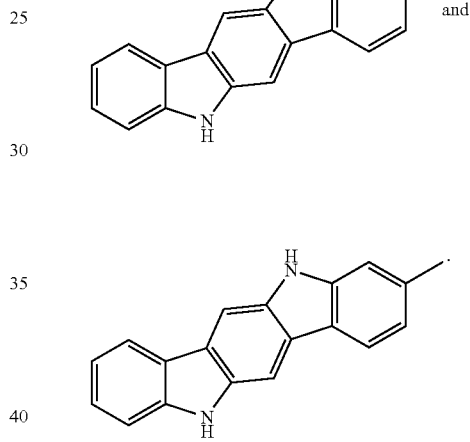

An additional embodiment of the present invention is a composition. The composition comprises a compound having the structure of formula (II)

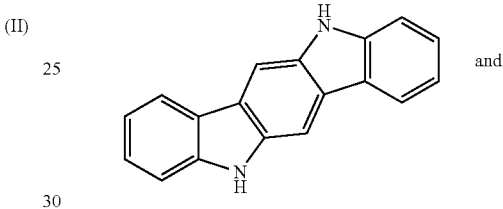

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

In one aspect of this embodiment, the compound is selected from the group consisting of:

[Structure: indole-CH2-indole with CHO group]

[Structure: indole-CH2-(methyl-indole) with CHO group] and

[Structure: indole-CH(CH3)-indole with CHO group].

Another embodiment of the present invention is a composition. The composition comprises a compound having the structure of formula (III):

(III)

[Structure of formula (III): indolo-carbazole scaffold with substituents R1–R10]

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

In one aspect of this embodiment, the compound is selected from the group consisting of:

[Structure: indolo[2,3-b]carbazole] and

[Structure: methyl-substituted indolo[2,3-b]carbazole].

A further embodiment of the present invention is a method for brightening skin in a subject. The method comprises: contacting the subject with a compound having the structure of formula (II):

(II)

[Structure of formula (II): bis-indolylmethane with CHO and R1–R11 substituents]

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

[Structure: indole-CH2-indole with CHO group],

[Structure: indole-CH2-(methyl-indole) with CHO group] and

[Structure: indole-CH(CH3)-indole with CHO group].

An additional embodiment of the present invention is a method for brightening skin in a subject. The method comprises: contacting the subject with a compound having the structure of formula (III):

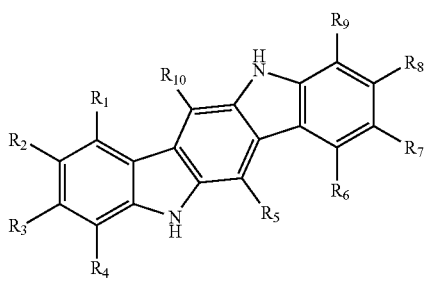

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

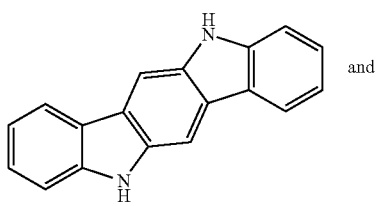

and

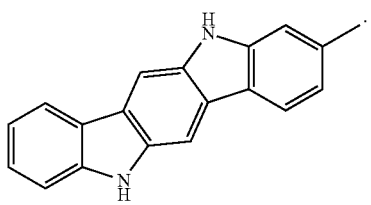

Another embodiment of the present invention is a method for inducing melanocyte apoptosis in a subject. The method comprises: contacting the subject with a compound having the structure of formula (II):

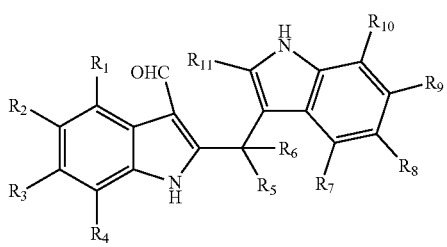

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

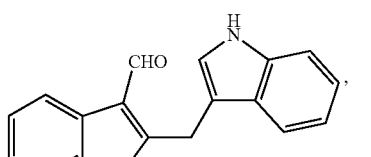

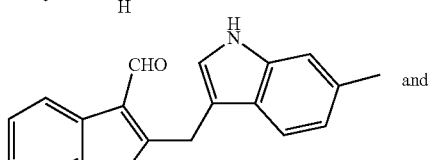
and

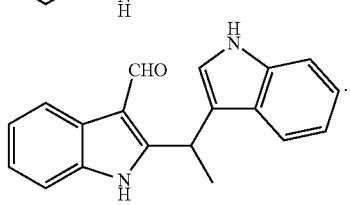

A further embodiment of the present invention is a method for inducing melanocyte apoptosis in a subject. The method comprises: contacting the subject with a compound having the structure of formula (III):

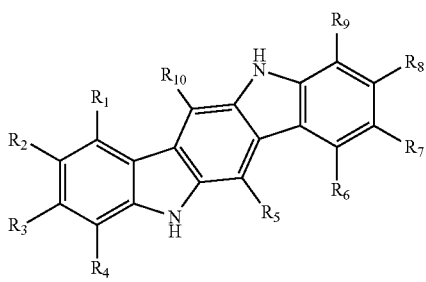

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

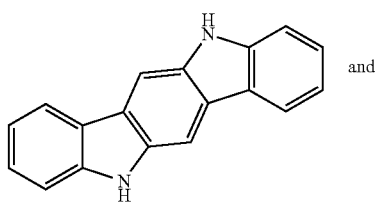
and

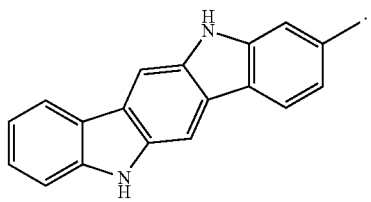 [SMILES: Cc1ccc2c(c1)[nH]c1cc3c(cc12)[nH]c1ccccc13]

An additional embodiment of the present invention is a method for agonizing an arylhydrocarbon receptor (AhR) in a subject. The method comprises: contacting the subject with a compound having the structure of formula (II):

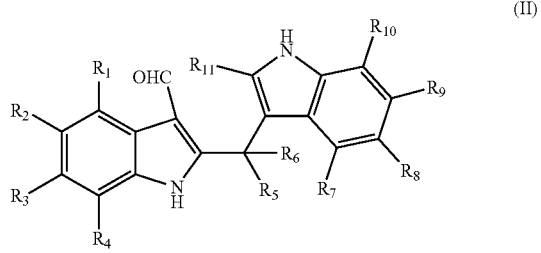

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

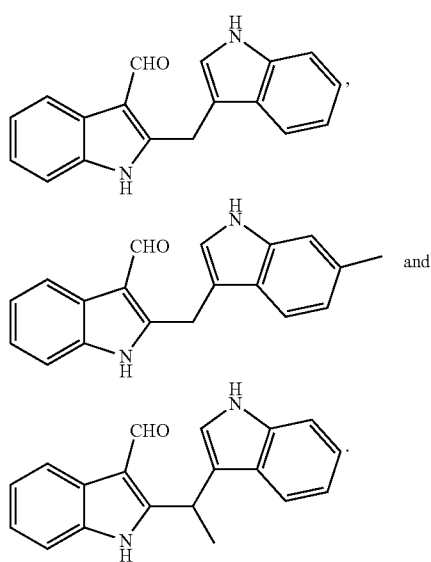

Another embodiment of the present invention is a method for agonizing an arylhydrocarbon receptor (AhR) in a subject. The method comprises: contacting the subject with a compound having the structure of formula (III):

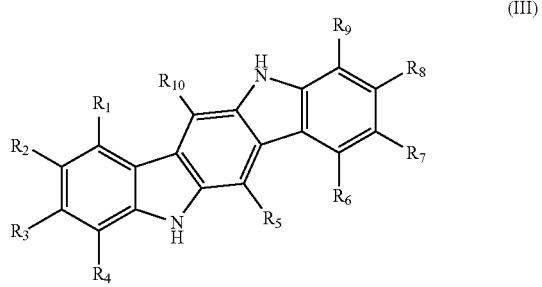

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

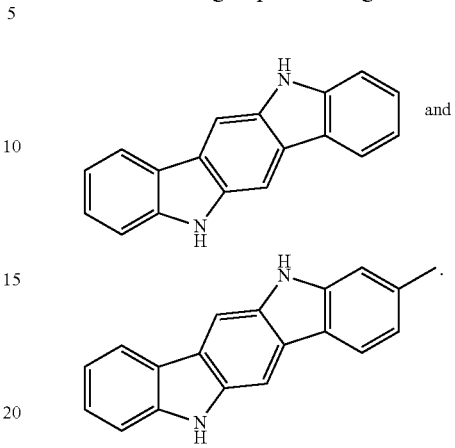

As used herein, the term "composition" means an entity comprising a compound of the present invention, as well as any entity which results, directly or indirectly, from combinations of a compound of the present invention with other ingredients. Compositions of the present invention can be used as, for example, in vitro or in vivo research reagents. Compositions of the present invention can also be applied directly to the skin of a human or non-human subject for a cosmetic effect.

A composition of the present invention may be administered in any desired and effective manner: for oral ingestion or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present invention may be administered in conjunction with other compositions. A composition of the present invention may be encapsulated or otherwise protected against gastric or other secretions, if desired.

The compositions of the invention comprise one or more active ingredients in admixture with one or more cosmetically or pharmaceutically acceptable carriers and, optionally, one or more other compounds, ingredients and/or materials. Regardless of the route of administration selected, the compounds and compositions of the present invention are formulated into cosmetically or pharmaceutically acceptable dosage forms by conventional methods known to those of skill in the art.

Cosmetically or pharmaceutically acceptable vehicles, diluents and carriers are well known in the art and include materials suitable for contact with the tissues of humans and non-humans without undue toxicity, incompatibility, instability, irritation, allergic response and the like. Cosmetically or pharmaceutically acceptable vehicles, diluents and carriers include any substantially non-toxic substance conventionally usable, for example, for topical, oral, peritoneal, or subcutaneous administration of cosmetics or pharmaceuticals in which the compounds and compositions of the present invention will remain stable and bioavailable when applied, injested, injected, or otherwise administered to a human or non-human subject. Cosmetically or pharmaceutically acceptable carriers suitable for topical application are known to those of skill in the art and include cosmetically or pharmaceutically acceptable liquids, creams, oils, lotions, ointments, gels, or solids, such as conventional cosmetic night creams, foundation creams, suntan lotions, sunscreens, hand lotions, make-up and make-up bases, masks and the like. Carriers suitable for a selected dosage form and intended route of administration are well known in the art, and acceptable carriers for a chosen dosage form and method of administration can be determined using ordinary skill in the art.

The compositions of the present invention can contain other ingredients conventional in cosmetics including perfumes, estrogen, Vitamins A, C and E, alpha-hydroxy or alpha-keto acids such as pyruvic, lactic or glycolic acids, lanolin, vaseline, aloe vera, methyl or propyl paraben, pigments and the like. Non-limiting cosmetically or pharmaceutically acceptable vehicles, diluents and carriers of the present invention include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc.

The compositions of the invention may, optionally, contain additional ingredients and/or materials commonly used in cosmetic compositions. These ingredients and materials are well known in the art and include, for example, (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more cosmetically or pharmaceutically acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the cosmetic formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include cosmetically or pharmaceutically acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions of the present invention for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions of the present invention which are suitable for vaginal administration also include pessaries, tampons, creams, gels, pastes, foams or spray formulations containing such cosmetically or pharmaceutically acceptable carriers as are known in the art to be appropriate.

Dosage forms for the topical or transdermal administration include powders, sprays, ointments, pastes, creams, lotions, gels, solutions, patches, drops, emulsions, suspensions, aerosols, and inhalants. Any desired conventional vehicles, assistants and optionally further active ingredients may be added to the formulation.

Preferred assistants originate from the group comprising preservatives, antioxidants, stabilisers, solubilisers, vitamins, colorants, odour improvers, film formers, thickeners and humectants.

Solutions and emulsions can comprise the conventional vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, groundnut oil, maize oil, olive oil, castor oil and sesame oil, glycerol fatty acid esters, polyethylene glycols and fatty acid esters of sorbitan, or mixtures of these substances.

The emulsions may exist in various forms. Thus, they can be, for example, an emulsion or microemulsion of the water-in-oil (W/O) type or of the oil-in-water (O/W) type, or a multiple emulsion, for example of the water-in-oil-in-water (W/O/W) type.

The compositions according to the invention may also be in the form of emulsifier-free, disperse preparations. They can be, for example, hydrodispersions or Pickering emulsions.

Suspensions may comprise conventional vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Pastes, ointments, gels and creams may comprise conventional vehicles, for example animal and vegetable fats, waxes, paraffins, starch, tragacanth, cellulose derivatives, polyethylene glycols, silicones, bentonites, silicic acid, talc and zinc oxide, or mixtures of these substances.

Face and body oils may comprise the conventional vehicles, such as synthetic oils, such as fatty acid esters, fatty alcohols, silicone oils, natural oils, such as vegetable oils and oily plant extracts, paraffin oils, lanolin oils, or mixtures of these substances.

Sprays may comprise the conventional propellants, for example chlorofluorocarbons, propane/butane or dimethyl ether.

Compositions of the present invention suitable for parenteral administrations comprise one or more compounds in combination with one or more cosmetically or pharmaceutically acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable cosmetic form may be brought about by the inclusion of agents which delay absorption.

In some cases, in order to prolong the effect, it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered composition may be accomplished by dissolving or suspending the active composition in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The compositions of the present invention may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

In the present invention, the term "crystalline form" means the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

The term "hydrate", as used herein, means a solid or a semi-solid form of a chemical compound containing water in a molecular complex. The water is generally in a stoichiometric amount with respect to the chemical compound.

As used herein, "cosmetically or pharmaceutically acceptable salt" refers to a derivative of the compounds disclosed herein wherein the compounds are modified by making acid or base salts thereof. Examples of cosmetically or pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2,2',2"-nitrilotris(ethanol)), trometh-amine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further cosmetically or pharmaceutically acceptable salts can be formed with cations from metals like aluminum, calcium, lithium, magnesium, potassium, sodium, zinc and the like.

The cosmetically or pharmaceutically acceptable salts of the present invention can be synthesized from a compound disclosed herein which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

It is envisioned that the compounds and compositions of the present invention may be included in cosmetic or pharmaceutical compositions.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The following examples are provided to further illustrate the methods of the present invention. These examples are illustrative only and are not intended to limit the scope of the invention in any way.

EXAMPLES

Example 1

Materials and Methods

Isolation of Compounds Produced by *Malassezia*

Malassezin is isolated using, for example, the procedures outlined in Wille et al., 2001. The protocol is briefly outlined below.

Medium

A medium consisting of Tween 80 (30 mL), cycloheximide (0.5 g), chloramphenicol (0.05 g), agar (20 g), and a volume of water sufficient for a 1000 mL mixture is sterilized and mixed with 0.3% sterile filtered L-tryptophan at a concentration of 0.3 g % at 50° C. 10 mL portions are poured into 10 cm Petri dishes and the pH is adjusted to 5.5 using 0.1 M HCl.

Cultivating *Malassezia furfur* and Isolating Compounds Produced By *M. furfur*

*Malassezia furfur* is swabbed on the medium described above and incubated for 14 days at 30° C. The contents of the Petri dish are pureed and extracted with ethyl acetate for 12 hours. The extract is filtered over glass wool, evaporated to dryness, and dissolved in methanol. The extract is then fractionated by chromatography on Sephadex LH-20 with methanol as the eluent. Further separation is accomplished with preparative thin-layer chromatography with toluene: ethyl formate:formic acid (10:5:3). Main zones are partitioned between water and ethyl acetate. Fractions are analyzed for activity of interest. Compounds from fractions of interest are isolated by HPLC.

Synthesis of Malassezin and Chemical Analogs of Malassezin

Malassezin is synthesized according to the protocol set forth in Wille et al., 2001. Chemical analogs of malassezin are synthesized according to novel synthesis protocols, as well as those described in Winston-McPherson, et al., 2014.

Screening Protocols

Effective skin brightening compounds are evaluated using both screening protocols known to those of skill in the art and novel screening methods. For example, malassezin and chemical analogs thereof are evaluated by a tyrosinase bioassay, as described above. Other screening protocols involving both in vitro cell and in vivo tissue models are utilized, including aryl hydrocarbon receptor (AhR) binding assays.

Tyrosinase Bioassay

Tyrosinase bioassays are performed as described in Wille et al., 2001. Briefly, L-DOPA is mixed with tyrosinase enzyme. Extinction is measured over 1 minute, indicating the formation of dopaquinone. Using, for example, the fractions discussed above, these fractions are dissolved in DMSO and added directly to the tyrosinase reaction, with pure DMSO as a control. Tyrosinase inhibitory activity is measured as reduced increase in extinction compared to control.

Aryl Hydrocarbon Receptor Binding Assay

AhR binding assays are performed according to the protocol described in, for example, Song, et al., 2002. Briefly, human and murine AhRs are expressed in vitro using, for example, a TnT Quick-coupled Reticulocyte Lysate Systems reaction (Promega, Madison, WI). Receptor ligand binding studies utilize velocity sedimentation on sucrose gradients as described in Karchner, et al., 1999.

EROD Assay

Compounds, compositions, and formulations of the present invention are also evaluated using the ethoxyresorufin-O-deethylase (EROD) assay known to those of skill in the art. (Donato, et al., 1993; Whyte, et al., 2000; Wille et al., 2001).

Melanocyte Apoptosis Assays

Candidate compounds are evaluated for apoptosis-inducing activity in melanocytes. Human epidermal melanocytes are cultured in Medium 254 supplemented with Human Melanocyte Growth Supplement (HMGS) (Thermo-Fisher Scientific, Waltham, MA) or Dermal Cell Basal Medium (ATCC, Manassas, VA). Additional components of human melanocyte growth media can include, but are not limited to, insulin (5 μg/ml), ascorbic acid (50 μg/ml), L-glutamine (6 mM), epinephrine (1.0 μM), and calcium chloride (0.2 mM). Human melanocyte cultures are maintained at 37° C. in 5% $CO_2$.

Candidate compounds are diluted in DMSO and mixed directly into melanocyte cultures. Equivalent volumes of pure DMSO are used as controls. Cytotoxicity assays known to those of skill in the art are performed according to manufacturer's instructions. Cytotoxicity assays that are used in the present invention include, but are not limited to, CellTox™ Green Cytotoxicity Assay, Apo-ONE fluorescent caspase assays, ApoTox-Glo™ assay, and Caspase-Glo® assays (Promega, Madison, WI). Fluorescence detection is accomplished using standard FACS or microscopy assays known to those in the art, including those described in Krämer, et al., 2005.

Additional means of assessing apoptosis are used, including FACS analyses for annexin V and Western blots for caspase-9 expression. Western blotting is performed according to methods known to those of skill in the art.

Mouse Xenograft Assays

Mouse xenograft models of human skin are generated according to protocols known in the art. (Black, et al., 1985; Manning et al., 1973; Reed, et al., 1973; Plenat, et al., 1992; Scott et al., 1998; Otulakowski, et al., 1994). Once established, mouse xenograft models are exposed to compounds of the present invention and changes in pigmentation are observed as compared to controls. Changes in skin pigmentation are assessed using various pigmentation scales known to those of skill in the art, including, but not limited to, the Fitzpatrick skin typing test and the Taylor Hyperpigmentation Scale. (Taylor, et al., 2005).

Human Assays

Compounds, compositions, and formulations of the present invention are applied to humans, for example, on human skin, and compared to control substances. Changes in skin pigmentation are assessed using various pigmentation scales known to those of skill in the art, including, but not limited to, the Fitzpatrick skin typing test and the Taylor Hyperpigmentation Scale.

Example 2

Biochemical Target of Malassezin and Its Analogs

It is expected that the compounds and compositions of the present invention will exhibit, for example, tyrosinase inhibition and AhR agonist activity comparable to malassezin. Compounds and compositions of the present invention are expected to exhibit, for example, more potent tyrosinase inhibition and stronger AhR agonism compared to malassezin. Likewise, certain of the compounds and compositions of the present invention are expected to be less effective tyrosinase inhibitors and AhR agonists than malassezin. Such compounds, compositions, and formulations may have more favorable toxicity profiles compared to more potent compounds.

Example 3

In Vitro Efficacy

It is expected that the compounds and compositions of the present invention will induce melanocyte apoptosis and modulate melanocyte activity, melanin production, melanosome biogenesis, and/or melanosome transfer at least as potently as malassezin. It is also contemplated that certain of the compounds and compositions of the present invention will effect these biological processes less potently than malassezin. Such compounds and compositions may have more favorable toxicity profiles compared to more potent species.

Example 4

In Vivo Efficacy

It is expected that the compounds and compositions of the present invention will be at least as effective as malassezin for brightening skin and improving hyperpigmentation caused by hyperpigmentation disorders. It is further expected that the compounds and compositions of the present invention will exhibit favorable pharmacokinetic profiles in terms of, for example, half-life and absorption. Certain compounds will exhibit a longer half-life, whereas others will exhibit a shorter half-life. Similarly, certain compounds will exhibit different absorption profiles, with some compounds taking longer to be fully absorbed and others taking less time to be fully absorbed.

Example 5

Synthesis of Malassezin and Malassezin Derivatives

Figure 2A:
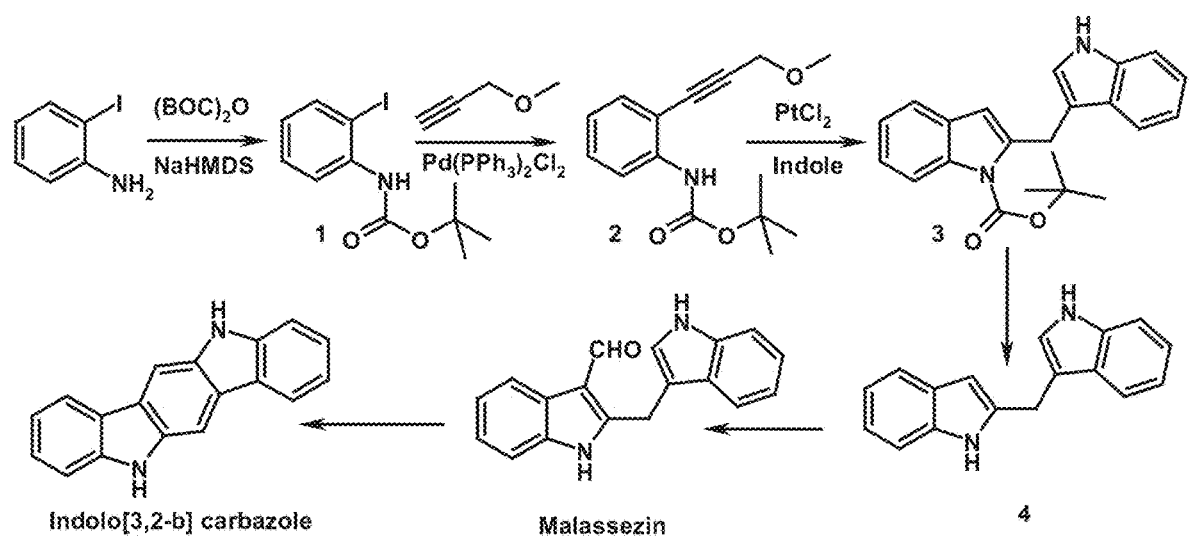
FIGS. 2A-2C show synthetic schemes for malassezin and malassezin derivatives.

Malassezin ("CV-8684") and its cyclized derivative indolo[3,2-b] carbazole ("CV-8685") were synthesized according to the scheme shown in FIG. 2A.

Synthesis of tert-butyl (2-iodo-phenyl)carbamate, Compound 1

To a solution of 2-iodo-aniline (25.0 g, 0.114 mol) in tetrahydrofuran (250 mL) at 0° C. was added LiHMDS (251.0 mL, 1 M in THF, 0.251 mol) slowly while maintaining the internal temperature below 5° C. over 40 min. After 30 min stirring at 0° C., a solution of BOC anhydride (27.0 g, 0.125 mol) in THF (50 mL) was slowly added while maintaining the internal temperature below 5° C. over 40 min. The reaction mixture was warmed to ambient temperature and stirred 1 hr. Saturated $NH_4Cl$ (250 mL) was added to quench the reaction. The organic layer was separated and washed with water (150 mL). The combined aqueous layer was extracted with ethyl acetate (2×150 mL), the layers were separated. The ethyl acetate layer was combined with the original organic layer and concentrated in vacuo to give as brown oil. The crude compound purified by column chromatography (0-5% ethyl acetate/hexanes). Compound 1 was obtained as a light yellow liquid (29.0 g, 80%).

Synthesis of Compound 2

Copper iodide (0.95 g, 10% mol) and $PdCl_2(PPh_3)_4$ (1.75 g, 5% mol) was added to a degassed solution of compound 1 (16.0 g, 0.05 mol), propargyl methyl ether (4.25 g, 0.06 mol) in triethylamine (200 mL) at ambient temperature. After stirring at ambient temperature over 2 hr, the reaction was complete (monitored by TLC using 10% ethyl acetate/hexanes). The reaction mixture diluted with ethyl acetate (300 mL), reaction mixture was washed with water, saturated NaCl and dried over $Na_2SO_4$. The solvent was filtered and concentrated in vacuo to give as brown oil. The crude compound purified by column chromatography (10% ethyl acetate/hexane). Compound 2 was obtained as a light yellow liquid (13.0 g, 99%).

Synthesis of Compound 3

To an oven-dried flask was added PtCl2 (0.26 g, 0.001 mol), Na2CO3 (1.6 g, 0.015 mol), indole (2.32 g, 0.02 mol) and compound 2 (2.6 g, 0.01 mol) in dioxane (120 mL). The flask was degassed with nitrogen, sealed and heated to 100° C. overnight. After the reaction was complete (monitored by TLC using 10% ethyl acetate/hexanes). The solvent was evaporated under reduced pressure. The reaction mixture diluted with ethyl acetate (200 mL), reaction mixture was washed with water, saturated NaCl and dried over $Na_2SO_4$. The solvent was filtered and concentrated in vacuo to give as brown oil.

This reaction was repeated using compound 2 (2.6 g, 0.01 mol) in different batch. Both batches crude compounds were combined and purified by column chromatography (10% ethyl acetate/hexane). Compound 3 was obtained as a light brown solid (3.8 g, 55%).

Synthesis of Compound 4

Potassium carbonate (4.6 g, 0.0329 mol) was added to a solution of compound 3 (3.8 g, 0.0109 mol) in methanol (150 mL) and water (50 mL) mixture at ambient temperature. The resulting suspension was heated to reflux overnight. After the reaction was complete (monitored by TLC using 20% ethyl acetate/hexanes). The reaction mixture was cooled to ambient temperature and solvent concentrated in vacuo. The residue taken in ethylacetate (200 mL) and washed with water and brine then dried (sodium sulfate), filtered, solvent concentrated in vacuo to give as a brown solid. Crude compound purified by column chromatography (20% ethyl acetate/hexane. Compound 4 was obtained as an orange color solid (2.2 g, 81%).

Synthesis of compound Malassezin (CV-8684)

To a dried 100 mL two neck round-bottom flask under argon at 0° C., dimethylformamide (20 mL) was added. $POCl_3$ (075 g, 0.0048 mol) slowly added while maintaining the internal temperature below 5° C. over 10 min. After 30 min stirring at 0° C., a solution of compound 4 (1.0 g, 0.004 mol) in dimethylformamide (5 mL) was slowly added while maintaining the internal temperature below 5° C. over 10 min. The resulting mixture was stirred at ambient temperature overnight. After the reaction was complete (monitored by TLC using 20% ethyl acetate/hexanes). The reaction mixture was poured into saturated aqueous sodium bicarbonate (150 mL) and stirred for 1 hr. Resulting mixture was extracted with ethyl acetate (2×100 mL). The organic layers were combined and washed with water, saturated NaCl and dried over $Na_2SO_4$. The solvent was filtered and concentrated in vacuo to give as brown solid. The crude compound purified by column chromatography (0-20% ethyl acetate/hexanes). Compound Malassezin (CV-8684) was obtained as a light pink solid (0.82 g, 74%).

HPLC purity: 97.8% (area %). $^1$H-NMR, $^{13}$C spectrum consistent with the structure. ESI-MS: Calc. for $C_{18}H_{15}N_2O$ $(M+H)^+$: 275, found: 275.2.

Synthesis of compound Indolo[3,2-b] carbazole (CV-8685). Concentrated HCl (0.25 mL) was added to a solution of malassezin (0.75 g) in tetrahydrofuran (120 mL) at ambient temperature. The resulting mixture was heated to reflux overnight. After the reaction was complete (monitored by TLC using 40% ethyl acetate/hexanes). The reaction mixture was cooled to ambient temperature and stirred for 1 hr. Filtered the solid, washed with tetrahydrofuran (20 mL) and dried to give Indolo[3,2-b] carbazole (CV-8685) light yellow solid (0.55 g, 78%).

HPLC purity: 96.22% (area %). $^1$H-NMR, $^{13}$C spectrum consistent with the structure. ESI-MS: Calc. for $C_{18}H_{13}N_2$ $(M+H)^+$: 257, found: 257.5.

Figure 2B:
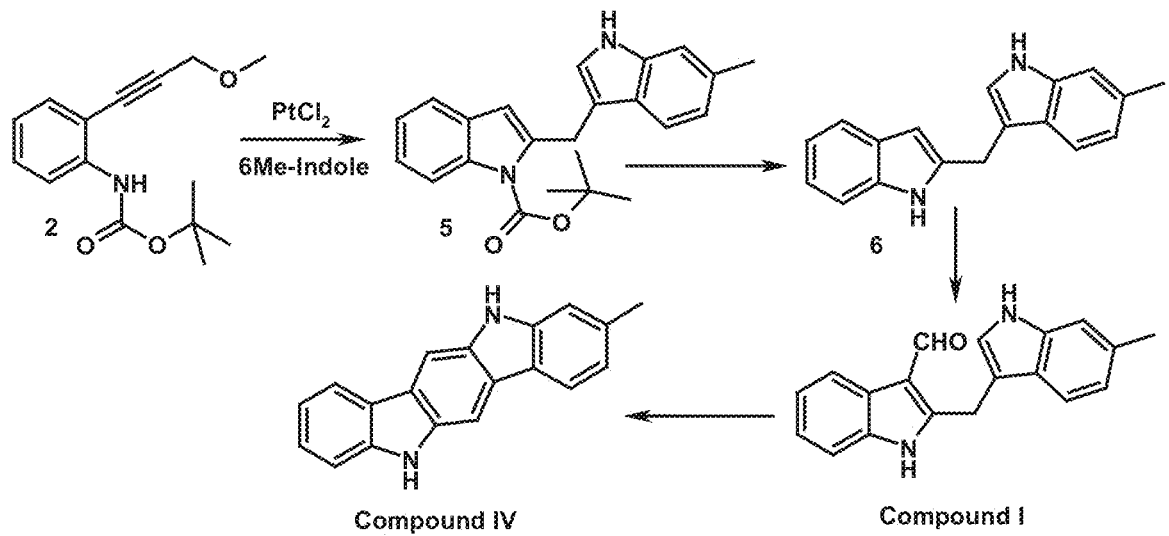

Compound I ("CV-8686") and compound IV ("CV-8687") were synthesized according to the scheme shown in FIG. 2B.

Synthesis of Compound 5

To an oven-dried flask was added PtCl2 (1.0 g, 0.0038 mol), Na2CO3 (6.1 g, 0.057 mol), 6-methyl indole (10.0 g, 0.076 mol) and compound 2 (10.0 g, 0.038 mol) in dioxane (250 mL). The flask was degassed with nitrogen, sealed and heated to 100° C. overnight. After the reaction was complete (monitored by TLC using 10% ethyl acetate/hexanes). The solvent was evaporated under reduced pressure. The reaction mixture diluted with ethyl acetate (400 mL), reaction mixture was washed with water, saturated NaCl and dried over $Na_2SO_4$. The solvent was filtered and concentrated in vacuo to give as brown oil. Crude compound purified by column chromatography (10% ethyl acetate/hexane). Compound 5 was obtained as a light brown solid (6.5 g, 47%).

Synthesis of Compound 6

Potassium carbonate (7.4 g, 0.054 mol) was added to a solution of compound 5 (6.5 g, 0.018 mol) in methanol (150 mL) and water (50 mL) mixture at ambient temperature. The resulting suspension was heated to reflux overnight. After the reaction was complete (monitored by TLC using 20% ethyl acetate/hexanes). The reaction mixture was cooled to ambient temperature and solvent concentrated in vacuo. The residue taken in ethylacetate (200 mL) and washed with water and brine then dried (sodium sulfate), filtered, solvent concentrated in vacuo to give as brown solid. Crude compound purified by column chromatography (20% ethyl acetate/hexane). Compound 6 was obtained as an orange color solid (3.3 g, 72%).

Synthesis of Compound Compound I (CV-8686)

To a dried 100 mL, two neck round-bottom flask under argon at dimethylformamide (20 mL) was added. $POCl_3$ (0.6 g, 0.0038 mol) slowly added while maintaining the internal temperature below 5° C. over 10 min. After 30 min stirring at 0° C., a solution of compound 6 (1.0 g, 0.0038 mol) in dimethylformamide (5 mL) was slowly added while maintaining the internal temperature below 5° C. over 10 min. The resulting mixture was stirred at ambient temperature overnight. After the reaction was complete (monitored by TLC using 20% ethyl acetate/hexanes). The reaction mixture was poured into saturated aqueous sodium bicarbonate (150 mL) and stirred for 1 hr. Resulting mixture was extracted with ethyl acetate (2×100 mL). The organic layers were combined and washed with water, saturated NaCl and dried over $Na_2SO_4$. The solvent was filtered and concentrated in vacuo to give as brown solid. The crude compound purified by column chromatography (0-20% ethyl acetate/hexanes). Compound I (CV-8686) was obtained as a light pink solid (0.84 g, 75%).

HPLC purity: 97.01% (area %). $^1$H-NMR, $^{13}$C spectrum consistent with the structure. ESI-MS: Calc. for $C_{19}H_{17}N_2O$ $(M+H)^+$: 289, found: 289.1.

Synthesis of Compound Compound IV (CV-8687)

Concentrated HCl (0.3 mL) was added to a solution of compound I (1.0 g) in tetrahydrofuran (125 mL) at ambient temperature. The resulting mixture was heated to reflux overnight. After the reaction was complete (monitored by TLC using 40% ethyl acetate/hexanes). The reaction mixture was cooled to ambient temperature and stirred for 1 hr. Filtered the solid, washed with tetrahydrofuran (20 mL) and dried to give compound IV (CV-8687) light yellow solid (0.84 g, 89%).

HPLC purity: 98.4% (area %). $^1$H-NMR, $^{13}$C spectrum consistent with the structure. ESI-MS: Calc. for $C_{19}H_{15}N_2$ (M+H)$^+$: 271, found: 271.3.

Figure 2C:
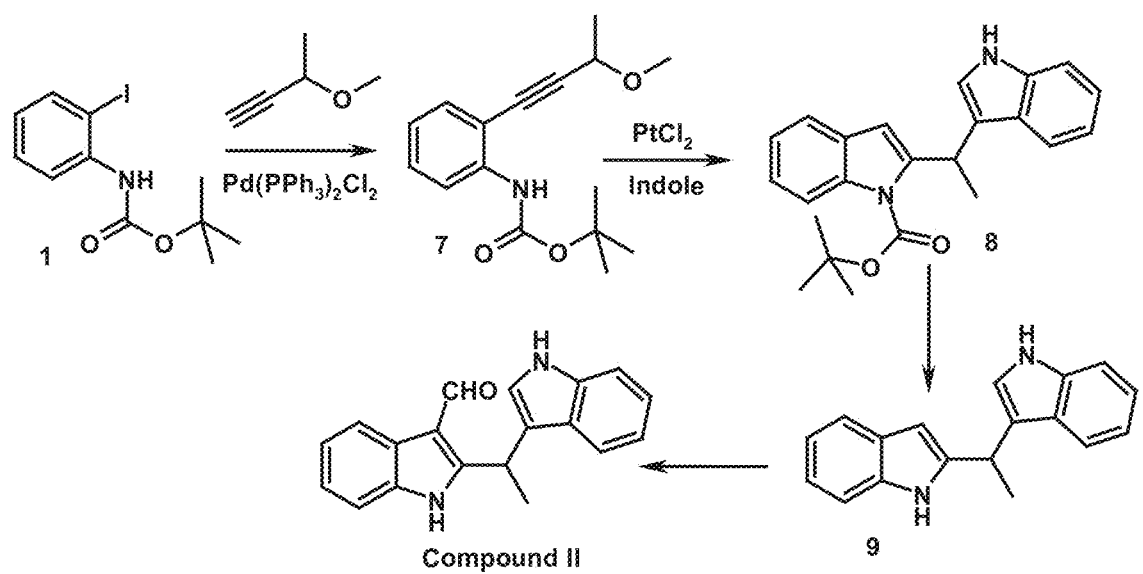
Figures 3B, 3C, 3D, 3E, 3F, 3G:
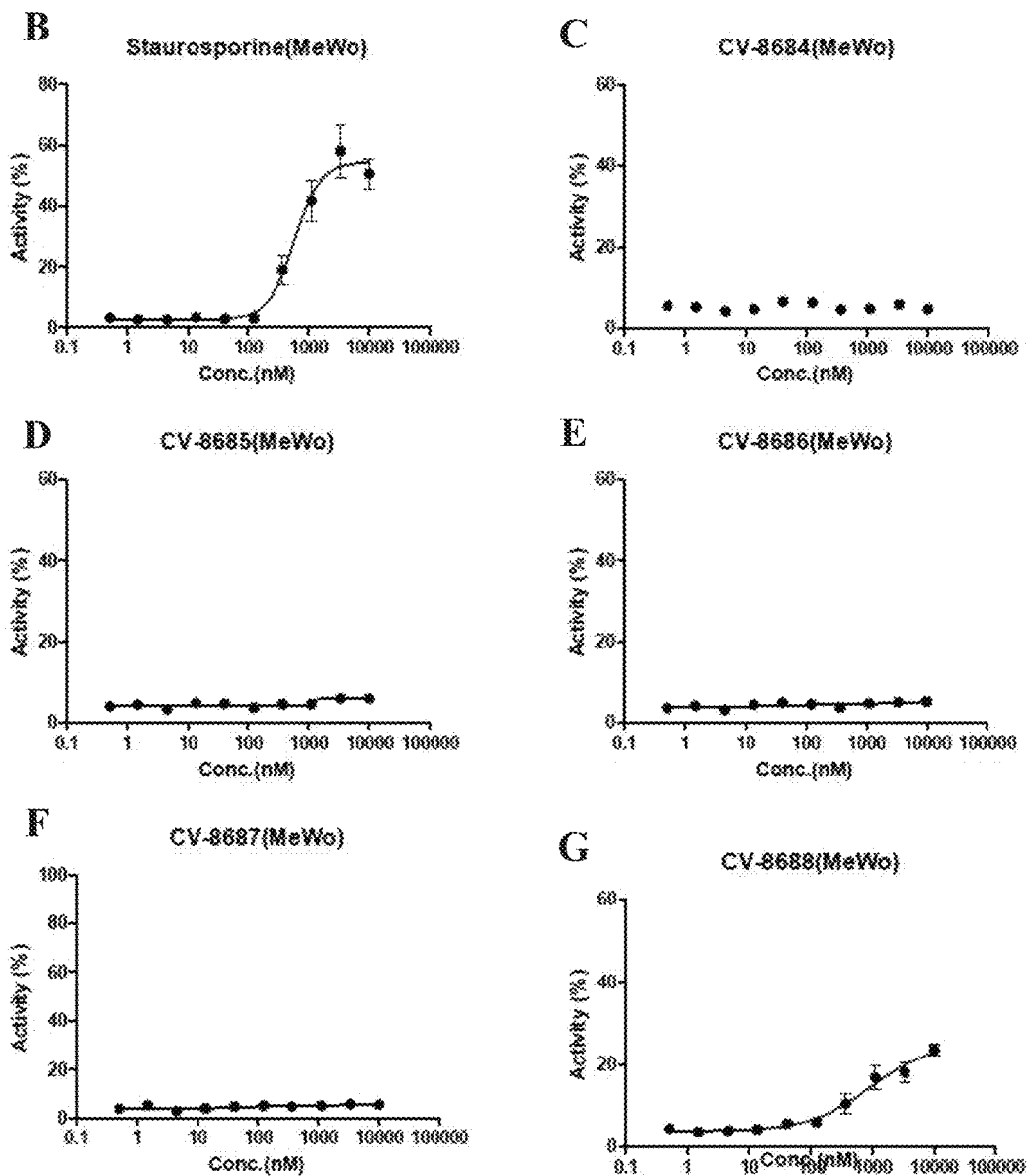
FIGS. 3B-3M are line graphs showing the percentage of MeWo (FIGS. 3B-3G) or WM115 (FIGS. 3H-3M) cells labeled with annexin V after exposure to various concentrations of the listed compounds.
Figures 3H, 3I, 3J, 3K, 3L, 3M:
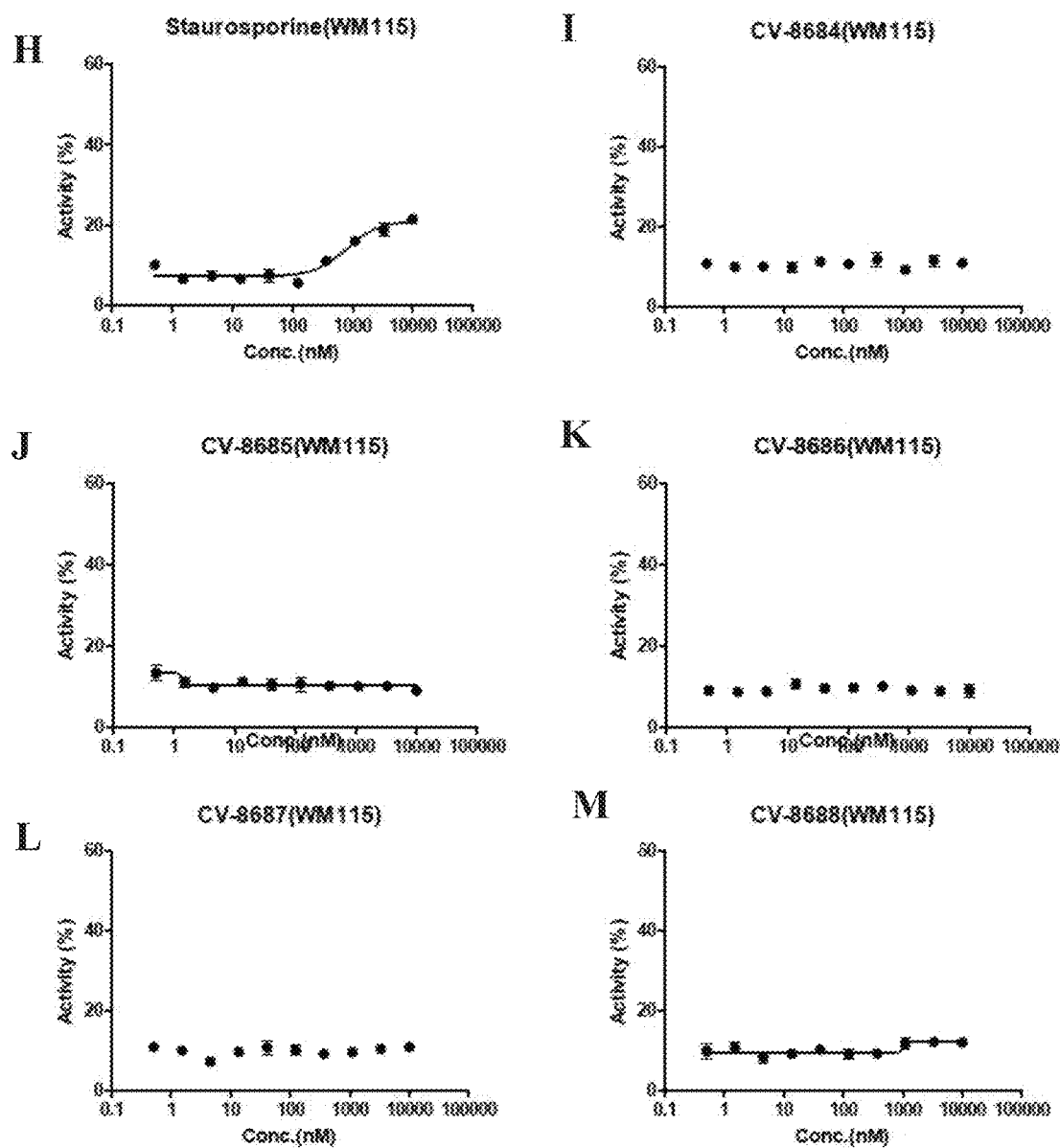
Figures 4E, 4F, 4G, 4H, 4I, 4J:
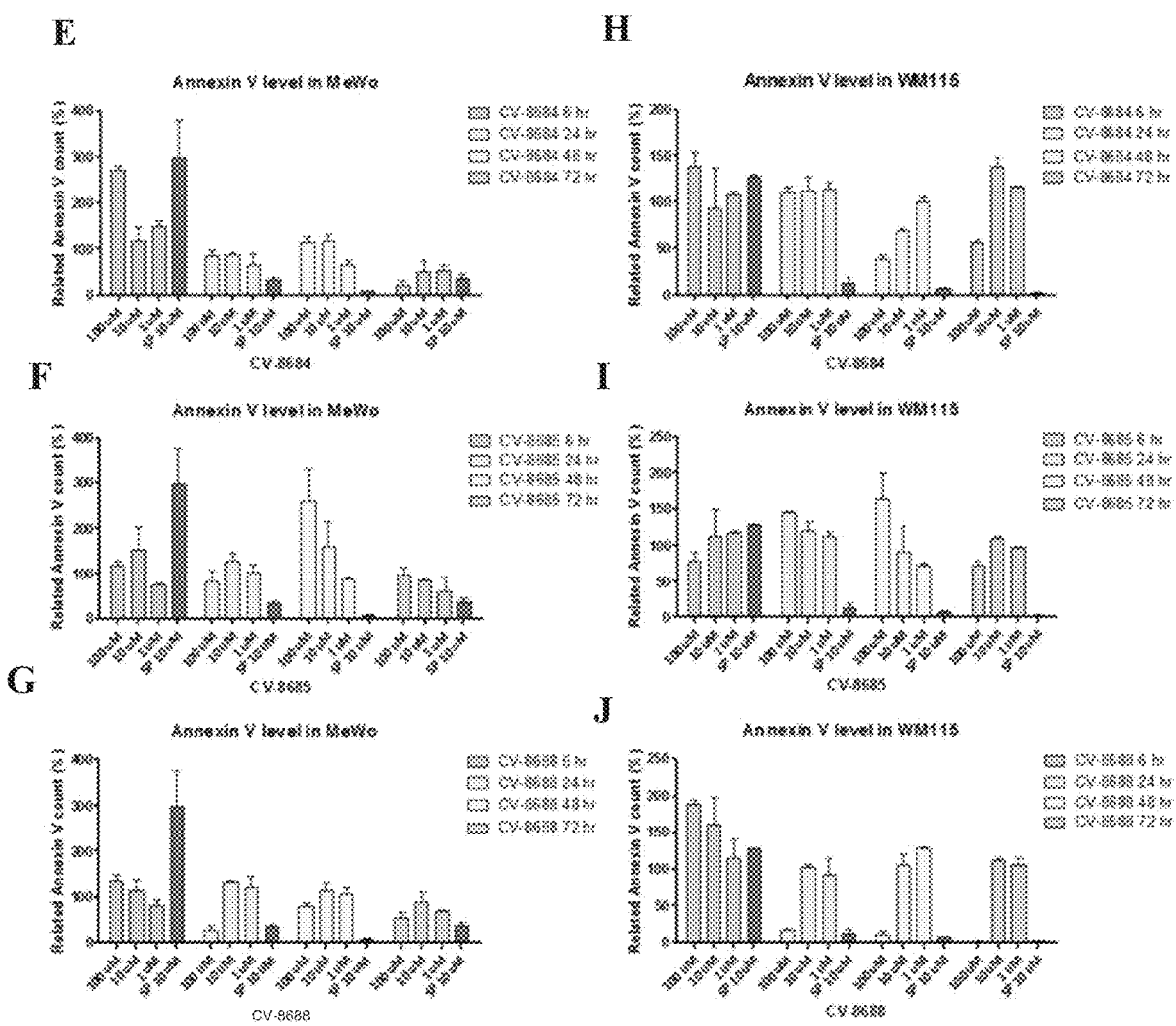
FIGS. 4E-4J are histograms showing results from FIGS. 4A-4D.
Figure 4K:
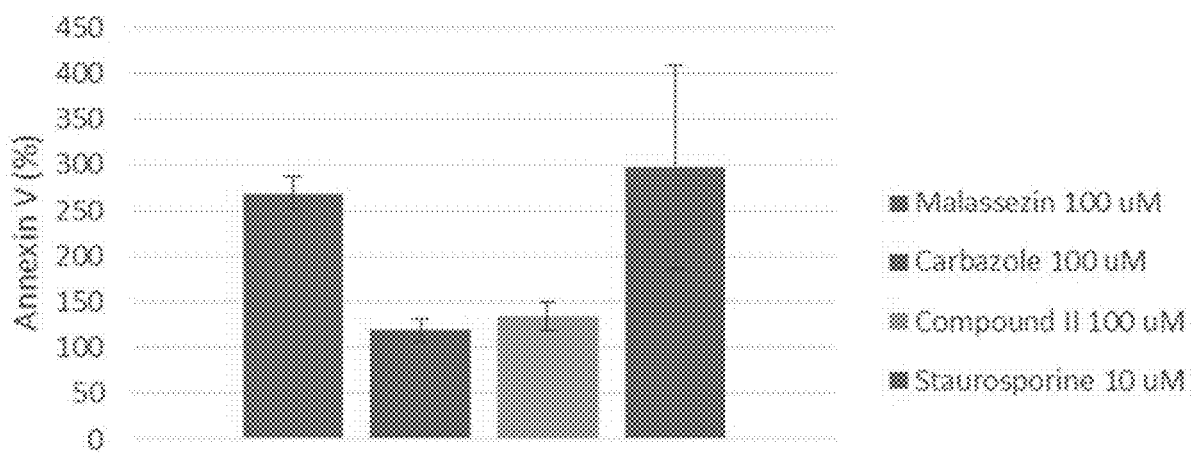
FIGS. 4K and 4L are histograms showing the percentage of MeWo (FIG. 4K) and WM115 (FIG. 4L) cells labeled with annexin V after 6-hour exposure to the listed compounds at the concentrations shown.
Figure 4L:
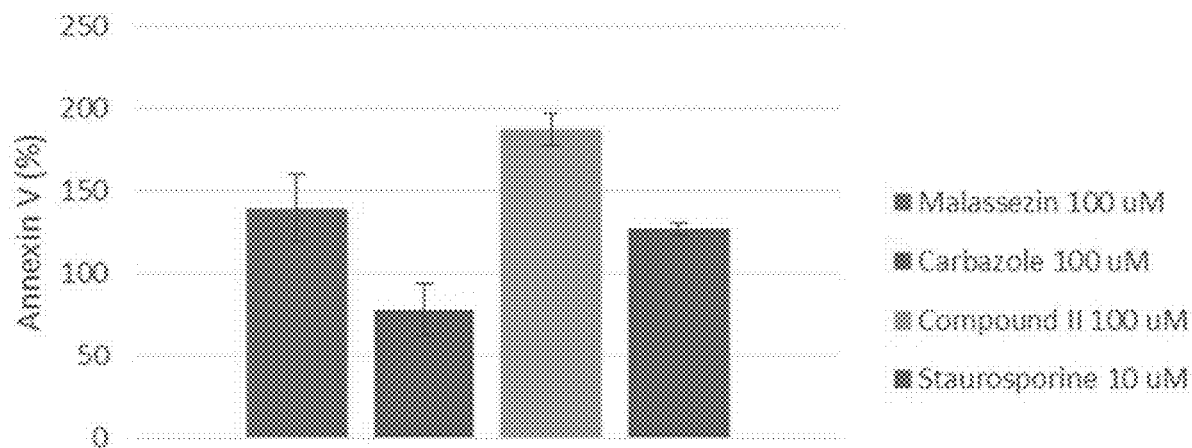
Figures 5A, 5B, 5C, 5D, 5E, 5F, 5G, 5H, 5I, 5J, 5K:
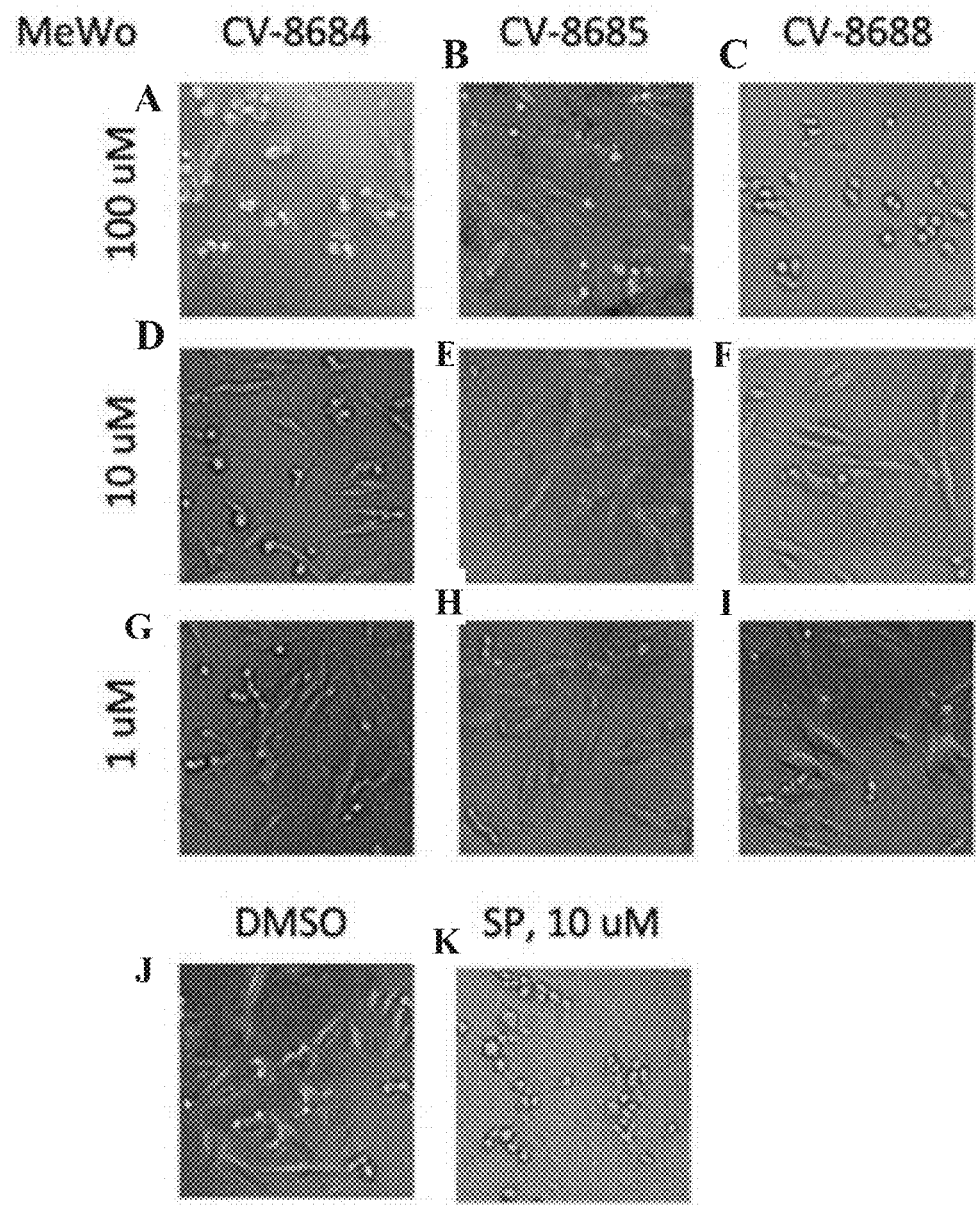
FIGS. 5A-5K are micrographs showing MeWo cell morphology after 6 hours of treatment with various concentrations of CV-8684, CV-8685, CV-8688, DMSO, and staurosporine.
Figures 6A, 6B, 6C, 6D, 6E, 6F, 6G, 6H, 6I, 6J, 6K:
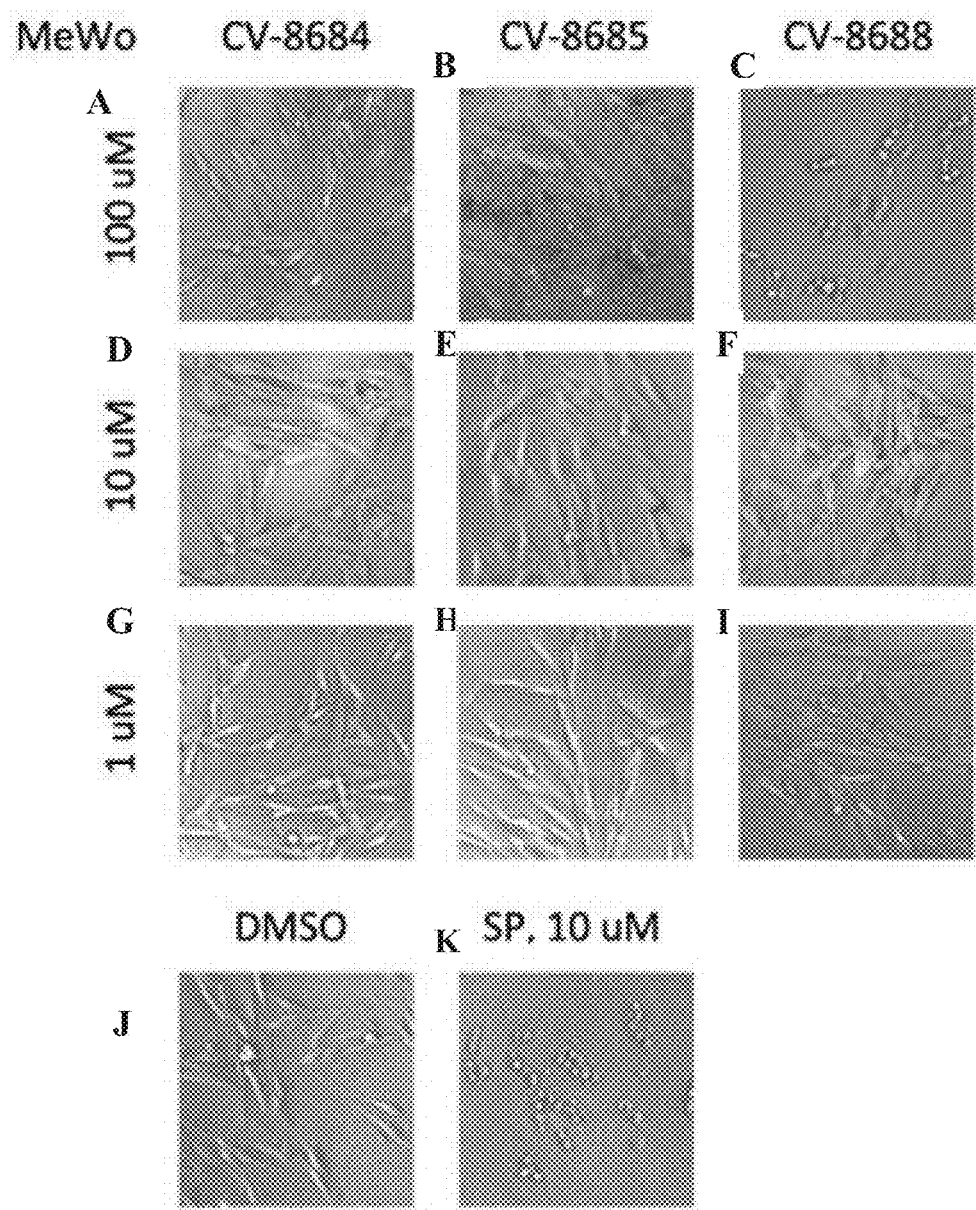
FIGS. 6A-6K are micrographs showing MeWo cell morphology after 24 hours of treatment with various concentrations of CV-8684, CV-8685, CV-8688, DMSO, and staurosporine.
Figures 7A, 7B, 7C, 7D, 7E, 7F, 7G, 7H, 7I, 7J, 7K:
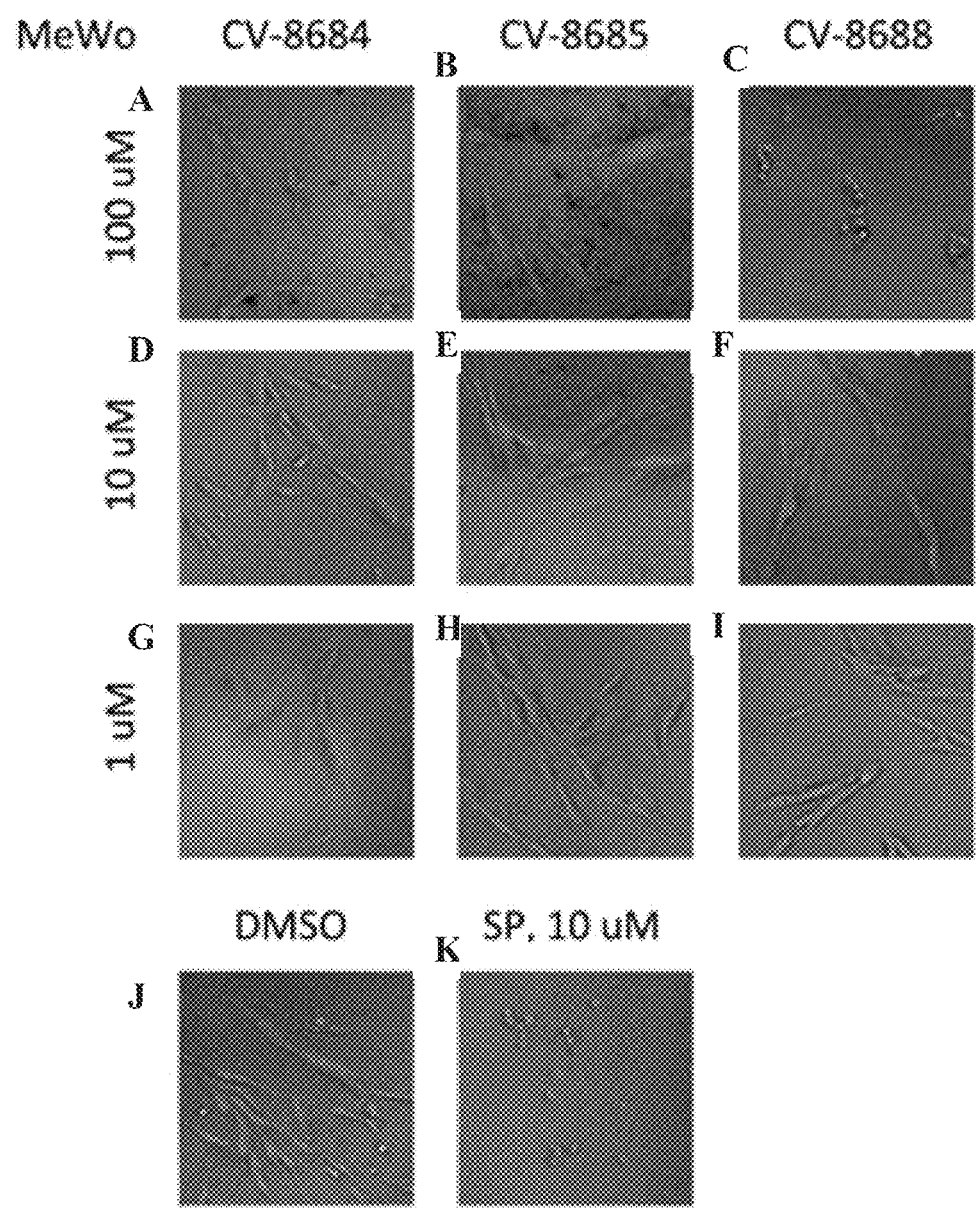
FIGS. 7A-7K are micrographs showing MeWo cell morphology after 48 hours of treatment with various concentrations of CV-8684, CV-8685, CV-8688, DMSO, and staurosporine.
Figures 8A, 8B, 8C, 8D, 8E, 8F, 8G, 8H, 8I, 8J, 8K:
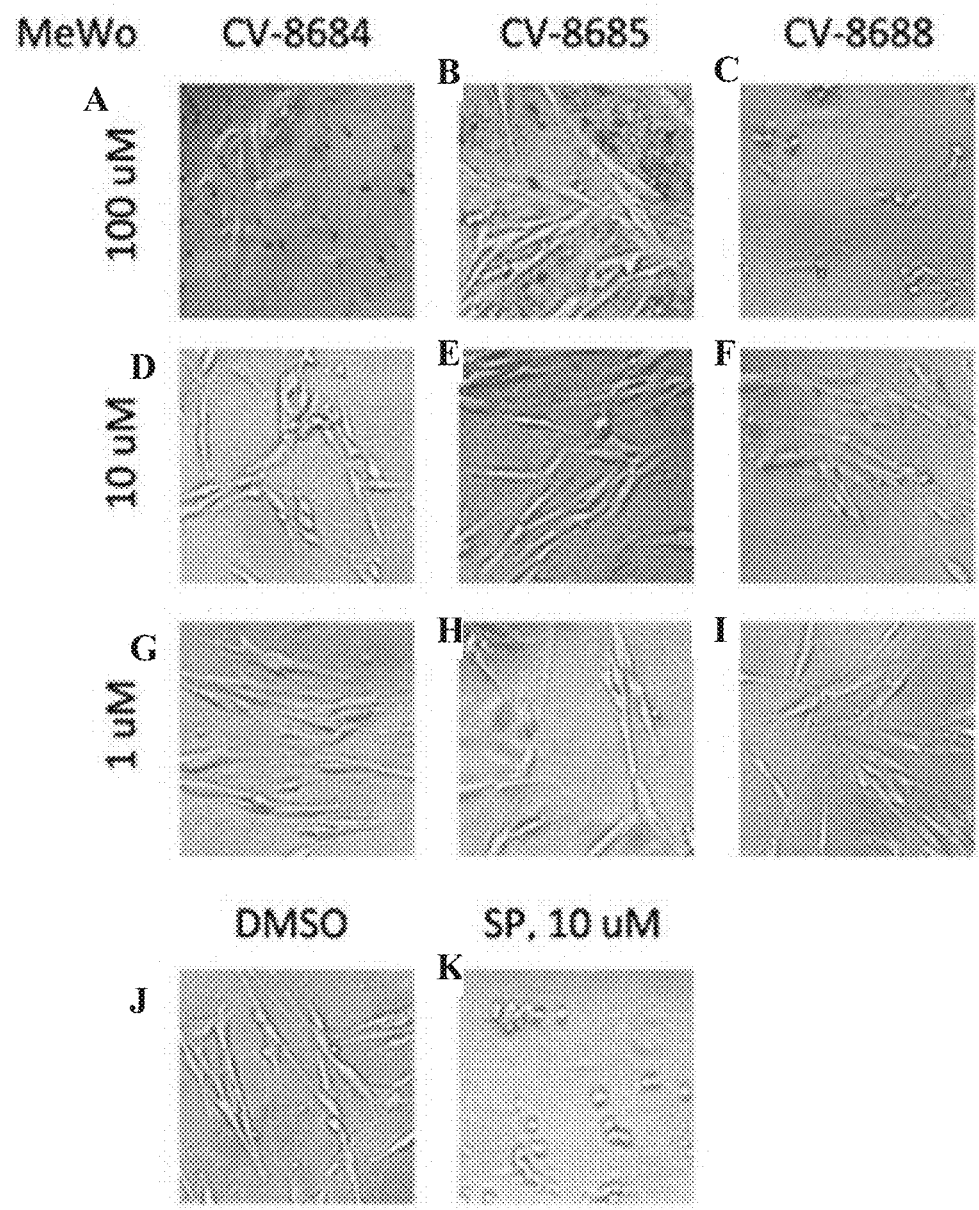
FIGS. 8A-8K are micrographs showing MeWo cell morphology after 72 hours of treatment with various concentrations of CV-8684, CV-8685, CV-8688, DMSO, and staurosporine.
Figures 9A, 9B, 9C, 9D, 9E, 9F, 9G, 9H, 9I, 9J, 9K:
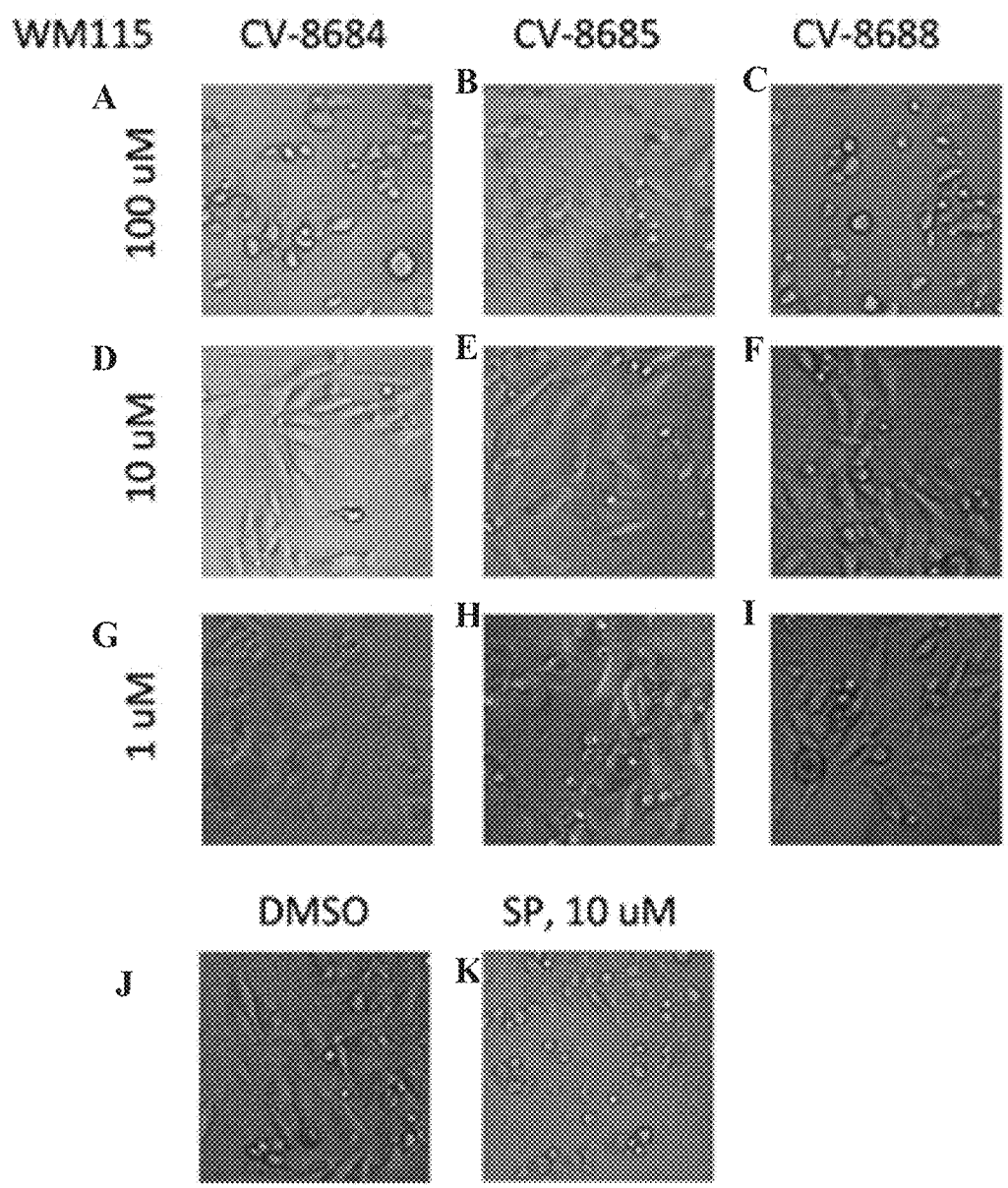
FIGS. 9A-9K are micrographs showing WM115 cell morphology after 6 hours of treatment with various concentrations of CV-8684, CV-8685, CV-8688, DMSO, and staurosporine.
Figures 10A, 10B, 10C, 10D, 10E, 10F, 10G, 10H, 10I, 10J, 10K:
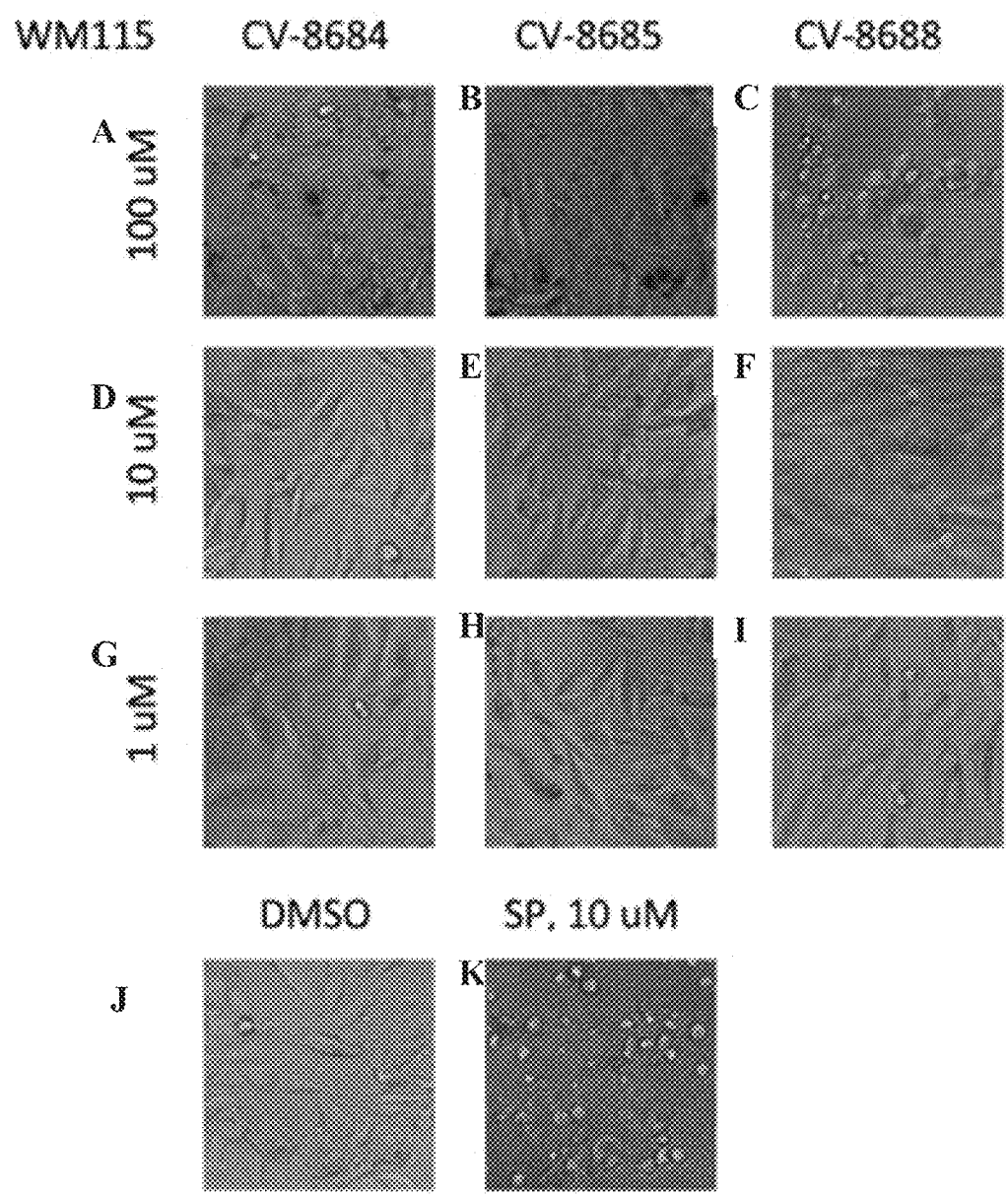
FIGS. 10A-10K are micrographs showing WM115 cell morphology after 24 hours of treatment with various concentrations of CV-8684, CV-8685, CV-8688, DMSO, and staurosporine.
Figures 11A, 11B, 11C, 11D, 11E, 11F, 11G, 11H, 11I, 11J, 11K:
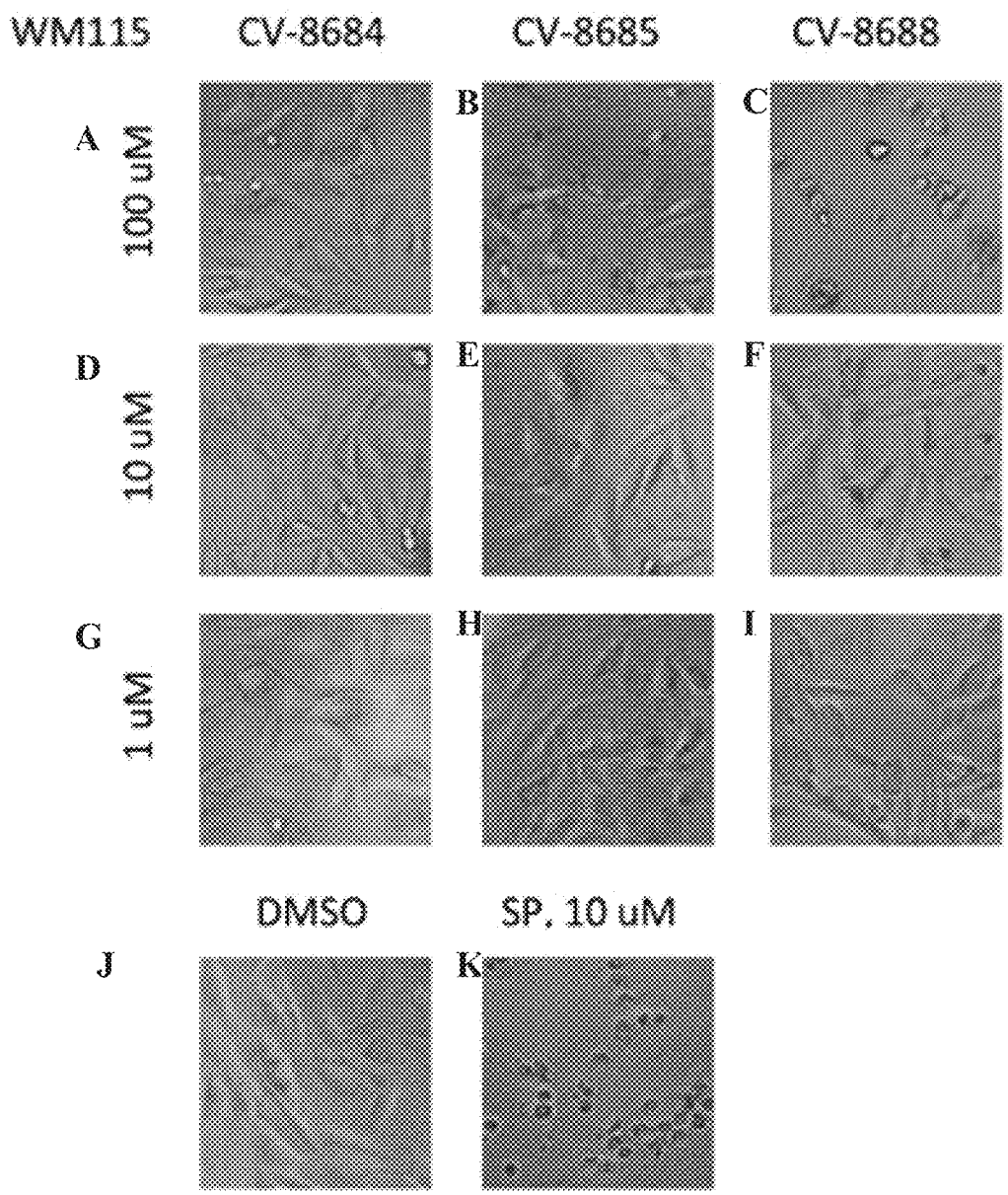
FIGS. 11A-11K are micrographs showing WM115 cell morphology after 48 hours of treatment with various concentrations of CV-8684, CV-8685, CV-8688, DMSO, and staurosporine.
Figures 12A, 12B, 12C, 12D, 12E, 12F, 12G, 12H, 12I, 12J, 12K:
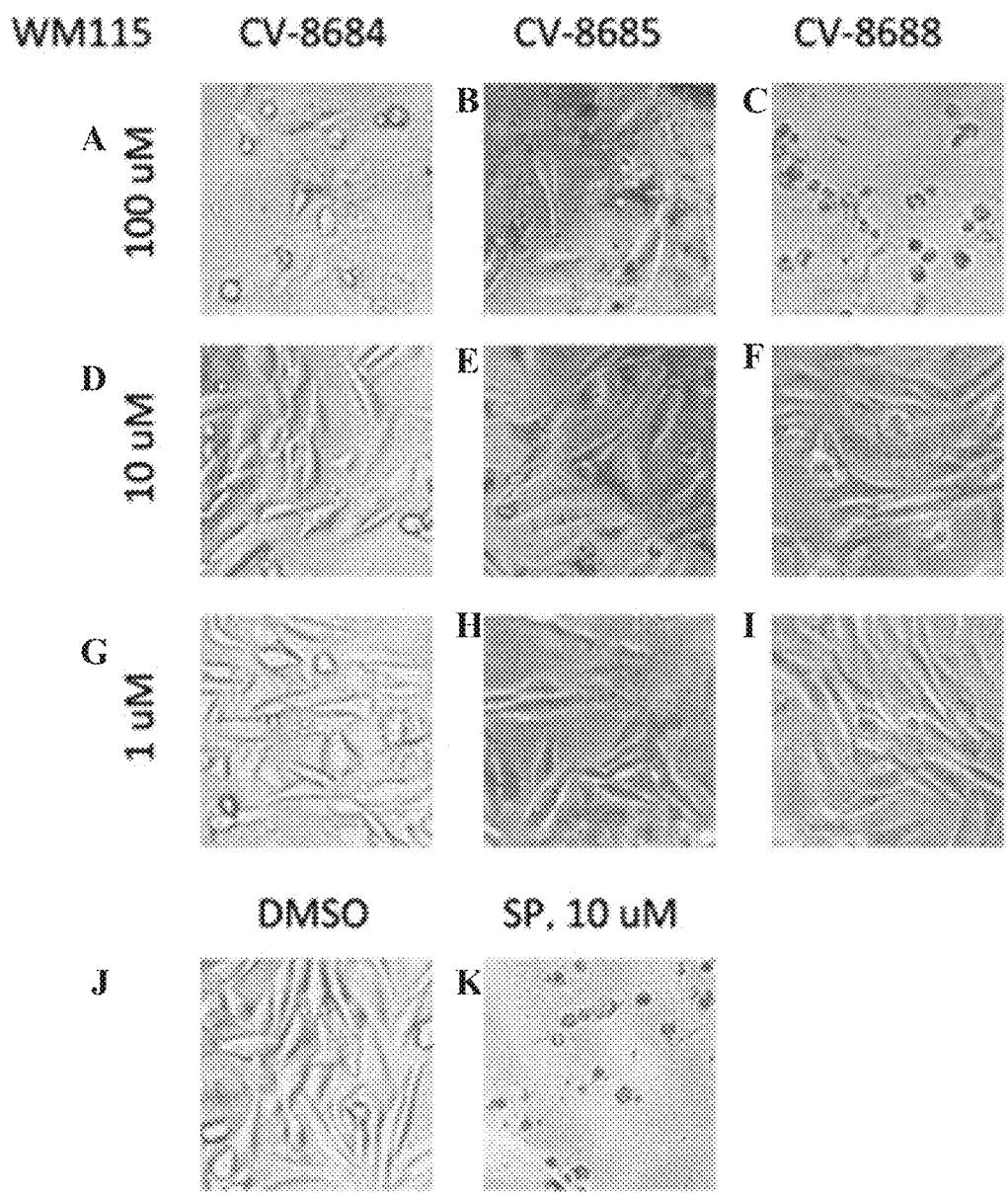
FIGS. 12A-12K are micrographs showing WM115 cell morphology after 72 hours of treatment with various concentrations of CV-8684, CV-8685, CV-8688, DMSO, and staurosporine.
Figures 13E, 13F, 13G, 13H, 13I, 13J:
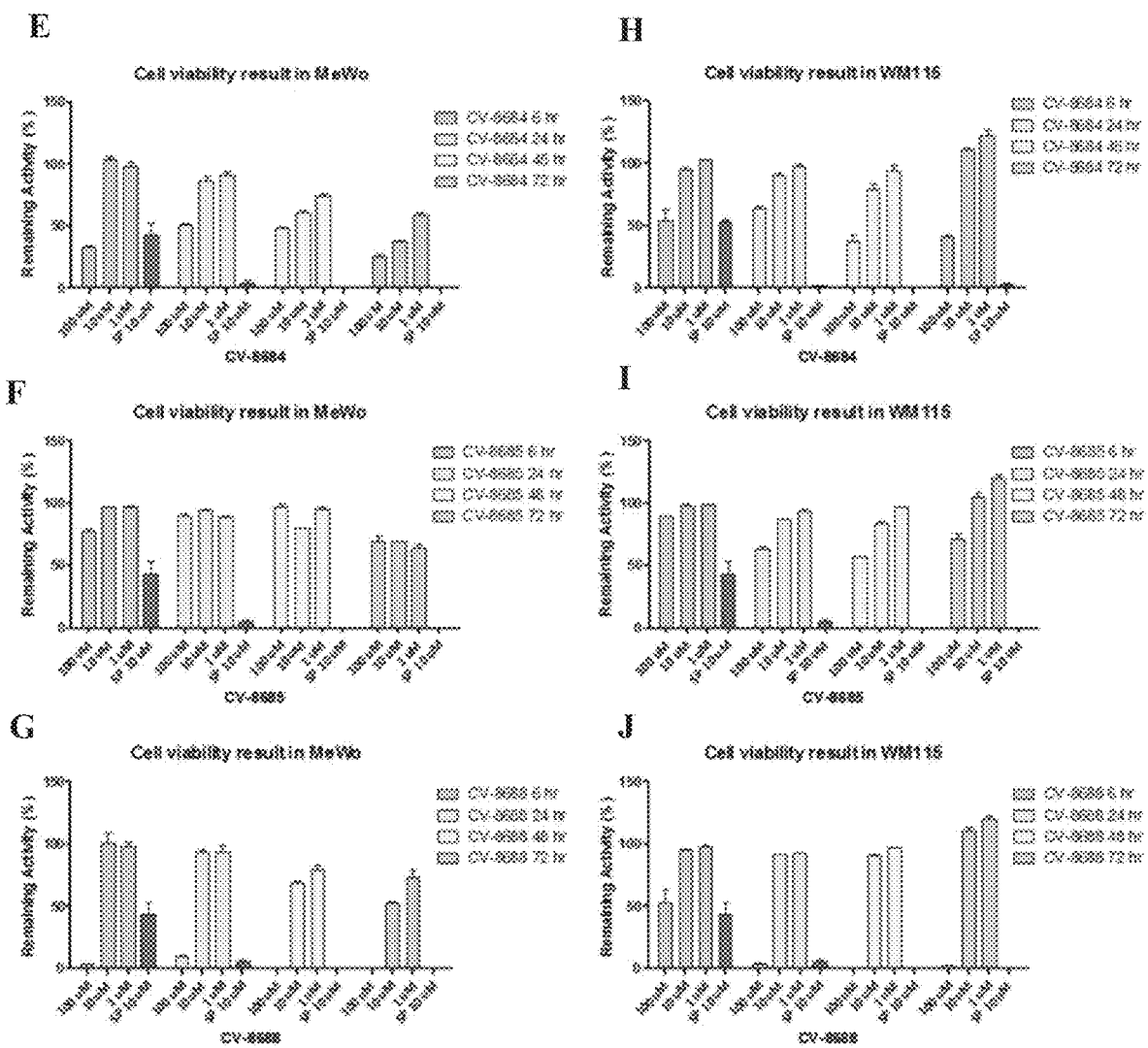
FIGS. 13E-13J are histograms showing results from FIGS. 13A-13D.
Figures 14E, 14F, 14G, 14H, 14I, 14J:
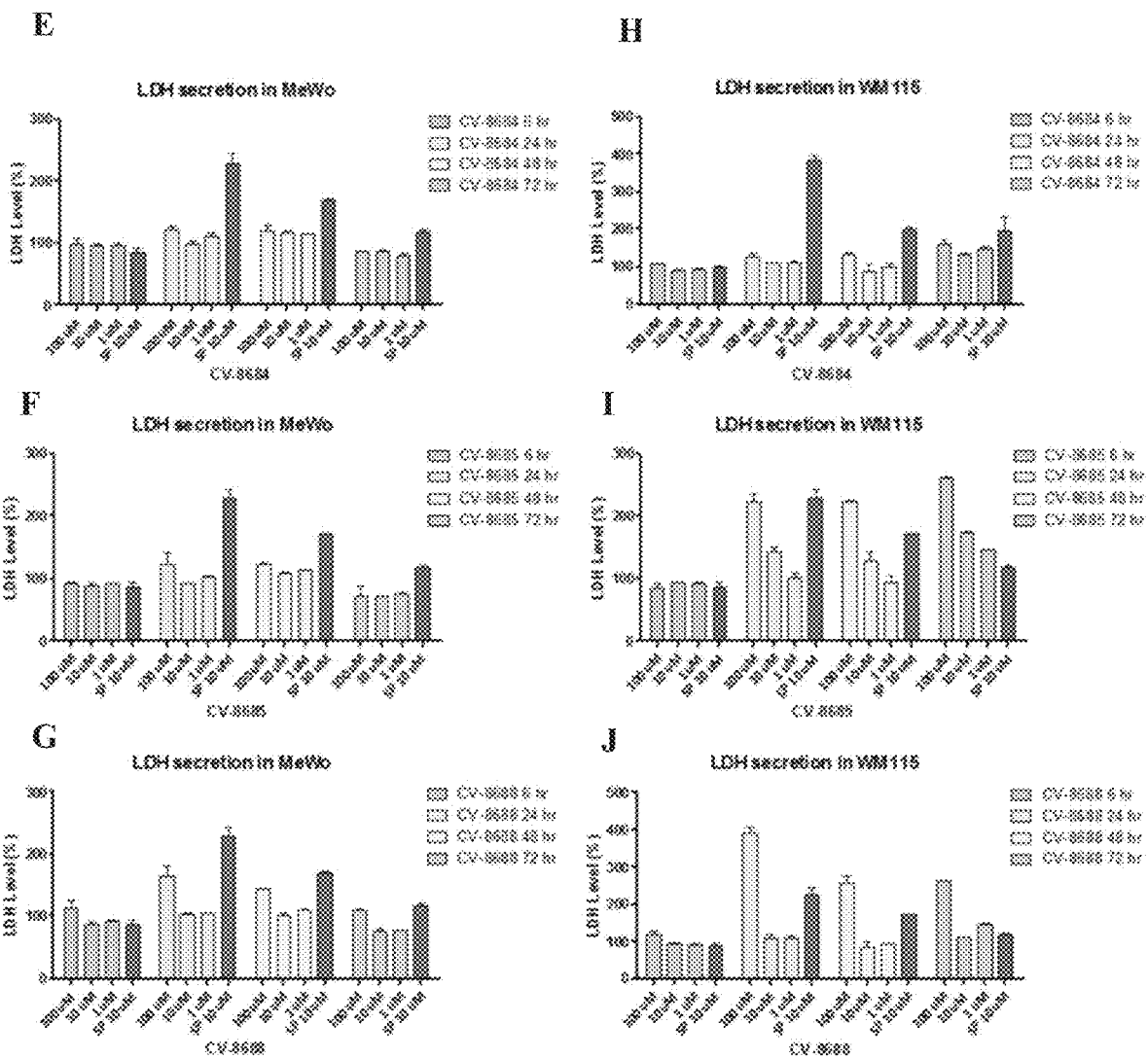
FIGS. 14E-14J are histograms showing results from FIGS. 14A-14D.
Figure 14K:
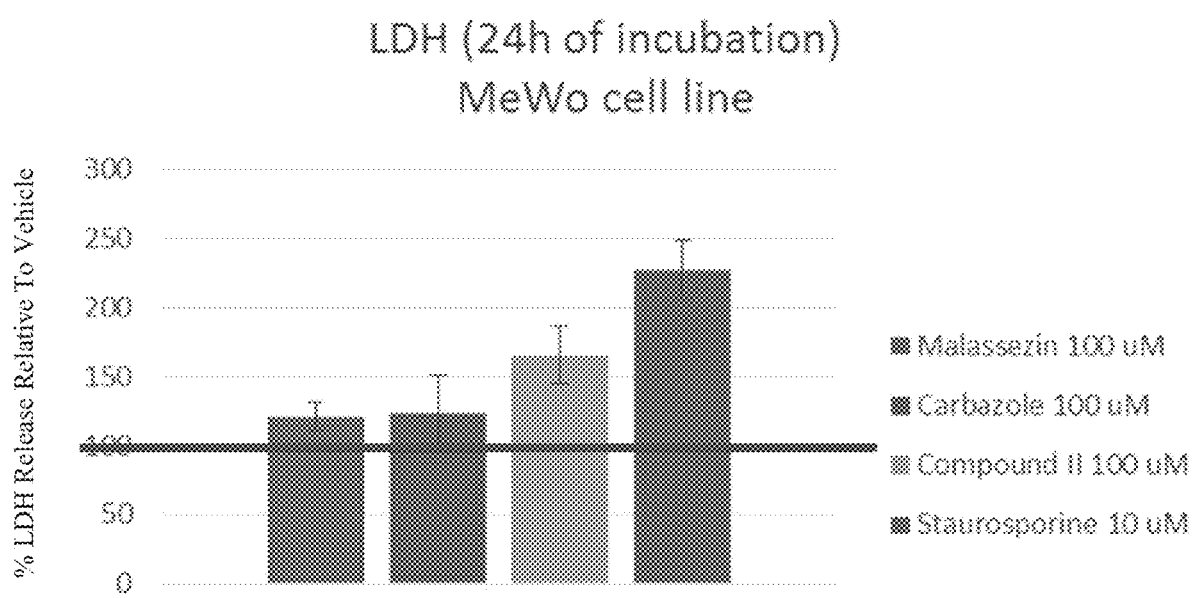
FIGS. 14K and 14L are histograms showing lactate dehydrogenase levels after exposing MeWo (FIG. 14K) and WM115 (FIG. 14L) cells to the listed concentrations of malassezin, carbazole, compound II, and staurosporine for 24 hours.
Figure 14L:
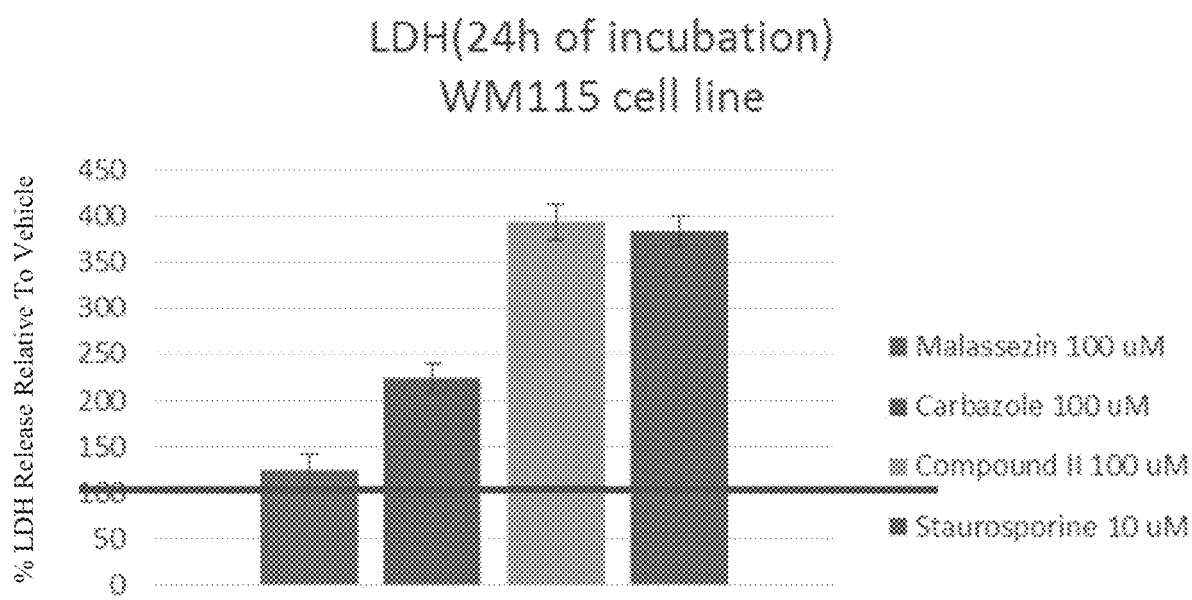
Figure 15A:
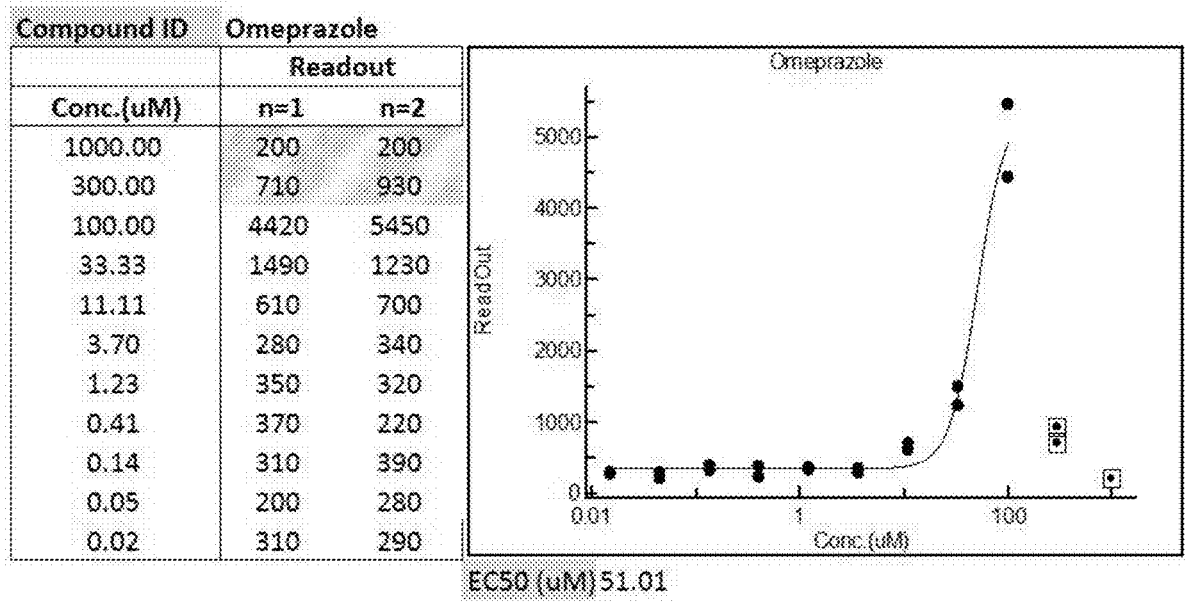
FIGS. 15A-15E show raw data and line graphs of arylhydrocarbon receptor ("AhR") activation in HepG2 cells stably transfected with an AhR-responsive luciferase reporter gene plasmid upon exposure to various concentrations of omeprazole (FIG. 15A), CV-8684 (FIG. 15B), CV-8685 (FIG. 15C), CV-8686 (FIG. 15D), and CV-8688 (FIG. 15E).
Figure 15B:
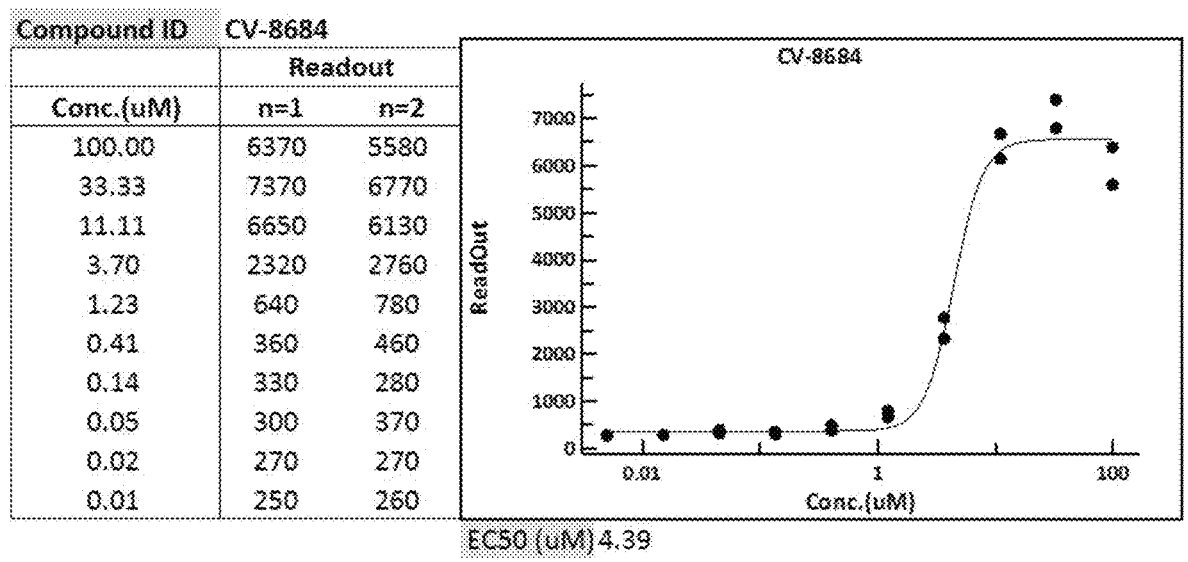
Figure 15C:
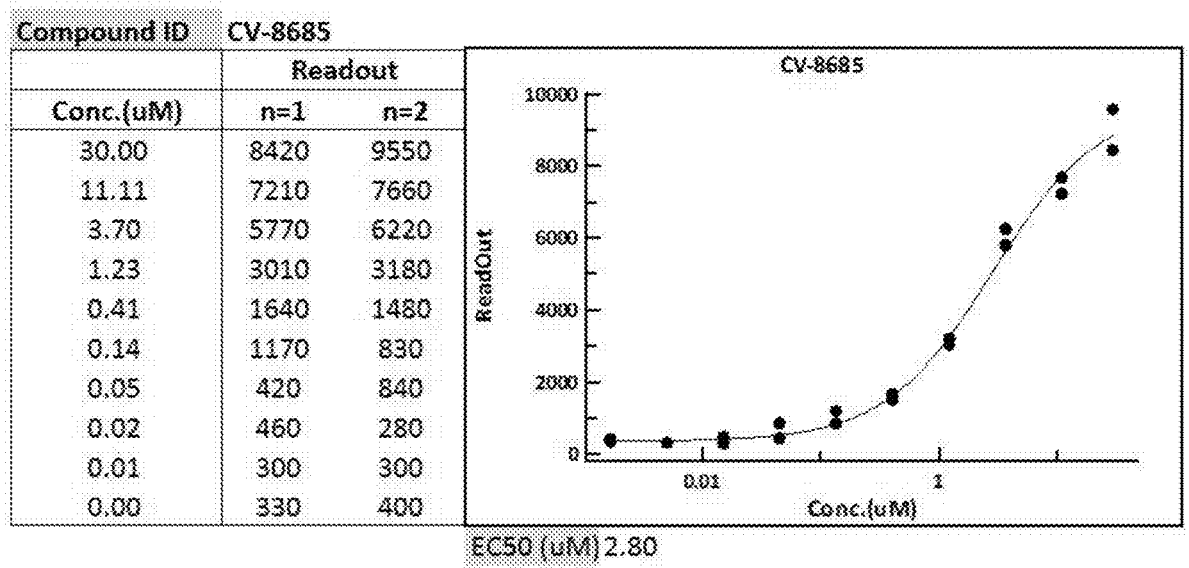
Figure 15D:
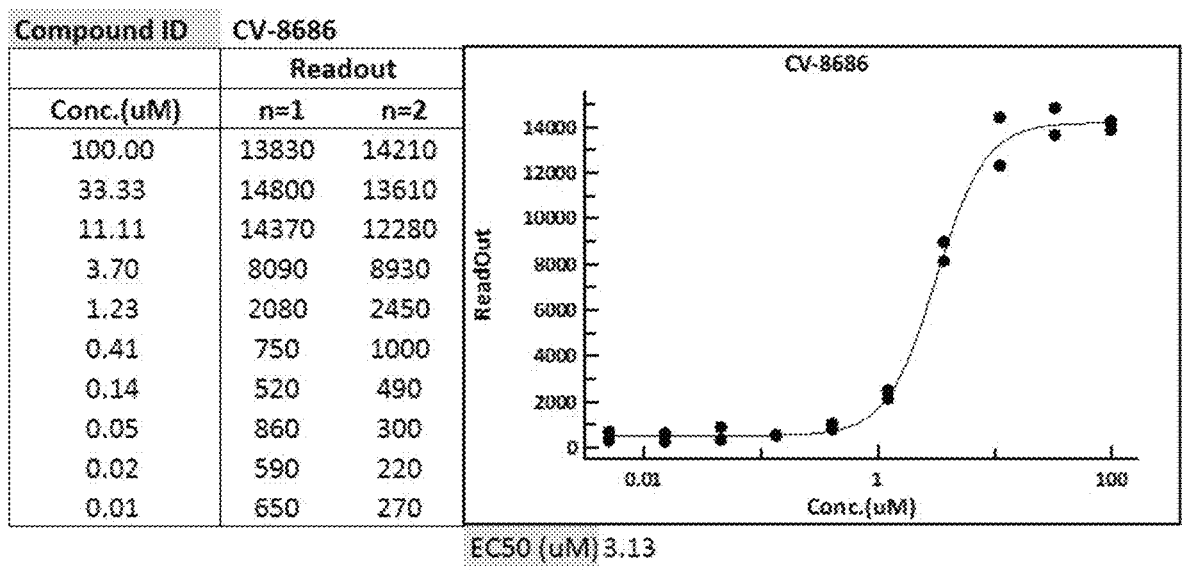
Figure 15E:
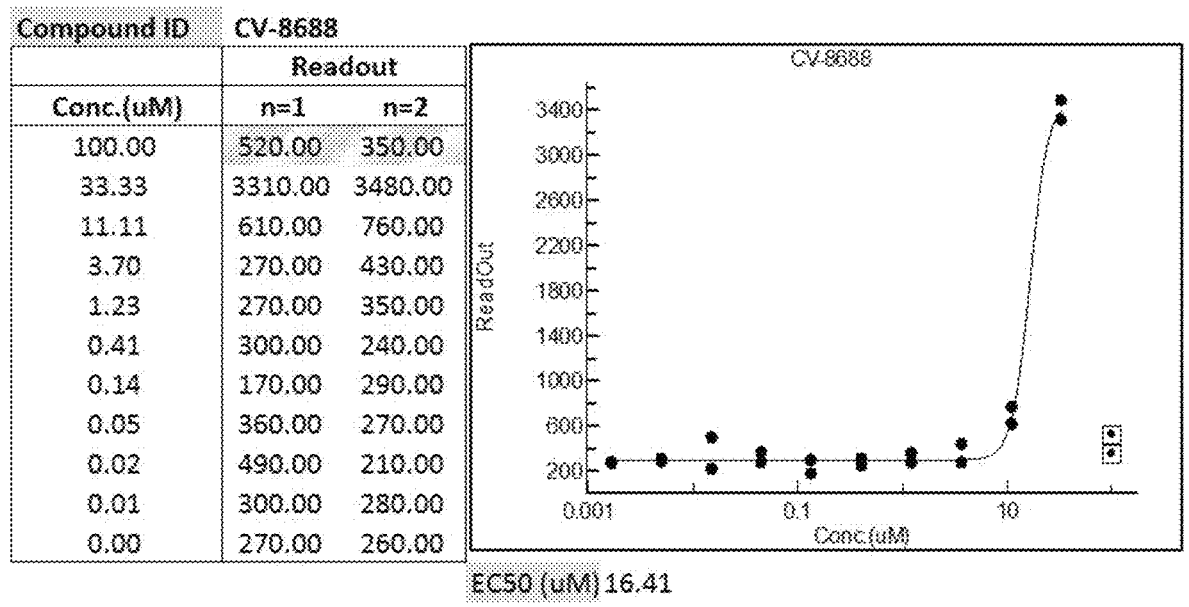
Figure 16A:
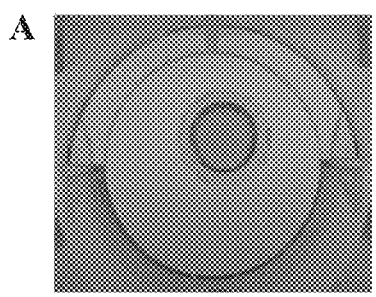
Figure 16B:
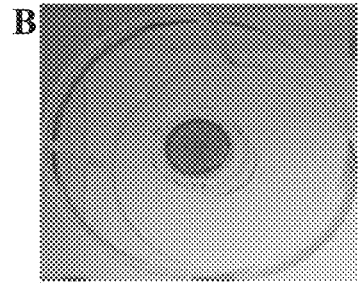
Figure 16C:
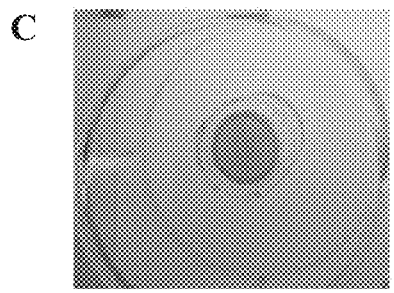
Figure 16D:
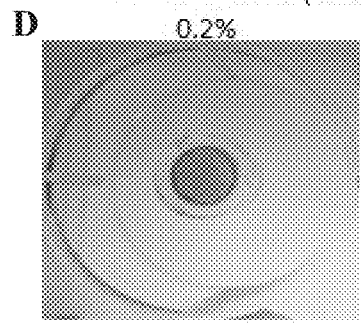
Figure 16E:
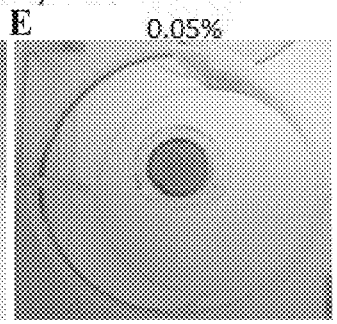
Figures 18A, 18B, 18C, 18D, 18E, 18F:
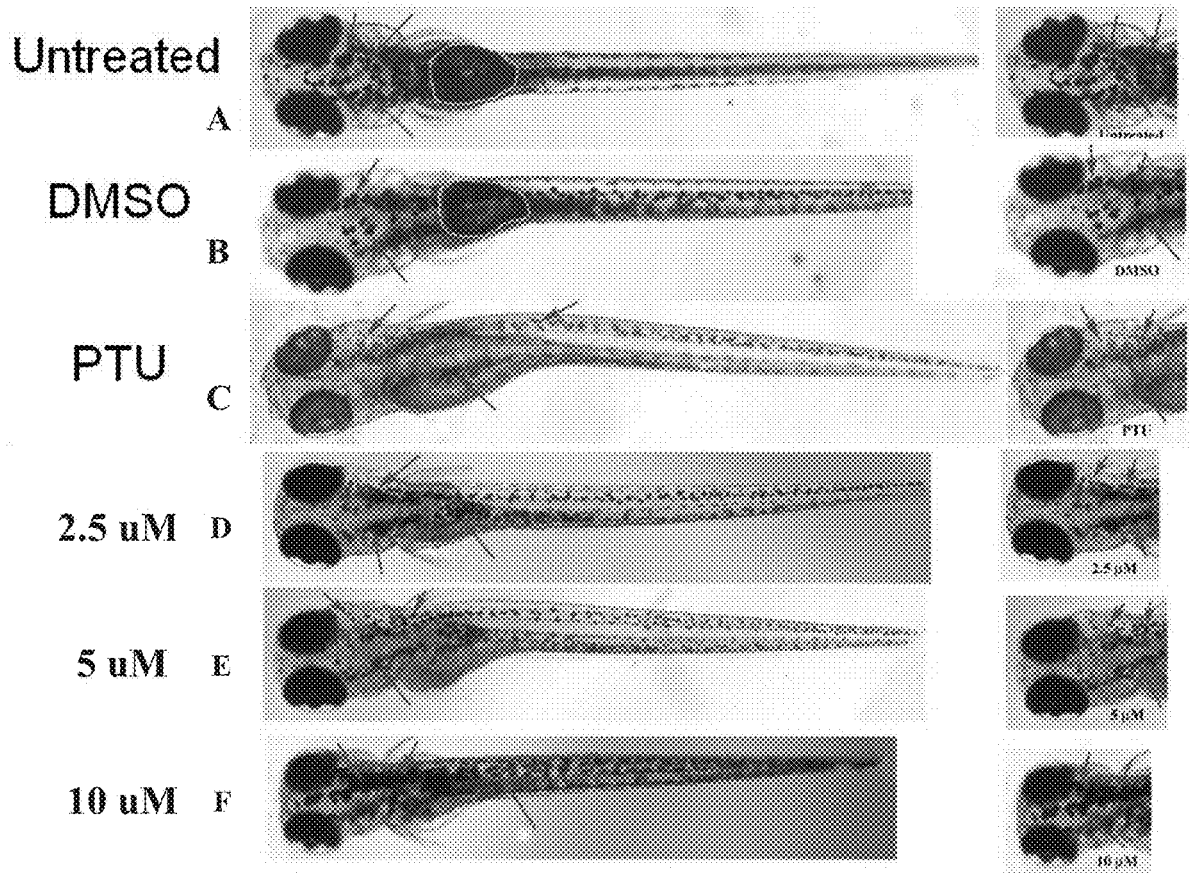
FIGS. 18A-18F are photographs of zebrafish exposed to no treatment (FIG. 18A), DMSO (FIG. 18B), phenylthiourea ("PTU") (FIG. 18C), and compound II at 2.5 µM (FIG. 18D), 5 µM (FIG. 18E), and 10 µM (FIG. 18F). Red arrows indicate normal melanocytes.
Figures 19A, 19B, 19C, 19D, 19E, 19F:
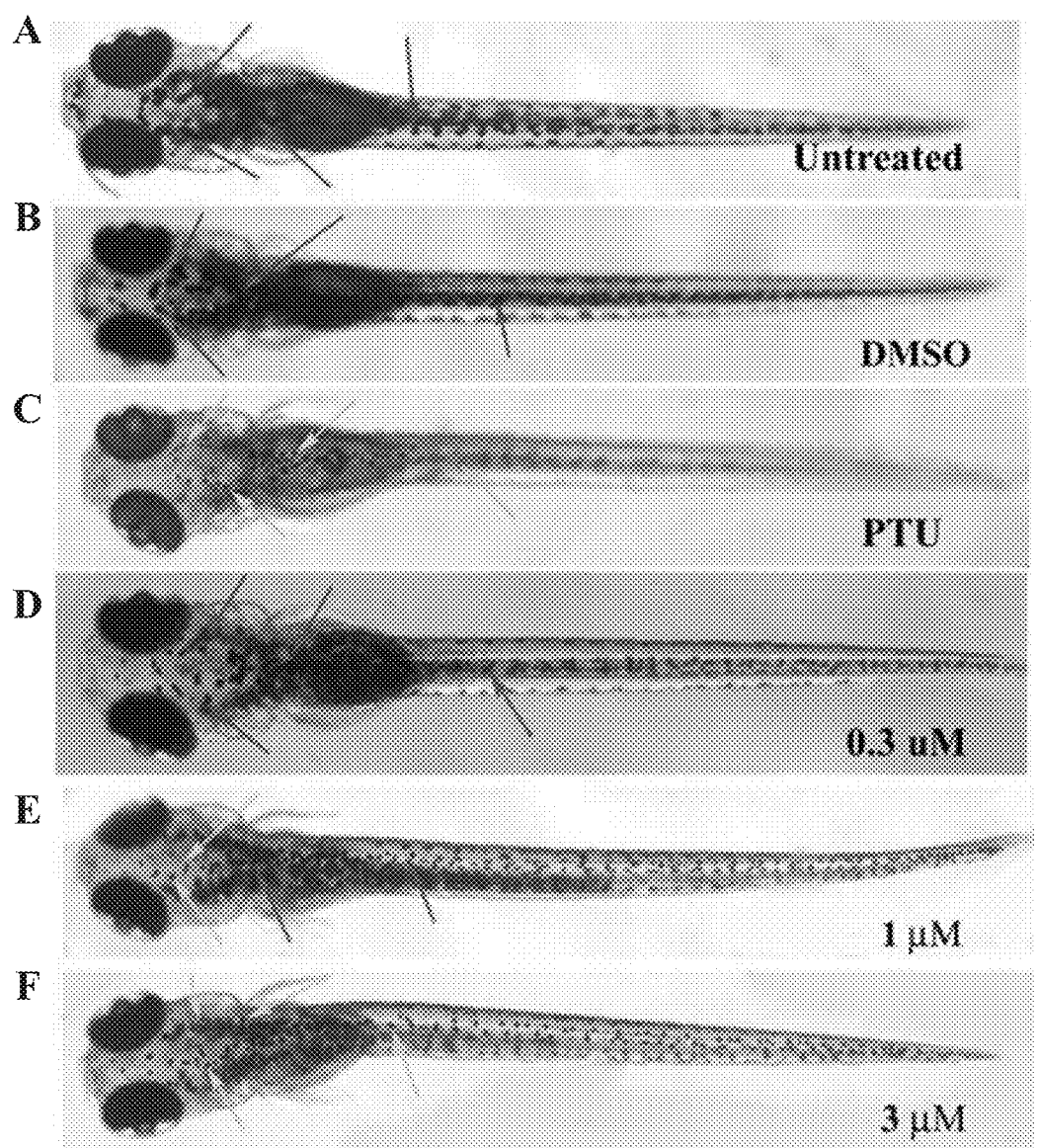
FIGS. 19A-19F are photographs of zebrafish exposed to no treatment (FIG. 19A), DMSO (FIG. 19B), phenylthiourea ("PTU") (FIG. 19C), and compound II at 0.3 µM (FIG. 19D), 1 µM (FIG. 19E), and 3 µM (FIG. 19F). Red arrows indicate normal melanocytes. Yellow arrows indicate abnormally small melanocytes.
Figures 21A, 21B, 21C, 21D, 21E:
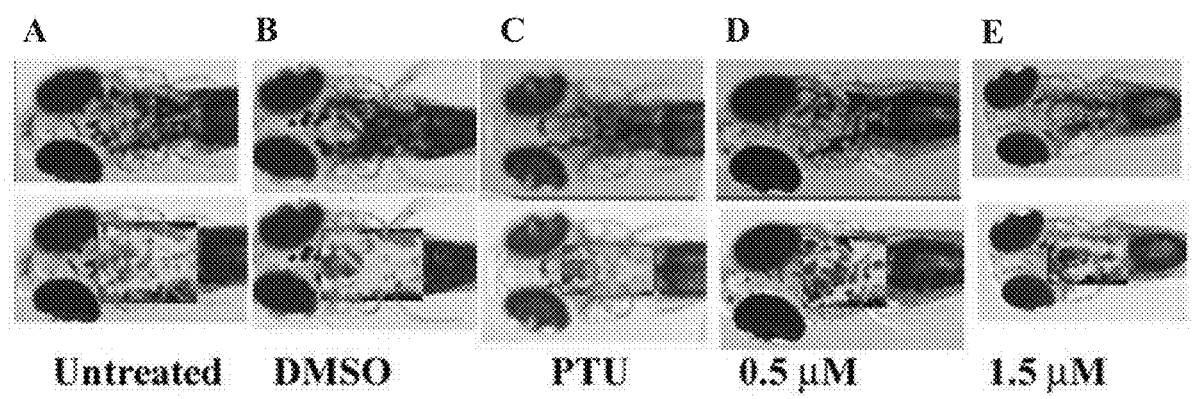
FIGS. 21A-21E are photographs of zebrafish treated with no treatment (FIG. 21A), DMSO (FIG. 21B), PTU (FIG. 21C), 0.5 µM (FIG. 21D), and 1.5 µM (FIG. 21E). Bottom panels include regions of color scheme inversion.
Figure 22A:
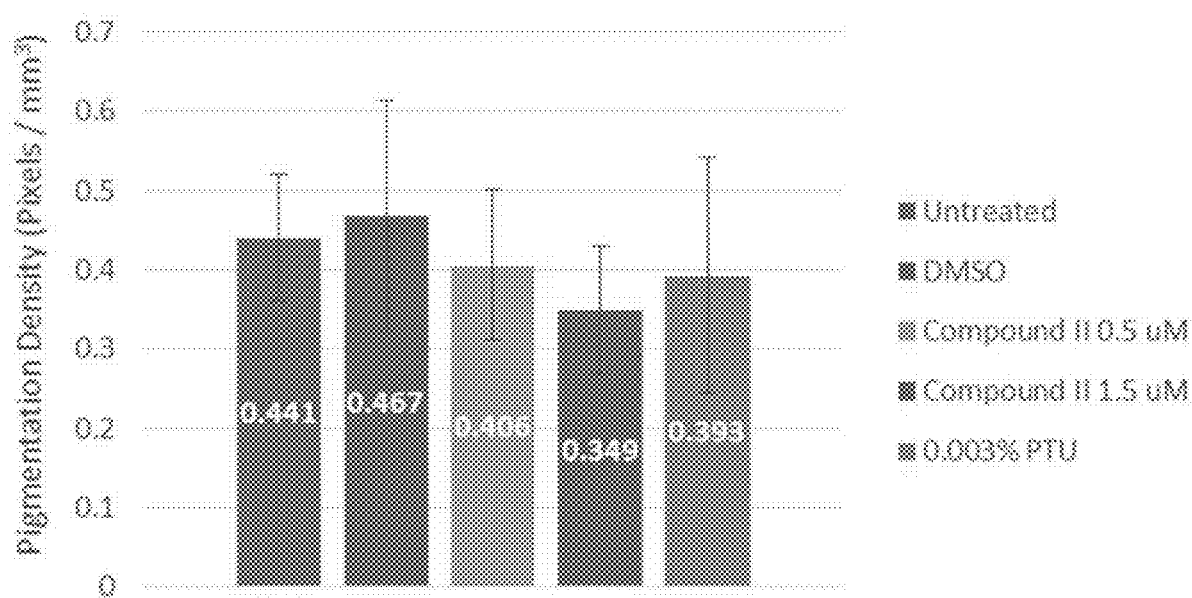
FIGS. 22A and 22B are histograms showing pigmentation density as measured by pigmented pixels/mm$^3$ (FIG. 22A) and total pixels (FIG. 22B) from photographs of zebrafish embryos, exemplified in FIGS. 21A-21E.
Figure 22B:
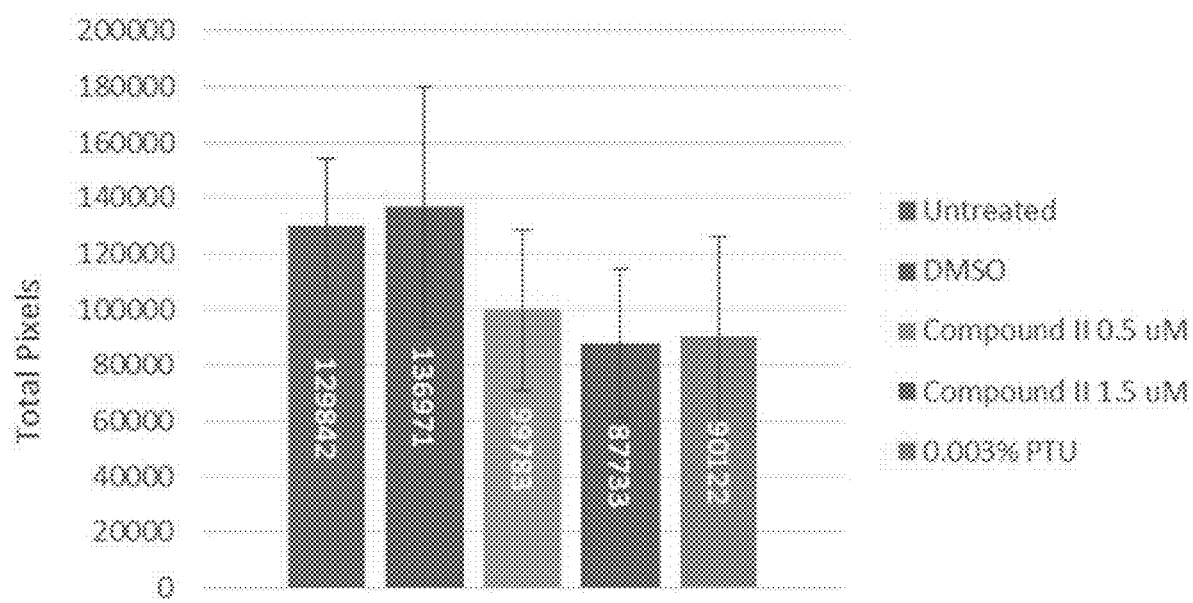
Figures 23A, 23B, 23C:
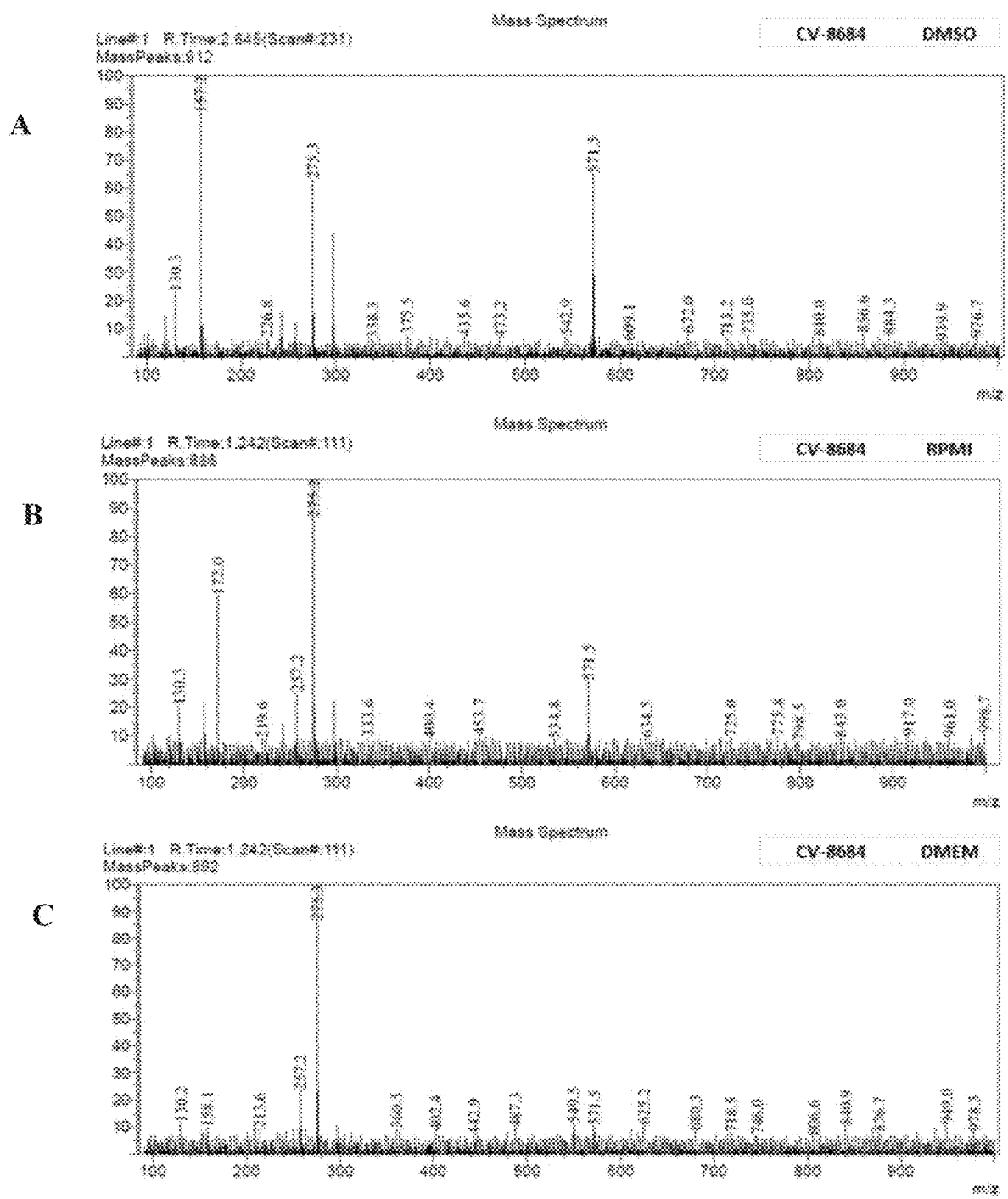
FIGS. 23A-23C are mass spectra of CV-8684 in DMSO (FIG. 23A), RPMI media (FIG. 23B), and DMEM (FIG. 23C).
Figures 23D, 23E, 23F:
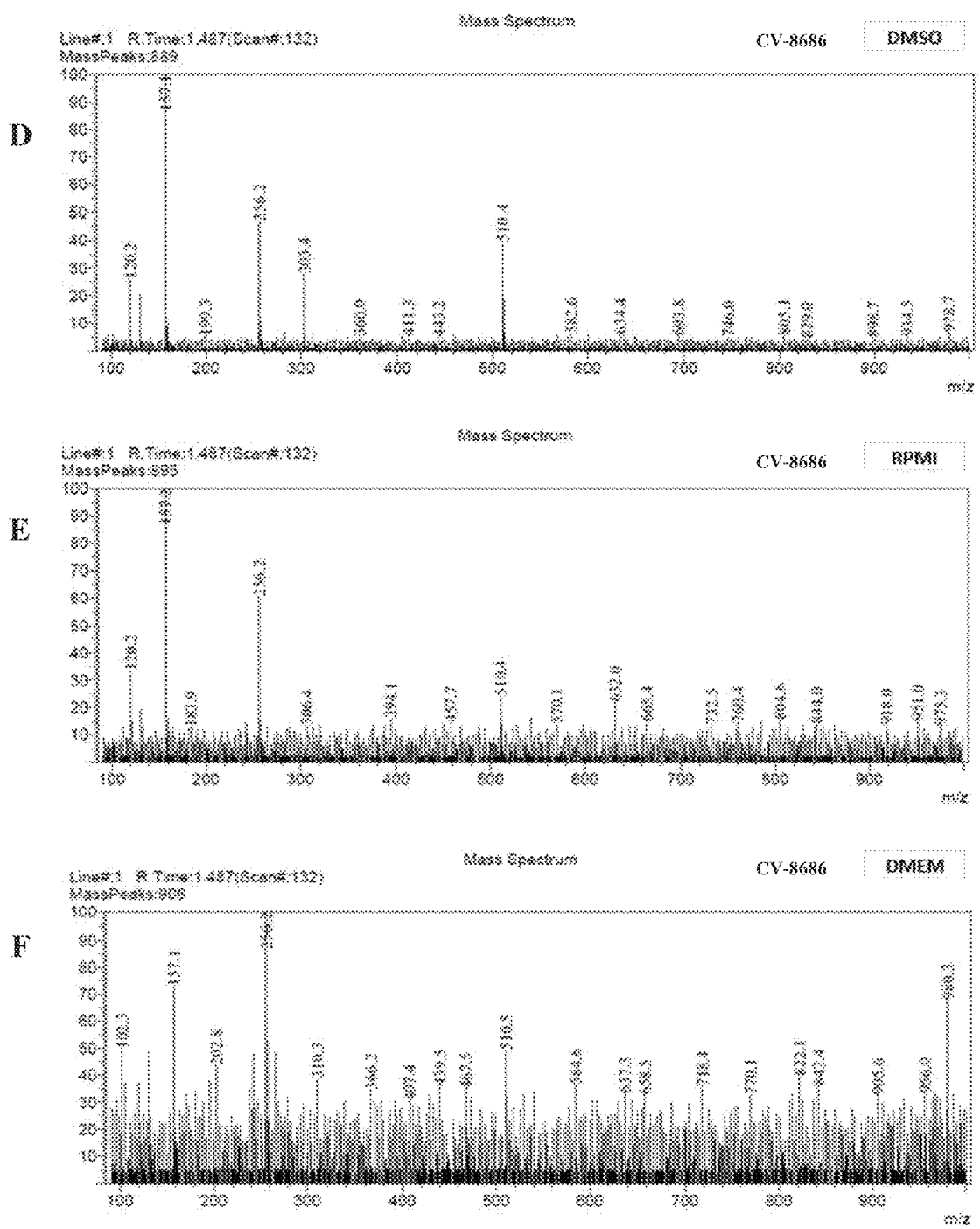
FIGS. 23D-23F are mass spectra of CV-8686 in DMSO (FIG. 23D), RPMI media (FIG. 23E), and DMEM (FIG. 23F).
Figures 23G, 23H, 23I:
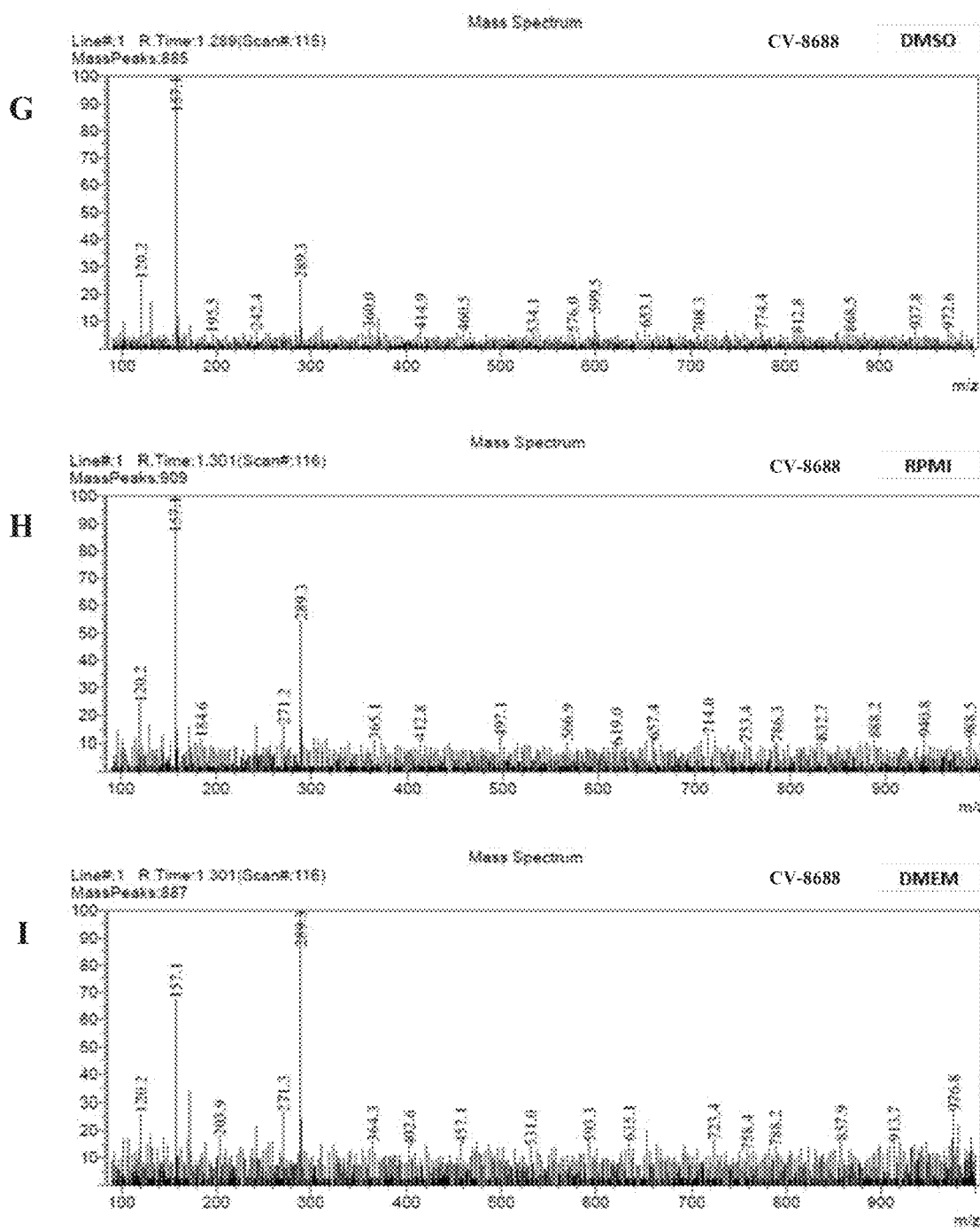
FIGS. 23G-23I are mass spectra of CV-8688 in DMSO (FIG. 23G), RPMI media (FIG. 23H), and DMEM (FIG. 23I).

Compound II ("CV-8688") was synthesized according to the scheme shown in FIG. 2C.

Synthesis of Compound 7

Copper iodide (0.53 g, 10% mol) and $PdCl_2(PPh_3)_4$ (1.0 g, 5% mol) was added to a degassed solution of compound 1 (9.0 g, 0.03 mol), 3-methoxy-1-butyne (2.8 g, 0.035 mol) in triethylamine (150 mL) at ambient temperature. After stirring at ambient temperature over 2 hr. The reaction was complete (monitored by TLC using 10% ethyl acetate/hexanes). The reaction mixture diluted with ethyl acetate (300 mL), reaction mixture was washed with water, saturated NaCl and dried over $Na_2SO_4$. The solvent was filtered and concentrated in vacuo to give as brown oil. The crude compound purified by column chromatography (10% ethyl acetate/hexane). Compound 7 was obtained as a light yellow liquid (7.0 g, 90%).

Synthesis of Compound 8

To an oven-dried flask was added PtCl2 (0.68 g, 0.0025 mol), Na2CO3 (4.0 g, 0.038 mol), indole (6.0 g, 0.05 mol) and compound 7 (10.0 g, 0.025 mol) in dioxane (250 mL). The flask was degassed with nitrogen, sealed and heated to 100° C. overnight. After the reaction was complete (monitored by TLC using 10% ethyl acetate/hexanes). The solvent was evaporated under reduced pressure. The reaction mixture diluted with ethyl acetate (400 mL), reaction mixture was washed with water, saturated NaCl and dried over $Na_2SO_4$. The solvent was filtered and concentrated in vacuo to give as brown oil. Crude compound purified by column chromatography (10% ethyl acetate/hexane). Compound 8 was obtained as a light brown solid (3.5 g, 77%).

Synthesis of Compound 9

Potassium carbonate (3.8 g, 0.027 mol) was added to a solution of compound 8 (3.3 g, 0.0091 mol) in methanol (75 mL) and water (25 mL) mixture at ambient temperature. The resulting suspension was heated to reflux overnight. After the reaction was complete (monitored by TLC using 20% ethyl acetate/hexanes). The reaction mixture was cooled to ambient temperature and solvent concentrated in vacuo. The residue taken in ethylacetate (200 mL) and washed with water and brine then dried (sodium sulfate), filtered, solvent concentrated in vacuo to give as brown solid. Crude compound purified by column chromatography (20% ethyl acetate/hexane). Compound 9 was obtained as an orange color solid (2.1 g, 88%).

Synthesis of Compound Compound II (CV-8688)

To a dried 100 mL two neck round-bottom flask under argon at 0° C. dimethylformamide (20 mL) was added. POCl$_3$ (0.76 g. 0.005 mol) slowly added while maintaining the internal temperature below 5° C. over 10 min. After 30 min stirring at 0° C., a solution of compound 9 (1.3 g, 0.005 mol) in dimethylformamide (5 mL) was slowly added while maintaining the internal temperature below 5° C. over 10 min. The resulting mixture was stirred at ambient temperature overnight. After the reaction was complete (monitored by TLC using 20% ethyl acetate/hexanes). The reaction mixture was poured into saturated aqueous sodium bicarbonate (150 mL) and stirred for 1 hr. Resulting mixture was extracted with ethyl acetate (2×100 mL). The organic layers were combined and washed with water, saturated NaCl and dried over $Na_2SO_4$. The solvent was filtered and concentrated in vacuo to give as brown solid. The crude compound crystallized in chloroform (25 mL). Compound II (CV-8688) was obtained as a light pink solid (0.81 g, 53%).

HPLC purity: 98.94% (area %). $^1$H-NMR, $^{13}$C spectrum consistent with the structure. ESI-MS: Calc. for $C_{19}H_{17}N_2O$ (M+H)$^+$: 289, found: 289.0.

Example 6

Cell Morphology

Typical cell morphology after various treatments is shown in FIGS. 5A-5K, 6A-6K, 7A-7K, 8A-8K, 9A-9K, 10A-10K, 11A-11K, and 12A-12K. The morphology of both cell lines was significantly affected by 100 μM of CV-8684 and CV-8688, as well as staurosporine treatment at 6 hours. CV-8685 appeared to only affect WM115 at 100 μM.

Example 7

Apoptosis-Inducing Activity of Malassezin and Malassezin Derivatives—Preliminary Annexin V Assays Materials and Reagents Annexin V-FITC assay kit was purchased from Beyotime Biotechnology, RPMI 1640 medium and Dulbecco's modified Eagle medium ("DMEM") were purchased from Gibco, fetal bovine serum ("FBS") was purchased from Invitrogen, stabilized antibiotic antimycotic solution (100×) was purchased from Sigma, and 0.25% trypsin-EDTA (1×), phenol red was purchased from Invitrogen.

Cell Culture

MeWo (ATCC® HTB-65™) and WM115 (ATCC® CRL-1675) cells were purchased from ATCC (Manassas, VA) and maintained in the following: for MeWo: DMEM supplemented with 10% FBS; for WM115: RPMI 1640 supplemented with 10% FBS (10% FBS, 1% stabilized antibiotic anti-mycotic solution).

Study Summary

In the intermediate stages of apoptosis, phosphatidylserine ("PS") is translocated from the inner to the outer leaflet of the cell membrane, exposing PS to the extracellular environment, where it can be detected. Highly fluorescent annexin V conjugates provide quick and reliable detection methods for studying the externalization of PS.

During the first set of studies, both MeWo and WM115 cells were treated with test compounds at 10 doses starting from 100 μM with 3-fold dilution. Staurosporine was used as positive control. After 6-hour treatment, cell apoptosis was assessed using an annexin V assay. The test compounds evaluated were CV-8684, CV-8685, CV-8686, CV-8687, and CV-8688.

Assay Procedures

For cell seeding, cells were harvested and the cell number was determined using Countess® cell counter. Cells were then diluted with culture medium to the desired density. 40 μL of cell suspension per well was added to the required number of wells in a 384-well plate (Corning 3712—clear bottom plate). The final cell density was 6,000 cells/well. After plating, the plates were incubated at 37° C. and 5% $CO_2$ overnight.

For preparation of compound source plate, each test compound was dissolved in DMSO to 10 mM stock. 3-fold serial dilution was performed using an EVO200™ liquid handler (TECAN) to generate ten concentrations of test compound. 0.1% DMSO was employed as vehicle (negative) control. The compound source plate was then spun at room temperature at 1,000 RPM for 1 minute and agitated using a plate shaker for 2 minutes.

For compound treatment, 40 nL of compound were transferred from the compound source plate to the 384-well culture plate using liquid handler Echo550 (LabCyte Inc.). After 6-hour incubation, the plates were removed from the incubator for detection.

For the preliminary annexin V assay, the plates were removed from the incubator and allowed to equilibrate at room temperature for 15 minutes. Culture media was then removed. 20 µL of pre-mixed annexin V-FITC and Hoechst33342 dye working solution were added to each well. The cells were then incubated at room temperature for 20 minutes. The plates were sealed and centrifuged for 1 minute at 1,000 RPM to remove bubbles. Afterward, the plate was read using an Acumen eX3 plate reader. The relative activity was calculated according to the following formula: Activity (%)=100%×(Count$_{Annexin\ v}$/Count$_{Total\ cell}$), and $EC_{50}$ was calculated using Graph Pad Prism (v. 5.01).

Results

In the preliminary screen discussed above, CV-8688 markedly increased annexin V staining of MeWo cells, with an $EC_{50}$ of 908.57 nM. Staurosporine, the positive control, greatly increased annexin V staining in both cell lines. (FIGS. 3A-3M).

Example 8

Apoptosis-Inducing Activity of Malassezin and Malassezin Derivatives—Additional Evaluation Using Annexin V Assays Study Summary To further investigate the impact of test compounds on apoptosis, multiple readouts, covering different stages of apoptosis, were carried out on both MeWo and WM115 cells. Both cell types were treated with test compounds at 3 doses (100 µM, 10 µM, and 1 µM). Staurosporine was used as a positive control. After the desired treatment period (6, 24, 48, or 72 hours), apoptosis was assessed by measuring percentages of cells demonstrating annexin V binding after exposure to the test compounds. The test compounds evaluated were CV-8684, CV-8685, and CV-8688.

Assay Procedures

Cell seeding was performed as discussed above with the following exceptions: the final cell density was 4,000 cells/well for 6-hour and 24-hour detections, whereas 2,000 cells/well were used for 48-hour and 72-hour detections. For each time point, 384-well clear bottom plates (Corning 3712) and solid white bottom plates (Corning 3570) were prepared. The plates were incubated as discussed above.

For preparation of the compound source plate, each test compound was dissolved in DMSO to 10 mM stock. Two additional concentrations were generations by 10-fold dilution to 1 mM and 0.1 mM. Staurosporine was used as positive control and 1% DMSO was employed as vehicle (negative) control. The compound source plate was spun at room temperature at 1,000 RPM for 1 minute and agitated using a plate shaker for 2 minutes.

400 nL of test compound was transferred from the compound source plate to 384-well culture plates using Echo550 liquid handler. After 6, 24, 48, and 72 hours, the plates were removed from the incubator for detections.

For the annexin V assay, plates were removed from the incubator and equilibrated at room temperature for 15 minutes. Culture media was removed and cells were washed twice with PBS. 20 µL of pre-mixed annexin V-FITC working solution was added to each well. The cells were incubated at room temperature for 20 minutes. Plates were read using Acumen eX3 to count the number of FITC-positive cells. The relative activity was calculated according to the following formula: Relative Activity (%)=100%× (Count$_{sample}$/Count$_{vehicle}$).

Results

CV-8684 induced apoptosis at the highest concentration tested after 6 hours of treatment on both MeWo and WM115 cells. CV-8685 showed the induction effect with 24 hours of treatment on WM115, whereas 48 hours of treatment appeared to elicit apoptosis in both cell types. Finally, CV-8688 showed the induction effect within 6 hours of treatment in a dose-dependent manner in both cell types. (FIGS. 4A-4L).

Example 9

Cell Viability After Exposure to Malassezin and Malassezin Derivatives—CellTiter-Glo® Assays Assay Procedures CellTiter-Glo® 2.0 assay was purchased from Promega. Cell seeding, preparation of the compound source plate, and exposure of cells to test compounds were performed as described in Example 8.

For the CellTiter-Glo® assay, plates were removed from the incubator and equilibrated at room temperature for 15 minutes. CellTiter-Glo® reagents were thawed and equilibrated to room temperature before the experiment. 40 µL of CellTiter-Glo® reagent was then added to each well for detection (at 1:1 ratio to culture medium). The plates were then incubated at room temperature for 30 minutes and read using EnSpire (PerkinElmer) plate reader. The remaining activity was calculated according to the following formula: Remaining Activity (%)=100%×(Lum$_{sample}$−Lum$_{bkg}$)/ (Lum$_{vehicle}$−Lum$_{bkg}$).

Results

CV-8684 showed dose-dependent inhibition of cell viability in both cell lines tested, though the inhibitory effect appeared to be more potent in MeWo cells. CV-8685 exhibited the inhibitory effect on WM115 cell viability in a dose-dependent manner only after 24-hour treatment. CV-8688 inhibited viability of both cell types in a dose-dependent manner. Staurosporine, the positive control, exerted 100% inhibition of cell viability in both cell lines after 24-hour treatment. (FIGS. 13A-13K).

Example 10

Cytotoxicity of Malassezin and Malassezin Derivatives—Lactate Dehydrogenase Release Assays Study Summary The LDH assay quantitatively measures lactate dehydrogenase ("LDH") released into the media from damaged cells as a biomarker for cytotoxicity and cytolysis.

Assay Procedures

CytoTox-ONE™ Homogenous Membrane Integrity Assay was purchased from Promega. Cell seeding, preparation of the compound source plate, and exposure of cells to test compounds were performed as described in Example 8.

For the LDH release assay, plates were removed from the incubator and equilibrated at room temperature for 15 minutes. Plates were then centrifuged at 1,000 RPM for 1 minute. 20 μL of cell culture medium was transferred into a new 384-well black solid plate. Then, 20 μL of CytoTOX-ONE™ was added into each well and incubated at room temperature for 10 minutes. Afterward, 10 μL of stop solution were added to each well, and the plates were agitated at 500 rpm for 1 minute. Plates were read using an excitation wavelength of 560 nm and an emission wavelength of 590 nm on EnSpire. The relative activity was calculated according to the following formula: Relative Activity (%)=100%×($Lum_{sample}$−$Lum_{bkg}$)/($Lum_{vehicle}$−$Lum_{bkg}$).

Results

CV-8684 did not induce significant release in either cell line after 72-hour incubation. CV-8685 showed a dose-dependent induction effect on LDH release from WM115, but not MeWo, cells after 24-hour treatment. CV-8688 induced LDH release at the highest concentration tested. (FIGS. 14A-14L).

Example 11

Arylhydrocarbon Receptor Activation Potential of Malassezin and Malassezin Derivatives Assay Procedures HepG2-AhR-Luc cells were purchased from Pharmaron, One-Glo Luciferase assay system was purchased from Promega, DMEM was purchased from Hyclone, and penicillin/streptomycin was purchased from Solabio.

Culture media for stably transfected HepG2 cells was prepared by supplementing DMEM with high glucose and L-glutamine, as well as 10% FBS.

HepG2-AhR-Luc cells were cultured in T-75 flasks at 37° C., 5% $CO_2$, and 95% relative humidity. Cells were allowed to reach 80-90% confluence before detachment and splitting.

Cultivated cells were rinsed with 5 mL PBS. PBS was aspirated away, 1.5 mL trypsin was added to the flask, and cells were incubated at 37° C. for approximately 5 minutes or until the cells detached and floated. Trypsin was inactivated by adding excess serum-containing media.

The cell suspension was transferred to a conical tube and centrifuged at 120 g for 10 minutes to pellet the cells. Cells were resuspended in seeding media at a proper density. 40 μL of cells were transferred to a 384-well culture plate ($5×10^3$ cells/well). Plates were placed in the incubator at 37° C. for 24 hours.

Afterward, stock solutions of test compounds and omeprazole positive control were prepared. 40 nL of compound solutions were transferred into the assay plate using Echo550. The plate was then placed back into the incubator for compound treatment.

Later, after 24 hours of treatment, the plate was removed from the incubator and allowed to cool at ambient temperature. 30 μL One-Glo reagent equal to that of the culture medium was added in each well. Cells were allowed to lyse for at least 3 minutes, and then measured in a luminometer.

Dose responses were graphed using the non-linear regression analysis in XLfit, and $EC_{50}$ values were also calculated.

Results

AhR-Luciferase assay results are shown in FIGS. 15A-15F.

Example 12

MelanoDerm™ Assays

Study Summary

The purpose of this study is to evaluate the potential dermal irritation of the test article to the MelanoDerm™ Skin Model after repeated exposures for dose selection for a subsequent study. Toxicity will be determined by measuring the relative conversion of MTT (3-[4,5-dimethylthiazol-2-yl]-2,5-diphenyltetrazolium bromide) in the test article-treated tissues compared to the negative/solvent control-treated tissues.

The MelanoDerm™ Skin Model provided by MatTek Corporation (Ashland, MA) will be used in this study. The MelanoDerm™ tissue consists of normal, human-derived epidermal keratinocytes (NHEKs) and melanocytes (NHMs) which have been cultured to form a multilayered, highly differentiated model of the human epidermis. The NHMs within co-cultures undergo spontaneous melanogenesis leading to tissues of varying levels of pigmentation. The cultures are grown on cell culture inserts at the air-liquid interface, allowing for topical application of skin modulators. The MelanoDerm™ model exhibits in vivo-like morphological and ultrastructural characteristics. NHMs localized in the basal cell layer of MelanoDerm™ tissues are dendritic and spontaneously produce melanin granules which progressively populate the layers of the tissue. Thus the test system may be used to screen for materials which may inhibit or stimulate the production of melanin relative to the negative controls.

The experimental design of this study consists of the determination of the pH of the neat test article if possible (and/or dosing solution as appropriate) and a definitive assay to determine the relative tissue viability after repeated exposures. The MelanoDerm™ Skin Model will be exposed to the test article for a total of 7 days. The test article will be topically applied to the MelanoDerm™ Skin Model every 48 hours (within a timeframe of 48±2 hours from previous treatment). The toxicity of the test article will be determined by the NAD(P)H-dependent microsomal enzyme reduction of MTT (and, to a lesser extent, by the succinate dehydrogenase reduction of MTT) in control and test article-treated tissues. (Berridge et al., 1996). Data will be presented in the form of relative survival (MTT conversion relative to the negative control).

Materials

MelanoDerm™ Maintenance Medium (EPI-100-LLMM) and MelanoDerm™ Skin Model (MEL-300-A) were supplied by MatTek Corporation. 1% Kojic acid (prepared in sterile, deionized water) and MTT (3-[4,5-dimethylthiazol-2-yl]-2,5-diphenyltetrazolium bromide) were supplied by Sigma. Dulbecco's Modified Eagle's Medium (DMEM)

containing 2 mM L-glutamine (MTT Addition Medium) was supplied by Quality Biological. Isopropanol was supplied by Aldrich. Sterile $Ca^{++}$ and $Mg^{++}$ Free Dulbecco's Phosphate Buffered Saline (CMF-DPBS) was supplied by Invitrogen or equivalent. Sterile Deionized Water was supplied by Quality Biological or equivalent. DMSO was supplied by CiVenti Chem.

Assay Procedures

Test articles will generally be tested neat or as directed by the Sponsor (see Protocol Attachment 1). Ten microliters (10 µL) or 25 µL of each test article will be applied directly on the tissue so as to cover the upper surface. Depending on the nature of the test article (liquids, gels, creams, foams, etc.), the use of a dosing device, mesh or other aid to allow the uniform spreading of the test article over the surface of the tissue may be necessary.

In the days of dosing, each test article will be diluted at least 200-fold using the appropriate volume of EPI-100-LLMM (or alternate solvent as determined during the solubility testing). A fresh dilution in EPI-100-LLMM will be prepared for each dosing. The final dilution to be performed for dosing solution preparation will be determined from the solubility assessment above and documented in the study workbook.

DMSO diluted as 0.5% (v/v) in EPI-100-LLMM will be used as vehicle control and dosed onto the tissues (10 µL and 25 µL doses) based on the same procedure used for the test articles and assay controls.

The test articles will be applied topically to the Melano-Derm™ tissue every 48 hours (within a timeframe of 48±2 hours from previous treatment) during a 7-day trial. Ten and 25 microliters, respectively, of each test article will be applied to each tissue. Twenty five microliters of the positive and negative controls, respectively, will be applied to each tissue.

The pH of the neat liquid test article (and/or dosing solution as appropriate) will be determined, if possible. The pH will be determined using pH paper (for example, with a pH range of 0-14 to estimate, and/or a pH range of 5-10 to determine a more precise value). The typical pH increments on the narrower range pH paper are approximately 0.3 to 0.5 pH units. The maximum increment on the pH paper is 1.0 pH units.

The definitive assay will include a negative control and a positive control. The MelanoDerm™ tissues designated to the assay negative control will be treated with 25 µL of sterile, deionized water. Twenty five microliters of 1% Kojic acid (prepared in sterile, deionized water and filtered at the time of preparation) will be used to dose the tissues designated to the assay positive control. The 1% Kojic acid will be stored in a tube covered with aluminum foil until used within 2 hours of preparation. The negative and positive control exposure times will be identical to those used for the test articles.

It is necessary to assess the ability of each test article to directly reduce MTT. A 1.0 mg/mL MTT solution will be prepared in MTT Addition Medium as described below. Approximately 25 µL of the test article will be added to 1 mL of the MTT solution and the mixture incubated in the dark at 37° C.±1° C. for one to three hours. A negative control, 25 µL of sterile, deionized water, will be tested concurrently. If the MTT solution color turns blue/purple, the test article is presumed to have reduced the MTT. Water insoluble test materials may show direct reduction (darkening) only at the interface between the test article and the medium.

The MTT direct reduction test for the test article(s) may have been previously performed in an independent study. In such cases, the results of the MTT direct reduction test may be used for this specific study and the initial study will be referenced.

Tissue Exposure: At least 16 hours after initiating the cultures, two MelanoDerm™ tissues (considered untreated at Day 0) will be photographed using a digital camera to aid in the visual assessment of the degree of pigmentation of the tissues at time zero of the assay. The exact procedures used to collect images of the tissues will be specified in the study workbook and report. The MelanoDerm™ tissues will be rinsed with CMF-DPBS, will be blotted dry on sterile absorbent paper and cleared of excess liquid. The MelanoDerm™ tissues will be transferred to the appropriate MTT containing wells after rinsing and processed in the MTT assay as described in the MTT Assay section.

At least 16 hours after initiating the cultures, the tissues will be moved on a new 6-well plate containing 0.9 mL of fresh, pre-warmed EPI-100-LLMM. The trial will be conducted over a 7-day timeframe. Two tissues will be treated topically on the first day, and every 48 hours (within a timeframe of 48+/−2 hours from previous treatment) with 10 and 25 microliters, respectively, of each test article. The medium will be refreshed daily (within a timeframe of 24+/−2 hours from previous refeeding); the tissues will be moved to a new 6-well plate containing 0.9 mL of fresh, pre-warmed EPI-100-LLMM.

Two tissues will be treated topically on the first day, and every 48 hours (within a timeframe of 48+/−2 hours from previous treatment) with 25 µL of positive and negative controls, respectively. The medium will be refreshed daily (within a timeframe of 24+/−2 hours from previous refeeding); the tissues will be moved to a new 6-well plate containing 0.9 mL of fresh, pre-warmed EPI-100-LLMM. The tissues will be incubated at 37±1° C. in a humidified atmosphere of 5±1% CO2 in air (standard culture conditions) for the appropriate exposure times.

On the days of dosing, the MelanoDerm™ tissue will be first gently rinsed three times using ~500 µL of CMF-DPBS to remove any residual test article. The tissues will then be moved to a new 6-well plate containing 0.9 mL of fresh, pre-warmed EPI-100-LLMM and dosed with the appropriate test article, negative or positive control. The tissues will be incubated at 37±1° C. in a humidified atmosphere of 5±1% CO2 in air (standard culture conditions) for the appropriate exposure times. The exact rinsing procedure will be documented in the study workbook.

At the end of the 7-day trial, the MelanoDerm™ tissues dosed with the negative or positive control, and with each test article will be photographed using a digital camera to aid in the visual assessment of the degree of pigmentation of the tissues at the end of the assay (Day 7). The exact procedures used to collect images of the tissues will be specified in the study workbook and report. Then, the viability of the tissues will be determined by MTT reduction as indicated below.

MTT Assay: A 10× stock of MTT prepared in PBS (filtered at time of batch preparation) will be thawed and diluted in warm MTT Addition Medium to produce the 1.0 mg/mL solution no more than two hours before use. Three hundred µL of the MTT solution will be added to each designated well of a pre-labelled 24-well plate.

After the exposure time, each MelanoDerm™ tissue designated for the MTT assay will be rinsed with CMF-DPBS, blotted dry on sterile absorbent paper, and cleared of excess liquid. The MelanoDerm™ tissues will be transferred to the appropriate MTT containing wells after rinsing. The 24-well plates will be incubated at standard conditions for 3±0.1 hours.

After 3±0.1 hours, the MelanoDerm™ tissues will be blotted on sterile absorbent paper, cleared of excess liquid, and transferred to a pre-labelled 24-well plate containing 2.0 mL of isopropanol in each designated well. The plates will be covered with parafilm and stored in the refrigerator (2-8° C.) until the last exposure time is harvested. If necessary, plates may be stored overnight (or up to 24 hours after the last exposure time is harvested) in the refrigerator prior to extracting the MTT. Then the plates will be shaken for at least 2 hours at room temperature. At the end of the extraction period, the liquid within the cell culture inserts will be decanted into the well from which the cell culture insert was taken. The extract solution will be mixed and 200 µL transferred to the appropriate wells of 96-well plate. Two hundred µL of isopropanol will be added to the wells designated as blanks. The absorbance at 550 nm (OD550) of each well will be measured with a Molecular Devices Vmax plate reader (with AUTOMIX function on).

In cases where the test article is shown to reduce MTT, only test articles that remain bound to the tissue after rinsing, resulting in a false MTT reduction signal, present a problem. To demonstrate that possible residual test article is not acting to directly reduce the MTT, a functional check is performed in the definitive assay to show that the test material is not binding to the tissue and leading to a false MTT reduction signal.

To determine whether residual test article is acting to directly reduce the MTT, a freeze-killed control tissue is used. Freeze killed tissue is prepared at IIVS by placing untreated MelanoDerm™/EpiDerm™ (Melanoderm™ without melanocytes) tissues in the −20° C. freezer at least overnight, thawing to room temperature, and then refreezing. Once killed, the tissue may be stored indefinitely in the freezer. Freeze killed tissues may be received already prepared from MatTek Corporation, and stored in the −20° C. freezer until use. To test for residual test article reduction, killed tissues are treated with the test article in the normal fashion. All assay procedures will be performed in the same manner as for the viable tissue. At least one killed control treated with sterile deionized water (negative killed control) will be tested in parallel since a small amount of MTT reduction is expected from the residual NADH and associated enzymes within the killed tissue.

If little or no MTT reduction is observed in the test article-treated killed control, the MTT reduction observed in the test article-treated viable tissue may be ascribed to the viable cells. If there is appreciable MTT reduction in the treated killed control (relative to the amount in the treated viable tissue), additional steps must be taken to account for the chemical reduction or the test article may be considered untestable in this system. The OD550 values from the killed controls will be analyzed as described below The raw absorbance data will be captured and saved as a print-file and imported into an Excel spreadsheet. The mean OD550 value of the blank wells will be calculated. The corrected mean OD550 value of the negative control(s) will be determined by subtracting the mean OD550 value of the blank wells from their mean OD550 values. The corrected OD550 values of the individual test article exposures and the positive control exposures will be determined by subtracting from each the mean OD550 value for the blank wells. All calculations will be performed using an Excel spreadsheet. Although the algorithms discussed are performed to calculate the final endpoint analysis at the treatment group level, the same calculations can be applied to the individual replicates.

Corr. test article exposure $OD550$=Test article exposure $OD550$−Blank mean $OD550$ If killed controls (KC) are used, the following additional calculations will be performed to correct for the amount of MTT reduced directly by test article residues. The raw OD550 value for the negative control killed control will be subtracted from the raw OD550 values for each of the test article-treated killed controls, to determine the net OD550 values of the test article-treated killed controls.

Net $OD550$ for each test article KC=Raw $OD550$ test article KC−Raw $OD550$ negative control KC The net OD550 values represent the amount of reduced MTT due to direct reduction by test article residues at specific exposure times. In general, if the net OD550 value is greater than 0.150, the net amount of MTT reduction will be subtracted from the corrected OD550 values of the viable treated tissues to obtain a final corrected OD550 value. These final corrected OD550 values will then be used to determine the % of Control viabilities.

Final Corrected $OD550$=Corrected test article $OD550$ (viable)−Net $OD550$ test article (KC)

Finally, the following % of Control calculations will be made:

% viability=[(Final corrected $OD550$ of Test Article or Positive Control)/(Corrected mean $OD550$ of Negative Control)]×100

Results

MelanoDerm™ assay results are shown in FIGS. 16A-16K. Malassezin-, compound I-, and compound II-treated tissues demonstrated reduced pigmentation on day 7 of the experiment. FIGS. 17A-17K show 15× magnification images of MelanoDerm™ samples exposed to the listed treatment.

Example 13

Zebrafish Assays

Assay Procedures

Compounds: Compounds will be provided by Study Sponsor as Master Stock (MS) solution at the highest soluble concentration in water/PBS or DMSO.

Standard procedures for embryo collection: Phylonix AB zebrafish will be generated by natural mating or using a Mass Embryo Production System (MEPS, Aquatic Habitats). Approximately 50 zebrafish will be generated per female zebrafish. Zebrafish will be maintained at 28° C. in fish water. Zebrafish will be cleaned (dead zebrafish removed) and sorted by developmental stage. Because zebrafish receive nourishment from an attached yolk sac, no feeding is required for 6 days post fertilization (dpf).

Compound Solubility: Master Stock (MS) (using the highest concentration) will be diluted in pure DMSO to sub-stock solutions (SS) ie: 10, 50, 100, 200, 300 mM, etc. Fish water [200 mg Instant Ocean Sea Salt (Aquarium Systems) per liter of deionized water; pH 6.6-7.0 maintained with 2.5 mg/liter Neutral Regulator (Seachem Laboratories Inc.); conductivity 850-950 µS], supplied by Phylonix, will be dispensed into a testing vessel, 4 ml/vessel.

To generate test compound solution (TS), 4 µl of each SS will be added directly to fish water. Example: 4 µl of 10 mM SS added to fish water will generate 10 μM TS; final DMSO concentration will be 0.1%. Alternatively, to obtain the same final TS and DMSO concentrations, 10 μl SS can be added to 10 ml/vessel of fish water. For assays that can tolerate DMSO up to 1%, 40 μl of SS can be used to generate 100 μM TS. If 10 ml fish water is used, volume of SS should be increased proportionally to obtain the same final TS and DMSO concentrations. The solution will be incubated at 28° C. for the length of time specified for each assay and visually examined daily for presence of precipitation.

Maximum Tolerable Concentration (MTC): MTC ($LC_{10}$) will be used as the standard criterion for compound lethality, determined using 10 compound concentrations. After determining the highest soluble compound concentration, Study Sponsor will select 10 concentrations.

Thirty ~2 dpf chorionated Phylonix wild-type AB zebrafish will be distributed into wells of 6-well microplates containing 4 ml/well fish water and DMSO at a concentration ranging from 0.1-1% depending on compound solubility.

10 concentrations (i.e.: 0.01, 0.05, 0.1, 0.5, 1, 5, 10, 50, 100, and 500 μM (or up to the concentration permitted by compound solubility), will be tested initially. If necessary, additional higher (up to 2000 μM) or lower (down to 0.001 μM) concentrations will be tested.

Zebrafish will be incubated with each concentration of test compound in the dark at 28° C. for 3 days. Untreated and 0.1-1% DMSO treated zebrafish will be used as assay and vehicle controls. To calculate % lethality, after treatment, number of dead zebrafish will be counted daily and removed. At 5 dpf, dead animals will be counted to calculate % lethality (=total number of dead zebrafish/30). Note, if dead zebrafish disintegrate, number of dead zebrafish will be deduced by counting number of live zebrafish.

To estimate MTC, lethality curves will be generated by plotting % lethality vs concentration using EXCEL software. To obtain mean and SD of MTC, experiments will be performed 3 times.

Visually assess compound effect on zebrafish skin pigmentation: Zebrafish skin pigment cells including xanthophores, iridophores, and melanophores (melanocytes) originate from neural crest cells. In zebrafish, differentiated skin pigment precursor cells express pigment at ~24 hpf. The focus of this study is melanocytes which express melanin, the black pigment on the surface of the skin. Melanocytes initially appear as small patches of black color in the dorsal head region. As zebrafish develop, the number of patches increase and fuse to form bands which extend to the tail region. In contrast, mutant albino zebrafish exhibit sparse skin pigmentation. Compounds will be administered at 2 dpf, to assess if compounds arrest the continuous process of embryonic pigmentation, which is completed by 5 dpf. Three concentrations, MTC, 50% MTC, and 25% MTC, will be tested for each compound.

Thirty 2 dpf self-hatched Phylonix wild-type AB zebrafish will be treated with each compound concentration for 3 days. Untreated and 0.1% DMSO treated zebrafish will be used as controls. Positive control: phenylthiourea (PTU, 0.03%).

Zebrafish will be visually examined daily using a dissecting light microscope; compound and PTU treated zebrafish will be compared to untreated and vehicle treated control zebrafish. Number of zebrafish exhibiting decreased pigmentation will be counted daily and expressed as % of test animals; a representative image will be provided. To identify optimum compound concentration and treatment time for decreased pigmentation, a kinetic curve will be generated by plotting % zebrafish exhibiting decreased skin pigmentation vs. time (dpf). Fisher's exact test will be used to determine if compound effect is significant ($P<0.05$).

Additional visual assessment of compound effect on zebrafish skin pigmentation will be performed after treatment with: 0.1, 1, and 3 μM. Thirty 2 dpf self-hatched Phylonix wild-type AB zebrafish will be treated with each compound concentration for 3 days. Untreated and 0.1% DMSO treated zebrafish will be used as controls. Positive control: phenylthiourea (PTU, 0.003%). Zebrafish will be visually examined daily using a dissecting light microscope; compound and PTU treated zebrafish will be compared to untreated and vehicle treated control zebrafish.

At 5 dpf, number of zebrafish exhibiting decreased pigmentation will be counted and expressed as % of test animals; a representative image will be provided. To identify optimum compound concentration and treatment time for decreased pigmentation, a kinetic curve will be generated by plotting % zebrafish exhibiting decreased skin pigmentation vs concentration. Fisher's exact test will be used to determine if compound effect is significant ($P<0.05$).

Quantitate compound effect on zebrafish skin pigmentation: Based on results from the visual assessment, we will use the optimum conditions (concentration, compound treatment time) to quantitate compound effect on zebrafish skin pigmentation.

Twenty Phylonix wild-type AB zebrafish at the optimum stage determined by results from the visual assessment will be treated with optimum compound concentration. Untreated and 0.1% DMSO treated zebrafish will be used as controls. Positive control: phenylthiourea (PTU, 0.03%).

Dorsal view image of whole zebrafish will be captured using a SPOT camera at 2×. Dorsal head and trunk region will be defined as region of interest (ROI) using Adobe Photoshop selection function. Black skin pigmentation in the ROI will be highlighted using Photoshop highlighting function. Total pigment signal (PS) in pixels will be determined using the Photoshop histogram function.

If compound affects zebrafish growth, body length (L) and trunk width (W) will be smaller, which will affect ROI area and final PS. Therefore, we will normalize measurement of final signal (FS) using FS=PS/L×W.

Untreated and vehicle treated zebrafish are expected to exhibit similar FS to demonstrate that vehicle does not have an effect. PTU treated zebrafish are expected to exhibit low FS to validate the assay. Compound treated zebrafish will be compared with vehicle treated control zebrafish.

To determine if compound effect is significant ($P<0.05$), mean FS for compound treated zebrafish will be compared to mean FS of vehicle treated zebrafish using Student's t test.

Additional quantitation of compound effect on zebrafish skin pigmentation will be performed after treatment with: 0.5 and 1.5 μM compound concentration.

Twenty 2 dpf Phylonix wild-type AB zebrafish will be treated with 0.5 and 1.5 μM compound concentration. Untreated and 0.1% DMSO treated zebrafish will be used as controls. Positive control: phenylthiourea (PTU, 0.003%).

Dorsal view image of whole zebrafish will be captured using a SPOT camera at 2×. Dorsal head region will be defined as region of interest (ROI) using Adobe Photoshop selection function. Black skin pigmentation in the ROI will be highlighted using Photoshop highlighting function. Total pigment signal (PS) in pixels will be determined using the Photoshop histogram function.

If compound affects zebrafish growth, body length (L) will be shorter and trunk width (W) will be smaller, which will affect ROI area and final PS. Therefore, we will normalize final signal (FS) measurement using FS=PS/L×W.

Untreated and vehicle treated zebrafish are expected to exhibit similar FS to confirm no effect of vehicle. PTU treated zebrafish are expected to exhibit low FS, validating the assay. Compound treated zebrafish will be compared with vehicle treated control zebrafish.

To determine if compound effect is significant (P<0.05), mean FS for compound treated zebrafish will be compared to mean FS of vehicle treated zebrafish using Student's t test.

Results

Visual assessment results for zebrafish exposed to compound II are shown in FIGS. 18A-18F and FIGS. 19A-19F. A chart summarizing results from the visual assessment portion of the study is shown in FIG. 20.

Quantitative assessment regions of interest and results for zebrafish exposed to compound II are shown in FIGS. 21A-21E and FIGS. 22A-22B.

Example 14

Stability of Malassezin and Malassezin Derivatives in DMSO and Cell Culture Media Tested compounds were prepared at 100 µM in DMSO and culture medium. The solutions were incubated at room temperature for 2 hours and analyzed using LC-MS. The peak area was used to evaluate the compound remaining in the solvent.

Results

The LC-MS results are shown in FIGS. 23A-23J. The results indicate that the compounds are stable in culture medium after 2-hour incubation.

DOCUMENTS

Berridge, M. V., Tan, A. S., McCoy, K. D., Wang, R. The Biochemical and Cellular Basis of Cell Proliferation Assays That Use Tetrazolium Salts. Biochemica 4:14-19 (1996).

Black, et al. Athymic Nude Mice and Human Skin Grafting. In: Maibach, et al. (eds.). Models in Dermatology Vol. 1. Karger, Basel, 1985, 228-39.

Costin, G.-E., Raabe, R. Optimized in vitro pigmentation screening assay using a reconstructed three dimensional human skin model. Rom. J. Biochem. 50 (1), 15-27 (2013).

Donato, et al. A Microassay for Measuring Cytochrome P450IA1 and P450IIB1 Activities in Intact Human and Rat Hepatocytes Cultured on 96-Well Plates. Anal Biochem. 1993; 213(1):29-33.

Elmore. Apoptosis: A Review of Programmed Cell Death. Toxicologic Pathology 2007; 35:495-516.

Fitzpatrick, et al. The Validity and Practicality of Sun-Reactive Skin Types I Through VI. Arch Dermatol. 1988; 124(6):869-871.

Gaitanis, et al. Skin Diseases Associated With *Malassezia* Yeasts: Facts and Controversies. Clinics in Dermatology 2013; 31:455-463.

Guého, et al. The Genus *Malassezia* With Description of Four New Species. Antonie Van Leeuwenhoek 1996; 69:337-55.

Karchner, et al. Identification and Functional Characterization of Two Highly Divergent Aryl Hydrocarbon Receptors (AHR1 and AHR2) in the Teleost *Fundulus heteroclitus*. The Journal of Biological Chemistry 1999; 274 (47):33814-24.

Krämer, et al. Malassezin, A Novel Analyst of the Aryl Hydrocarbon Receptor From The Yeast *Malassezia furfur*, Induces Apoptosis in Primary Human Melanocytes. ChemBioChem 2005; 6:860-5.

Lee, et al. Comparison of Gene Expression Profiles Between Keratinocytes, Melanocytes and Fibroblasts. Ann Dermatol. 2013; 25(1):35-45.

Manning, et al. Maintenance of Skin Xenografts of Widely Divergent Phylogenetic Origin on Congenitally Athymic (Nude) Mice. J Exp Med 1973; 138:488-94.

Nazzaro-Porro, et al. Identification of Tyrosinase Inhibitors in Cultures of *Pityrosporum*. The Journal of Investigative Dermatology 1978; 71:205-208.

Noakes. The Aryl Hydrocarbon Receptor: A Review of Its Role in the Physiology and Pathology of the Integument and Its Relationship to the Tryptophan Metabolism. Journal of Tryptophan Research 2015; 8: 17-18.

Otulakowski, et al. Use of a Human Skin-Grafted Nude Mouse Model for the Evaluation of Topical Retinoic Acid Treatment. J Invest Dermatol 1994; 102:515-8.

Park, J. I., Lee, H. Y., Lee, J. E., Myung, C. H., Hwang, J. S. Inhibitory effect of 2-methyl-naphtho[1,2,3-de]quinolin-8-one on melanosome transport and skin pigmentation. Sci. Rep. July 6:6:29189. Doi: 10.1038/srep29189 (2016).

Plenat, et al. Host-Donor Interactions in Healing of Human Split-Thickness Skin Grafts Onto Nude Mice: In Situ Hybridization, Immunohistochemical and Histochemical Studies. Transplantation 1992; 53:1002-10.

Reed, et al. Long-Term Maintenance of Normal Human Skin on Congenitally Athymic (Nude) Mice. Proc Soc Exp Biol Med 1973; 143:350-3.

Scott, et al. The Permeability of Grafted Human Transplant Skin in Athymic Mice. J Pharm Pharmacol 1988; 40:128-9.

Song, et al. A Ligand For The Aryl Hydrocarbon Receptor Isolated From Lung. PNAS 2002; 99(23):14694-9.

Taylor, et al. The Taylor Hyperpigmentation Scale: a new visual assessment tool for the evaluation of skin color and pigmentation. Cutis. 2005 October; 76(4):270-4.

Wang, et al. Stress-Induced RNASET2 Overexpression Mediates Melanocyte Apoptosis Via The TRAF2 Pathway In Vitro. Cell Death and Disease 2014; 5:e1022

Wasmeier, et al. Melanosomes At A Glance. Journal of Cell Science 2008; 121:3995-3999.

Wille, et al. Malassezin—A Novel Agonist of the Arylhydrocarbon Receptor From The Yeast *Malassezia furfur*. Bioorganic & Medicinal Chemistry 2001; 9:955-60.

Winston-McPherson, et al. Synthesis and Biological Evaluation of 2,3'-diindolylmethanes as Agonists of Aryl Hydrocarbon Receptor. Bioorganic & Medicinal Chemistry Letters 2014; 24:4023-4025.

Whyte, et al. Ethoxyresorufin-O-deethylase (EROD) Activity in Fish As A Biomarker of Chemical Exposure. Critical Reviews in Toxicology 2000; 30(4):347-570.

Yamaguchi, et al. Melanocytes and Their Diseases. Cold Spring Harb Perspect Med 2014; 4:a017046.

Zonios, et al. Skin Melanin, Hemoglobin, and Light Scattering Properties can be Quantitatively Assessed In Vivo Using Diffuse Reflectance Spectroscopy. J Invest Dermatol. 2001; 117:1452-1457.

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A method for brightening skin in a subject comprising: contacting the subject with a composition comprising:
   (a) a compound having the structure of formula (II):

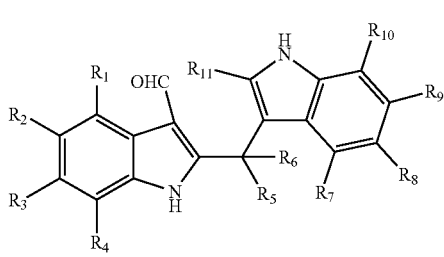

wherein:
   R1, R2, R3, R4, R5, R6, R7, R8, R9, R10, and R11 are independently selected from the group consisting of hydrogen and methyl;
   or a cosmetically or pharmaceutically acceptable salt thereof,
   (b) a cosmetically or pharmaceutically acceptable vehicle, diluent or carrier, and
   (c) one or more ingredients selected from the group consisting of perfumes, estrogen, vitamin A, vitamin C, vitamin E, pyruvic acid, lactic acid, glycolic acid, lanolin, vaseline, aloe vera, methyl paraben, propyl paraben, and pigments,
   wherein the composition is a cosmetic composition.

2. A method for brightening skin in a subject comprising: contacting the subject with a composition comprising:
   (a) a compound having the structure of formula (II):

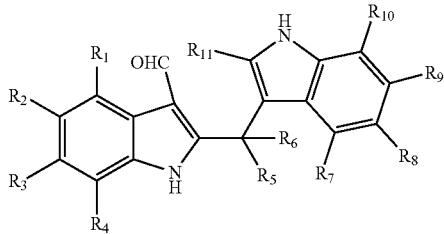

wherein:
   R1, R2, R3, R4, R5, R6, R7, R8, R9, R10, and R11 are independently selected from the group consisting of hydrogen and methyl;
   or a cosmetically or pharmaceutically acceptable salt thereof, and
   (b) a cosmetically or pharmaceutically acceptable vehicle, diluent or carrier,
   wherein the cosmetically or pharmaceutically acceptable vehicle, diluent or carrier comprises one or more ingredients selected from the group consisting of lactose, sucrose, mannitol, sorbitol, a starch, a calcium phosphate, sodium citrate, ethyl alcohol, propyl alcohol, benzyl alcohol, a polyol, a triglyceride, a biodegradable polymer, an elastomeric matrix, liposomes, microspheres, corn oil, germ oil, olive oil, castor oil, sesame oil, cottonseed oil, groundnut oil, cocoa butter, a wax, paraffin, silicone, talc, and silicylate.

3. A method for brightening skin in a subject comprising: contacting the subject with a composition comprising:
   (a) a compound having the structure of formula (II):

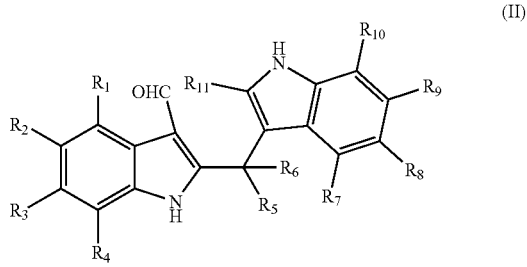

wherein:
   R1, R2, R3, R4, R5, R6, R7, R8, R9, R10, and R11 are independently selected from the group consisting of hydrogen and methyl;
   or a cosmetically or pharmaceutically acceptable salt thereof,
   (b) a cosmetically or pharmaceutically acceptable vehicle, diluent or carrier, and
   (c) one or more cosmetically acceptable compounds, ingredients and/or materials selected from the group consisting of:
   (i) starches, lactose, sucrose, glucose, mannitol, silicic acid;
   (ii) carboxymethylcellulose, alginates, gelatin, polyvinyl pyrrolidone, hydroxypropylmethyl cellulose, sucrose, acacia;
   (iii) glycerol;
   (iv) cetyl alcohol, glycerol monostearate;
   (v) kaolin, bentonite clay;
   (vi) talc, calcium stearate, magnesium stearate, solid polyethylene glycols, sodium lauryl sulfate;
   (vii) ethoxylated isostearyl alcohols, esters of polyoxyethylene sorbitol and sorbitan, microcrystalline cellulose, aluminum metahydroxide, bentonite, agar-agar, tragacanth;
   (viii) lactose, milk sugars, polyethylene glycols, animal fats, vegetable fats, oils, waxes, paraffins, cocoa butter, starches, cellulose derivatives, polyethylene glycol, silicones, bentonites, silicic acid, talc, salicylate, zinc oxide, aluminum hydroxide, calcium silicates, polyamide powder;
   (ix) preservatives;
   (x) surface-active agents;
   (xi) hydroxypropylmethyl cellulose, liposomes, microspheres, aluminum monostearate, gelatin, waxes;
   (xii) wetting agents;
   (xiii) ethyl alcohol, isopropyl alcohol, ethyl carbonate, ethyl acetate, benzyl alcohol, benzyl benzoate, propylene glycol, 1,3-butylene glycol, cottonseed oil, groundnut oil, corn oil, germ oil, olive oil, castor oil, sesame oil, glycerol, tetrahydrofuryl alcohol, polyethylene glycols, fatty acid esters of sorbitan; and
   (xiv) lecithin.

4. A method for brightening skin in a subject comprising:
contacting the subject with a composition comprising:
(a) a compound having the structure of formula (II):

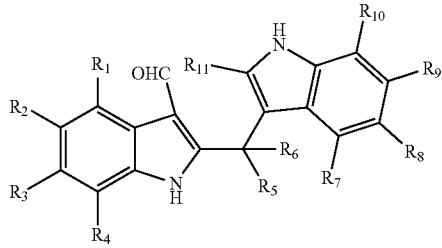
(II)

wherein:
R1, R2, R3, R4, R5, R6, R7, R8, R9, R10, and R11 are independently selected from the group consisting of hydrogen and methyl;
or a cosmetically or pharmaceutically acceptable salt thereof, and
(b) one or more cosmetically or pharmaceutically acceptable carriers selected from the group consisting of a cosmetically or pharmaceutically acceptable liquid, cream, oil, lotion, ointment, gel, and solid.

5. The method for brightening skin in a subject of claim 1, wherein the composition is a topical or transdermal composition selected from the group consisting of a powder, spray, ointment, paste, cream, lotion, gel, patch, emulsion, suspension, aerosol, and inhalant.

6. The method for brightening skin in a subject of claim 2, wherein the composition is a topical or transdermal composition selected from a powder, spray, ointment, paste, cream, lotion, gel, patch, emulsion, suspension, aerosol, and inhalant.

7. The method for brightening skin in a subject of claim 3, wherein the composition is a topical or transdermal composition selected from a powder, spray, ointment, paste, cream, lotion, gel, patch, emulsion, suspension, aerosol, and inhalant.

8. The method for brightening skin in a subject of claim 4, wherein the compound is selected from the group consisting of

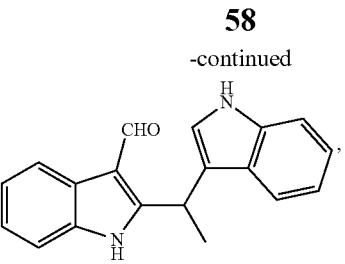,

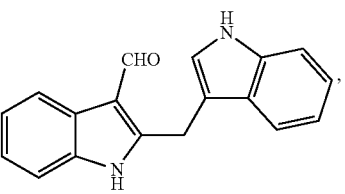,

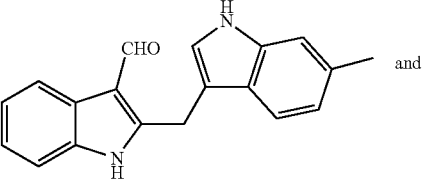 and or a cosmetically or pharmaceutically acceptable salt thereof.

9. The method for brightening skin in a subject of claim 5, wherein the compound is selected from the group consisting of

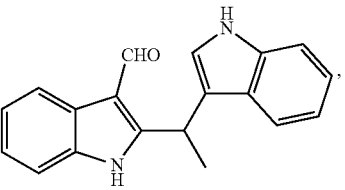,

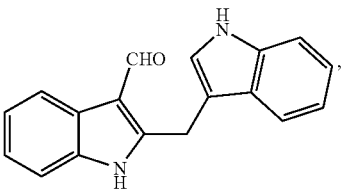,

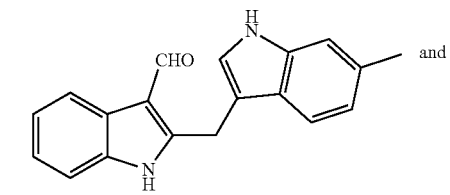 and or a cosmetically or pharmaceutically acceptable salt thereof.

10. The method for brightening skin in a subject of claim 6, wherein the compound is selected from the group consisting of -continued

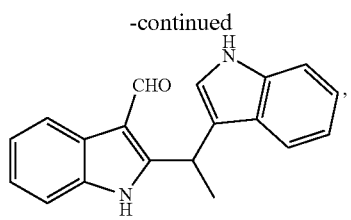

or a cosmetically or pharmaceutically acceptable salt thereof.

11. The method for brightening skin in a subject of claim 7, wherein the compound is selected from the group consisting of

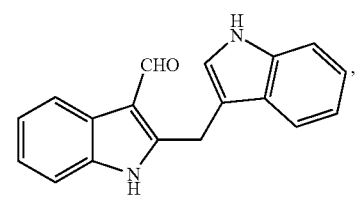

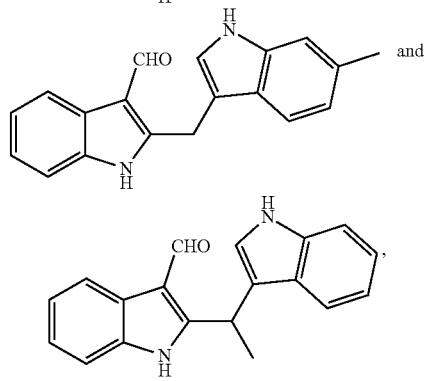

and

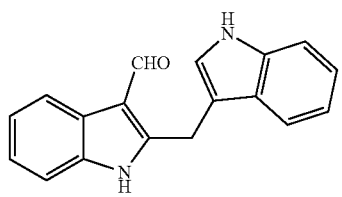 [SMILES: O=Cc1c(Cc2c[nH]c3ccccc23)[nH]c2ccccc12]

or a cosmetically or pharmaceutically acceptable salt thereof.

12. The method for brightening skin in a subject of claim 8, wherein the compound is 13. The method for brightening skin in a subject of claim 9, wherein the compound is

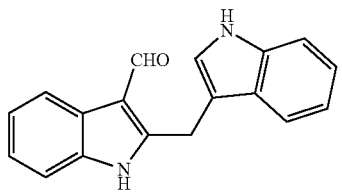 [SMILES: O=Cc1c(Cc2c[nH]c3ccccc23)[nH]c2ccccc12]

or a cosmetically or pharmaceutically acceptable salt thereof.

14. The method for brightening skin in a subject of claim 10, wherein the compound is

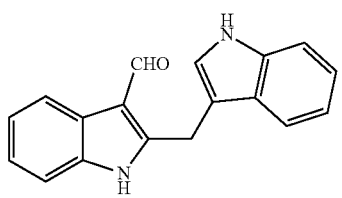 [SMILES: O=Cc1c(Cc2c[nH]c3ccccc23)[nH]c2ccccc12]

or a cosmetically or pharmaceutically acceptable salt thereof.

15. The method for brightening skin in a subject of claim 11, wherein the compound is

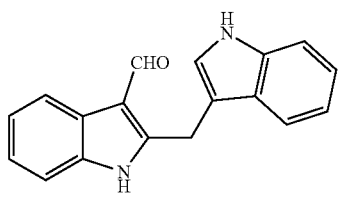 [SMILES: O=Cc1c(Cc2c[nH]c3ccccc23)[nH]c2ccccc12]

or a cosmetically or pharmaceutically acceptable salt thereof.

* * * * *